(12) United States Patent
Karsenty et al.

(10) Patent No.: US 8,759,364 B2
(45) Date of Patent: Jun. 24, 2014

(54) METHODS OF TREATING BONE MASS DISEASES

(75) Inventors: Gerard Karsenty, New York, NY (US); Patricia F. Ducy, New York, NY (US); Yuli Xie, Shanghai (CN); Donald Landry, New York, NY (US); Vijay Kumar Yadav, New York, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 380 days.

(21) Appl. No.: 12/935,651

(22) PCT Filed: Mar. 30, 2009

(86) PCT No.: PCT/US2009/038817
§ 371 (c)(1),
(2), (4) Date: Dec. 21, 2010

(87) PCT Pub. No.: WO2009/123978
PCT Pub. Date: Oct. 8, 2009

(65) Prior Publication Data
US 2011/0152220 A1    Jun. 23, 2011

Related U.S. Application Data

(60) Provisional application No. 61/072,596, filed on Mar. 31, 2008, provisional application No. 61/090,940, filed on Aug. 22, 2008.

(51) Int. Cl.
*A61K 31/505* (2006.01)
(52) U.S. Cl.
USPC ........................................................ 514/269
(58) Field of Classification Search
USPC ........................................................ 514/269
See application file for complete search history.

(56) References Cited

U.S. PATENT DOCUMENTS

| | | | |
|---|---|---|---|
| 4,472,387 | A | 9/1984 | Laruelle et al. |
| 6,004,765 | A | 12/1999 | Delmas |
| 6,096,342 | A | 8/2000 | Dansereau et al. |
| 6,403,081 | B1 | 6/2002 | Papadopoulou et al. |
| 7,198,914 | B2 | 4/2007 | Maruyama et al. |
| 7,553,840 | B2 | 6/2009 | Devasagayaraj et al. |
| 2004/0127573 | A1 | 7/2004 | Stashenko et al. |
| 2005/0203130 | A1 | 9/2005 | Buntinx |
| 2006/0135415 | A1 | 6/2006 | Jameson et al. |
| 2006/0142387 | A1 | 6/2006 | Cadilla et al. |
| 2006/0165683 | A1 | 7/2006 | Karsenty et al. |
| 2007/0191344 | A1 | 8/2007 | Choidas et al. |
| 2007/0191370 | A1 | 8/2007 | Devasagayaraj et al. |
| 2007/0191479 | A1 | 8/2007 | Turnbull et al. |
| 2007/0208063 | A1 | 9/2007 | Augeri et al. |
| 2008/0032959 | A1 | 2/2008 | Alves et al. |
| 2009/0005381 | A1 | 1/2009 | Brown et al. |
| 2009/0005382 | A1 | 1/2009 | Brown et al. |
| 2009/0029993 | A1 | 1/2009 | Liu et al. |
| 2009/0054308 | A1 | 2/2009 | Sands et al. |
| 2009/0062540 | A1 | 3/2009 | Bednarz et al. |
| 2009/0088447 | A1 | 4/2009 | Bednarz et al. |
| 2009/0099206 | A1 | 4/2009 | Iimura et al. |

FOREIGN PATENT DOCUMENTS

| | | |
|---|---|---|
| CN | 1482135 A | 7/2005 |
| WO | 2007/089335 A2 | 8/2007 |
| WO | 2008/073933 A2 | 6/2008 |
| WO | 2009/002964 A1 | 12/2008 |
| WO | 2009/002970 A1 | 12/2008 |
| WO | 2009/009561 A1 | 1/2009 |
| WO | 2009/014972 A1 | 1/2009 |
| WO | 2009/029499 A1 | 3/2009 |
| WO | 2009/042733 A1 | 4/2009 |
| WO | 2009/048864 A1 | 4/2009 |
| WO | 2009045900 A1 | 4/2009 |
| WO | 2009/123978 A1 | 10/2009 |
| WO | 2010/056992 A1 | 5/2010 |
| WO | 2010/065333 A1 | 6/2010 |
| WO | WO 2010062829 A1 * | 6/2010 |

OTHER PUBLICATIONS

Liu, Q. et al., "Discovery and Characterization of Novel Tryptophan Hydroxylase Inhibitors that Selectively Inhibit Serotonin Synthesis in the Gastrointestinal Tract", J. of Phar. and Experimental Ther. (2008) vol. 325, pp. 47-55.
Yadav, Vijay K. et al., "Lrp5 Controls Bone Formation by Inhibiting Serotonin Synthesis in the Duodenum", Cell (2008), vol. 135, pp. 825-837.
Gong, Y., et al. "LDL Receptor-Related Protein 5 (LRP5) Affects Bone Accrual and Eye Development", Cell (2001), vol. 107, pp. 513-523.
Gong, D., et al., "Genomic structure and promoter analysis of the human obese gene", J. Biol Chem (1996), vol. 271:8, pp. 3971-3974.
Gordon, J.W. "Transgenic animals", Intl. Rev. Cytol. (1989), vol. 115, pp. 171-229.
Gough, N. R. "Bones calling pancreas, come in please", Sci. STKE (2007), vol. 2007:399, pp. tw288.
Gu, H. et al., "Deletion of a DNA polymerase beta gene segment in T cells using cell type-specific gene targeting", Science (1994), vol. 265, pp. 103-106.
Gundersen, H. et al., "The Conneulor: unbiased estimation of connectivity using physical disectors under projection", Bone (1993), vol. 14:217-222.
Halazy, S. et al., "5-HT1B/1D antagonists and depression", Exp. Opin. Ther. Patents (1997), vol. 7, pp. 339-352.

(Continued)

*Primary Examiner* — Kevin E Weddington
(74) *Attorney, Agent, or Firm* — Kenyon & Kenyon LLP

(57) ABSTRACT

The present invention provides methods and therapeutic agents for lowering or increasing serum serotonin levels in a patient in order to increase or decrease bone mass, respectively. In preferred embodiments, the patient is known to have, or to be at risk for, a low bone mass disease such as osteoporosis and the agents are TPH1 inhibitors or serotonin receptor antagonists.

2 Claims, 15 Drawing Sheets

(56) References Cited

OTHER PUBLICATIONS

Hamon, M., et al., "Regional differences in the transduction mechanisms of 5-HT receptors in the mammalian brain. Cardiovascular pharmacology of 5-HT", The Netherlands J. of Med. (1991), pp. 41-59.
Haney, E. M. et al., "Association of low bone mineral density with selective serotonin reuptake inhibitor use by older men", Arch Intern Med (2007), vol. 167:12, pp. 1246-1251.
Hanley, H. G. et al., "Hyperserotonemia and amine metabolites in autistic and retarded children." Arch Gen Psychiatry (1977), vol. 34:5 pp. 521-531.
He, Y. et al., "The mouse obese gene. Genomic organization, promoter activity, and activation by CCAAT/enhancer-binding protein alpha", J. Biol. Chem. (1995) vol. 270, pp. 28887-28891.
Hediger, M. L. et al., "Reduced Bone Cortical Thickness in Boys with Autism or Autism Spectrum Disorder", J Autism Dev Disord (2008), vol. 38, pp. 848-856.
Hildebrand, T. et al., "Direct three-dimensional morphometric analysis of human cancellous bone: microstructural data from spine, femur, iliac crest, and calcaneus", J. Bone Miner. Res. (1999), vol. 14, pp. 1167-1174.
Hinoi, E. et al., "The sympathetic tone mediates leptins's inhibition of insulin secretion by modulating osteocalcin bioactivity", J. Cell. Bio. (2008), vol. 183:7, pp. 1235-1242.
Holmen, S.L. et al., "Essential role of beta-catenin in postnatal bone acquisition", J. Biol. Chem. (2005), vol. 280:22, pp. 21162-21168.
Hoyer, D. et al., "International Union of Pharmacology classification of receptors for 5-hydroxy-tryptamine (Serotonin)", Pharmacol. Rev. (1994), vol. 46, pp. 157-203.
Hoyer, D. et al., "Serotonin receptors in the human brain. Characterization and autoradiographic localization of 5- HT1A recognition sites. Apparent absence of 5-HT1B recognition sites", Brain Res. (1986), vol. 376, pp. 85-96.
Hu, H. et al., "Sequential roles of Hedgehog and Wnt signaling in osteoblast development", Development (2005), vol. 132:1pp. 49-60.
Hudzik, T. J. et al.., "Behavioral pharmacology of AR-A000002, a novel, selective 5-hydroxytryptamine(1B) antagonist", Journal of Pharmacology and Experimental Therapeutics (2003), vol. 304:3, pp. 1072-1084.
Huse, W.D. et al. "Generation of a large combinatorial library of the immunoglobulin repertoire in phage lambda", Science (1989), vol. 246:1275-1281.
Hwang, C. et al., "Transcriptional activation of the mouse obese (ob) gene by CCAAT/enhancer binding protein alpha", Proc. Natl. Acad. Sci. USA (1996), vol. 93:873-877.
Johnson, M. L. et al., "Linkage of a gene causing high bone mass to human chromosome 11(11q12-13)", Am J Hum Genet (1997), vol. 60, pp. 1326-1332.
Kato, M. et al., "Cbfa1-independent decrease in osteoblast proliferation, osteopenia, and persistent embryonic eye vascularization in mice deficient in Lrp5, a Wnt coreceptor", J. Cell Biol. (2002), vol. 157:2, pp. 303-314.
Kikuchi, A. et al., "Multiplicity of the interactions of Wnt proteins and their receptors", Cellular Signalling, (2007), vol. 19:4, pp. 659-671.
Kurd-O, M. et al., "Mutation of the mouse kiotho gene leads to a syndrome resembling ageing" Nature (1997), vol. 390:6655 pp. 45-51.
Lasko, M. et al., "Targeted oncogene activated by site-specific recombination in transgenic mode", Proc. Natl. Acad. Sci. USA (1992), vol. 89, pp. 6232-6236.
Lavitrano, M. et al., "Sperm cells as vectors for introducing foreign DNA into eggs: genetic transformation of mice", Cell (1989), vol. 57, pp. 717-723.
Lee, K. N. et al., "Endocrine Regulation of Energy Metabolism by the Skeleton", Cell (2007), vol. 130, pp. 456-469.
Leonhardt, S., et al., "Detection of a novel serotonin receptor subtype (5-HT1E) in human brain: interaction with GTP-binding protein", J. Neurochem. (1989), vol. 53, pp. 465-471.

Lesurtel, M., et al., "Platelet-derived serotonin mediates liver regeneration" Science (2006), vol. 312:5770, pp. 104-107.
Levis & Altman, "Bone densitometry: clinical considerations", Arthritis and Rheumatism (1998) vol. 41, pp. 577-587.
Liu, B., et al., "Use of selective serotonin-reuptake inhibitors or tricyclic antidepressants and risk of hip fractures in elderly people", Lancet (1998), vol. 351, pp. 1303-1307.
Liu, Q. et al., "Discovery and Characterization of Novel Tryptophan Hydroxylase Inhibitors that Selectively Inhibit Serotonin Synthesis in the Gastrointestinal Tract", JPET (2008), vol. 325:1, pp. 47-55.
Lo, C. W. "Transformation by iontophoretic microinjection of DNA: multiple integrations without tandem insertions", Mol. and Cell. Biol.(1983) vol. 3:10, pp. 1803-1814.
Logan, C.Y. et al., "The Wnt signaling pathway in development and disease", Annu Rev Cell Dev Biol. (2004), vol. 20, pp. 781-810.
Mann, J. J. et al., "Relationship between central and peripheral serotonin indexes in depressed and suicidal psychiatric inpatients", Arch Gen Psychiatry (1992), vol. 49:6, pp. 442-446.
Mao, J. et al., "Low-density lipoprotein receptor-related protein-5 binds to axin and regulates the canonical Wnt Signaling Pathway", Mol Cell (2001), vol. 7, pp. 801-809.
Matsuda, M. et al., "Serotonin regulates mammary gland development via an autocrine-paracrine loop", Dev Cell (2004), vol. 6(2): p. 193-203.
Middlemiss, D. N. et al., "A pharmacological analysis of the 5-HT receptors mediating inhibition of 5-HT release in the guinea pig frontal cortex", Eur. J. Pharmacol. (1988), vol. 157, 101-107.
Mlinar & Coradetti, "Endogenous 5-HT, released by MDMA through serotonin transporter- and secretory vesicle-dependent mechanisms, reduces hippocampal excitatory synaptic transmission by preferential activation of 5-HT1B receptors located on CA1 pyramidal neurons", Eur. J. Neurosci. (2003), vol. 18, pp. 1559-1571.
Mlinar, B. et al., "Pharmacological characterization of 5-HT(1B) receptor-mediated inhibition of local excitatory synaptic transmission in the CA1 region of rat hippocampus", British Journal of Pharmacology (2003), vol. 138, pp. 71-80.
Murakami, H. et al., "Manipulation of serotonin signal suppresses early phase of behavioral aging in Caenorhabditis elegans", Neurobiloby of Aging (2008), vol. 29, pp. 1093-1100.
Nebigil, C. G. et al., "Serotonin 2B receptor is required for heart development", Proc Natl Acad Sci U serotonin A (2000), vol. 97:17, pp. 9508-9513.
Noda, M. et al., "Multiple signal transduction pathways mediated by 5-HT receptors", Mol Neurobiol. (2004), vol. 29:1, pp. 31-39.
Norman, T. R. et al., "Fast-acting antidepressants, Can the need be met?", CNS Drugs (1994), vol. 2, pp. 120-131.
Ohshima, S. et al., "Interleukin 6 plays a key role in the development of antigen-induced arthritis", Proc Natl Acad Sci U serotonin A (1998), vol. 95:14, pp. 8222-8226.
Parfitt et al., "Bone histomorphometry: standardization of nomenclature, symbols, and units. Report of the ASBMR Histomorphometry Nomenclature Committee", J. Bone Miner. Res. (1987), vol. 2, pp. 595-610.
Pauwels, P. J., "5-HT1B/1D antagonists", Gen. Pharmac. (1997), vol. 29, pp. 293-303.
Richards, J. B. et al. "Effect of selective serotonin reuptake inhibitors on the risk of fracture", Arch Intern Med (2007), vol. 167:2, pp. 188-194.
Roberts, C. et al., "Effect of the selective 5-HT1D antagonist GR127935 on vivo 5-HT release, synthesis and turnover in the guinea pig frontal cortex", Br. J. Pharmacol. (1994), vol. 112, p. 489P.
Roberts, C. et al., "Functional characterization of the 5-HT terminal autoreceptor in the guinea pig cortex", Br. J. Pharmacol. (1996), vol. 117, pp. 384-388.
Roberts, C. et al., "Importance of 5-HT1B receptor selectivity for 5-HT terminal autoreceptor activity: an in vivo microdialysis study in the freely moving guinea pig", Neuropharmacology (1997), vol. 36, pp. 549-557.
Roberts, C. et al., "Comparison of 5-HT autoreceptor control in guinea pig dorsal and median raphé innervated regions", Br. J. Pharmacol., (1997), vol. 331, p. 207.

(56) References Cited

OTHER PUBLICATIONS

Roca-Vinardell, A., et al., "The role of 5-HT1A/B autoreceptors in the antinociceptive effect of systemic administration of acetaminophen", Anesthesiology (2003), vol. 98, pp. 741-747.

Rodan & Martin, "Therapeutic approaches to bone diseases", Science (2000), vol. 289, pp. 1508-1514.

Rojas-Corrales, M. et al., "Role of 5-HT1A and 5-HT1B receptors in the antinociceptive effect of tramadol", Eur. J. Pharmacol. (2005), vol. 511, pp. 21-26.

Rosen, C. J. "Bedside to Bench: Serotonin Secrets" Nature (2009), vol. 15:2, pp. 145-146.

Trope & Clark, "Binding potencies of 3 new beta 2 specific blockers to beta receptors in the ciliary processes and the possible relevance of these drugs to intraocular pressure control", Br J Ophthalmol (1984) vol. 68:4, pp. 245-247.

Stacher, G. et al., "Effects of a 5-hydroxytryptamine3 receptor antagonist (ICS 205-930) on colonic motor activity in healthy men", Br J Clin Pharmacol. (1989), vol. 28:3, pp. 315-322.

Saudou, F. et al., "Enhanced aggressive behavior in mice lacking 5-HT1B receptor", Science (1994), vol. 265:5180, pp. 1875-1878.

Schneeweiss, S. et al., "Association between SSRI use and hip fractures and the effect of residual confounding bias in claims database studies", J Clin. Psychopharmacol (2004) vol. 24:6, pp. 632-638.

Schoeffter, P., et al., "5-Hydroxytryptamine 5-HT1B and 5-HT1D receptors mediating inhibition of adenylate cyclase activity. Pharmacological comparison with special reference to the effects of yohimbine, rauwolscine and some beta-adrenoceptor antagonists", Naunyn-Schimedebergs Arch Pharmacol. (1989), vol. 340, pp. 285-292.

Semenkovich, C. F. et al., "Bone Weighs in on Obesity", Cell (2007), vol. 130, pp. 409-411.

Shi, Z. et al., "Modulation of Peripheral Serotonin Levels by Novel Tryptophan Hydroxylase Inhibitors for the potential treatment of functional gastrointestinal disorders", J. Med. Chem. (2008), vol. 51, pp. 3684-3687.

Skingle, M. et al., "Microdialysis study investigating the effects of GR 127935, a potent 5-HT1D receptor antagonist, on cortical levels of 5-HT in the guinea pig", Br. J. Pharmacol. (1994), vol. 112, pp. C57.

Skingle, M. et al., "Effects of the HT1D receptor antagonist GR 127935 on extracellular levels of 5-HT in the guinea frontal cortex as measured by microdialysis", Neuropharmacology (1995), vol. 34, pp. 377-382.

Sprouse, J. S., et al., "Electrophysiological responses of serotoninergic dorsal raphe neurons to 5-HT1A and 5-HT1B agonists", Synapse (1987), vol. 1. pp. 3-9.

Sze, J. Y. et al., "Food and metabolic signalling defects in a *Caenorhabditis elegans* serotonin-synthesis mutant", Nature (2000), vol. 403:6769, pp. 560-564.

Takeda, S. et al., "Leptin regulates bone formation via the sympathetic nervous system", Cell (2002), vol. 111:3, pp. 305-317.

Tamai, K. et al., "LDL-receptor-related proteins in Wnt signal transduction", Nature (2000), vol. 407, pp. 530-535.

Thompson et al., "Germ line transmission and expression of a corrected HPRT gene produced by gene targeting in embryonic stem cells", Cell (1989), vol. 56, pp. 313-321.

Tsuji, K. et al., "BMP2 activity, although dispensable for bone formation, is required for the initiation of fracture healing", Nat Genet (2006), vol. 38:12, pp. 1424-1429.

Urban et al., "Involvement of peripheral presynaptic inhibition in the reduction of sympathetic tone by moxonidine, rilmenidine and UK 14304", European Journal of Pharmacology (1995), vol. 282, pp. 29-37.

Vachal, P. et al., "Synthesis and Study of Alendronate Derivatives as Potential Prodrugs of Alendronate Sodium for the Treatment of Low Bone Density and Osteoporosis", J Med. Chem. (2006), vol. 49, pp. 3060-3063.

Van der Putten, H. et al., "Efficient insertion of genes into the mouse germ line via retroviral vectors", Proc. Natl. Acad. Sci., USA (1985) vol. 82, pp. 6148-6152.

Verge, D. et al., "Quantitative autoradiography of multiple 5-HT1 receptor subtypes in the brain of control or 5,7-dihydroxytryptamine-treated rats", J. Neuroscience (1986), vol. 6, pp. 3747-3482.

Walther, D. J. et al., "Synthesis of serotonin by a second tryptophan hydroxylase isoform". Science (2003), vol. 299:5603, pp. 76.

Warden, S. J. et al., "Inhibition of the serotonin (5-hydroxytryptamine) transporter reduces bone accrual during growth", Endocrinology (2005), vol. 146:2, pp. 685-693.

Warden, S. J. et al., Neural regulation of bone and the skeletal effects of serotonin (5-hydroxytrytamine), Mol. Cell Endocrinol. (2005), vol. 242:1-2, pp. 1-9.

Watson, J. et al., "GR127935 acts as a partial agonist at recombinant human 5-HT1Dα and 5-HT1Dβ receptors", Br. J. Pharmacol. (1995), vol. 114, 362P.

Wehrli, M., et al., "Arrow encodes an LDL-receptor-related protein essential for Wingless signalling", Nature (2000), vol. 407, pp. 527-530.

Weisstaub, N. V. et al., "Cortical 5-HT2A receptor signaling modulates anxiety-like behaviors in mice", Science (2006), vol. 313:5786, pp. 536-540.

Westbroek, I. et al., "Expression of serotonin receptors in bone", J Biol Chem (2001) vol. 276:31, pp. 28961-28968.

Wilkinson & Dourish, "Serotonin and Animal Behavior", Chapter 7 From Serotonin Receptor Subtypes: Basic and Clinical Aspects, Peroutka, Ed., in "Receptor Biochemistry and Methodology" vol. 15, (1991), Venter & Harrison, eds. Wiley-Liss, NY NY, 6 pages.

Windahl, S. H. et al., "Elucidation of estrogen receptor function in bone with the use of mouse models", Trends Endocrinol Metab (2002) vol. 13:5, pp. 195-200.

Wurch et al., "Recombinant saphenous vein 5-HT1B receptors of the rabbit: comparative pharmacology with human 5-HT1B receptors", British J. Pharmacol. (1997) vol. 120, pp. 153-159.

Xie, Y. et al., "Synthesis and biological evaluation of novel bisphosphonates with dual activites on bone in vitro", Bio. Med. Chem. Letters 15 (2005), pp. 3267-3270.

Yadav, V. K. et al., "Lrp5 controls bone formation by inhibiting serotonin synthesis in the duodenum", Cell (2008), vol. 135, pp. 825-837.

Yang, X. et al., "ATF4 is a substrate of RSK2 and an essential regulator of osteoblast biology; implication for Coffin-Lowry Syndrome", Cell (2004), vol. 117:3, pp. 387-398.

Yoshida, Y. et al., "Negative regulation of BMP/Smad signaling by Tob in osteoblasts", Cell (2000), vol. 103(7), pp. 1085-1097.

Yoshizawa, T. et al., "Mice lacking the vitamin D receptor exhibit impaired bone formation, uterine hypoplasia and growth retardation after weaning", Nat Genet (1997), vol. 16:4, pp. 391-396.

Yoshizawa, T. et al., "The transcription factor ATF4 regulates glucose metabolism through its expression in osteoblasts", J Clin Invest. Sep. 1, 2009; 119(9): 2807-2817.

Zhang, Y. et al., "Positional cloning of the mouse obese gene and its human homologue", Nature (1994), vol. 372, pp. 425-432.

Zhao, G., et al., "Targeted overexpression of insulin-like growth factor to osteoblasts of transgenic mice: increased trabecular bone volume without increased osteoblast proliferation", Endocrinology (2000), vol. 141:7, pp. 2674-2682.

Zifa, E. et al., "5-hydroxytryptamine receptors", Pharmacol. Rev. (1992), vol. 44, pp. 401-458.

Abe, E. et al., "TSH is a negative regulator of skeletal remodeling", Cell (2003), vol. 115:2, pp. 151-162.

Adham, N. et al., "Cell-specific coupling of he cloned human 5-HT1F receptor to multiple signal transduction pathways", Naunyn-Schmiedebergs Arch. Pharmacol., (1993), vol. 348, pp. 566-575.

Anginot, A. et al., "Lymphocytes and Dap12 adaptor are key regulators of osteoclast activation associated with gonadal failure", PLoS ONE (2007), vol. 2:(7), e585 (pp. 1-9), doi:10.1371/journal.pone.0000585.

Ansorge, M. et al., "Inhibition of serotonin but not norepinephrine transport during development produces delayed, persistent perturbations of emotional behaviors in mice ", J. Neurosci. (2008), vol. 28:1, pp. 199-207.

Battaglino, R., et al., "Serotonin regulates osteoclast differentiation through its transporter", J. Bone Miner Res. (2004), vol. 19:9, pp. 1420-1431.

(56) References Cited

OTHER PUBLICATIONS

Beer, M. S. et al., "Serotonin-5-O-carocyrnethylclycy-[125I] tyrosinamide labels the 5-HT1Dβ receptor subtype in human cortex", Eur. J. Pharmacol. (1993), vol. 242, pp. 195-198.

Bentley, M. D. et al., "Reductive amination using poly(ethylene glycol) acetaldehyde hydrate generated in situ: applications to chitosan and lysozyme" J. Pharm. Sci. (1998), vol. 87:11, pp. 1446-1449.

Bilezikian, J. P. et al., "Targeting bone remodeling for the treatment of osteoporosis: summary of the proceedings of an ASBMR workshop ", J. Bone Miner. Res. (2009), vol. 24, pp. 373-385.

Blakely, R. D. et al., "Biogenic amine neurotransmitter transporters: just when you thought you knew them", Physiology [Bethesda] (2005), vol. 20, pp. 225-231.

Blier, P. et al., "Current advances and trends in the treatment of depression", Trends Pharmacol. Sci. (1994), vol. 15, pp. 220-226.

Bliziotes, M.M. et al., "Neurotransmitter action in osteoblasts: expression of a functional system for serotonin receptor activation and reuptake", Bone (2001), vol. 29:5, pp. 477-486.

Boutouyrie, P. et al. "Sympathetic activation decreases medium-sized arterial compliance in humans ", Am. J. Physiol. (1994) vol. 267 (4 Pt 2), pp. H1368-H1376.

Boyden, L. M. et al. "High bone density due to a mutation in LDL-receptor-related protein 5", New England J Med (2002), vol. 346:20, pp. 1513-1521.

Bundgaard, H., "Means to Enhance Penetration: Prodrugs as a means to improve the delivery of peptide drugs", Advanced Drug Delivery Review (1992), vol. 8, pp. 1-38.

Chien, K. R. et al., "Longevity and lineages: toward the integrative biology of degenerative diseases in heart, muscle, and bone", Cell (2005), vol. 120:4, pp. 533-544.

Clark, M.S. et al., "Increased expression of 5-HT1B receptor in dorsal raphe nucleus decreases fear-potentiated startle in a stress dependent manner", Brain Res. (2004), vol. 1007:1-2, pp. 86-97.

Choi, Y. et al., "Bench to Bedside: Breaking Into Bone Biology: Target Practice", Nature (2009), vol. 15:2 pp. 144-145.

Collet, C. et al., "The serotonin 5-HT2b receptor controls bone mass via osteoblast recruitment and proliferation", The FASEB Journal (2008), vol. 22, pp. 418-427.

Côté, F., et al. "Disruption of the nonneuronal tph1 gene demonstrates the importance of peripheral serotonin in cardiac function", Proc. Natl. Acad. Sci. USA (2003), vol. 100:23, pp. 13525-13530.

Dacquin, R. et al., "Mouse alpha1(I)-collagen promoter is the best known promoter to drive efficient Cre recombinase expression in osteoblast", Dev. Dyn. (2002), vol. 224, pp. 245-251.

Davidson, C., et al., "Evidence that 5-HT release in rat dorsal raphe nucleus is controlled by 5-HT1A, 5-HT1B and 5-HT1D autoreceptors", Br. J. Pharmacol. (1996), vol. 116, pp. 384-388.

Daws, L.C. et al., "5-HT1B antagonists modulate clearance of extracellular serotonin in rat hippocampus", Neuroscience Letters (1999), vol. 266, pp. 165-168.

Daws, L.C. et al., "5-HT(1B) receptor-mediated regulation of serotonin clearance in rat hippocampus in vivo", J. Neurochemistry (2000), vol. 75, pp. 2113-2122.

Day, T. F. et al., "Wnt/beta-catenin signaling in mesenchymal progenitors controls osteoblast and chondrocyte differentiation during vertebrate skeletogenesis", Dev Cell (2005), vol. 8:5, pp. 739-750.

De La Brousse, F. C., et al., "Identification of the promoter of the mouse obese gene", Proc. Natl. Acad. Sci. USA (1996) vol. 93, pp. 4096-4101.

De Ponti, F. "Pharmacology of serotonin: what a clinician should know", Gut (2004) vol. 53, pp. 1520-1535. doi 10.1136/gut.2003.035568.

De Vries, P., et al., "Interactions of GR127935, a 5-HT(1B/D) receptor ligand, with functional 5-HT receptors", Naunyn Schmiedebergs Arch. Pharmacol, (1997) vol. 355, pp. 423-430.

Diem, S. J. et al., "Use of antidepressants and rates of hip bone loss in older women: the study of osteoporotic fractures", Arch Intern Med (2007), vol. 167:12, pp. 1240-1245.

Donehower, L. A. et al., "Mice deficient for p53 are developmentally normal but susceptible to spontaneous tumours", Nature (1992), vol. 356:6366, pp. 215-221.

Ducy, P. et al., "Leptin inhibits bone formation through a hypothalamic relay: a central control of bone mass", Cell (2000), vol. 100, pp. 197-207.

Dutnall, R. N. et al., "Deciphering NAD-dependent deacetylases", Cell (2001), vol. 105:2, pp. 161-164.

Eldridge, F. L. et al., "Central regulation of respiration by endogenous neurotransmitters and neuromodulators", Annu Rev Physiol (1981), vol. 43, pp. 121-135.

Elefteriou, F. et al., "Leptin regulation of bone resorption by the sympathetic nervous system and CART", Nature (2005), vol. 434:7032, pp. 514-520.

Engel, G. et al., "Identity of inhibitory pre-synaptic 5-HT autoreceptors in the rat brain cortex with 5-HT1B binding sites", Naunyn-Schmiedebergs Arch. Pharmacol. (1986), vol. 332, pp. 1-7.

Esler & Kay, "Sympathetic nervous system activation in essential hypertension, cardiac failure and psychosomatic heart disease", J. Cardiovasc. Pharmacol.( 2000) vol. 35(7 Suppl 4): SI-7.

Feldkamp et al., "The direct examination of three-dimensional bone architecture in vitro by computed tomography", J. Bone Miner. Res. (1989) vol. 4, pp. 3-11.

Feng, Q. et al., "Effects of Clonidine on Renal Sympathetic Nerve Activity, Natriuresis and Diruresis in Chronic Congestive Heart Failure", Journal of Pharmacology and Experimental Therapeutics (1992), vol. 261, pp. 1129-1135.

Fillion, G. et al., "Modulation of affinity postsynaptic serotonin receptors by antidepressants drugs", Nature (1981), vol. 292, 349-351.

Fink, K. et al., "Subclassification of presynaptic 5-HT autoreceptors in the human brain cerebral cortex as 5-5-HT1Dβ receptors", Naunyn-Schmiedebergs Arch. Pharmacol. (1995), vol. 352, pp. 451-454.

Friedman & Halaas, "Leptin and the regulation of body weight in mammals", Nature (1998) vol. 395, pp. 763-770.

Fu, L. et al., "The molecular clock mediates leptin regulated bone formation", Cell (2005), vol. 122:5, pp. 803-815.

Gaster, L. M. et al., "The selective 5-HT1B receptor inverse agonist (SB-224298) potently blocks terminal 5-T autoreceptor function both in vitro and vivo", J. Med. Chem. (1998), vol. 44, pp. 1218-1235.

Gershon, M.D. et al., "5-HT receptor subtypes outside the central nervous system. Roles in the physiology of the gut", Neuropsychopharmacology (1990), vol. 3:(5-6), pp. 385-395.

Gershon, M.D. et al., "The serotonin signaling system: from basic understanding to drug development for functional GI disorders", Gastroenterology (2007), vol. 132:1, pp. 397-414.

Glass, D.A., 2nd, et al., "Canonical Wnt signaling in differentiated osteoblasts controls osteoclast differentiation", Dev Cell (2005), vol. 8:5, pp. 751-764.

Gobert, A. et al., "Potentiation of the fluoxetine-induced increase in dialysate levels of serotonin (5-HT) in the frontal cortex of freely moving rates by combined blockade of 5-HT1A and 5-HT1B receptors with WAY100,635 and GR127,935", J. Neurochem (1997), vol. 68, pp. 1159-1163.

\* cited by examiner

Age of the mice used for the study: 4 Weeks
n=4/5 each group

METHODS OF TREATING BONE MASS DISEASES

CROSS REFERENCE TO RELATED APPLICATIONS

This application is a 371 of International Patent Application No. PCT/US2009/038817, filed Mar. 30, 2009, which claims priority to U.S. Provisional Patent Application Ser. No. 61/072,596, filed Mar. 31, 2008 and U.S. Provisional Patent Application Ser. No. 61/090,940, filed Aug. 22, 2008. The contents of these applications are hereby incorporated by reference in their entireties.

STATEMENT OF GOVERNMENTAL INTEREST

This invention was made with Government support under NIH-5R01DK 067936 awarded by the National Institutes of Health. The Government has certain rights in the invention.

FIELD OF THE INVENTION

The invention is in the field of diagnosis and therapy of bone diseases associated with higher than normal or lower than normal bone mass.

BACKGROUND OF THE INVENTION

Bone remodeling, the mechanism whereby vertebrates renew bone tissues throughout adulthood, comprises two phases: resorption of preexisting mineralized bone matrix by a specialized cell type, the osteoclast, followed by de novo bone formation by another specialized cell type, the osteoblast. Genetic and molecular studies have shown that local effectors (cytokines, and growth factors) and systemic effectors (hormones and neuromediators) modulate both phases of bone remodeling.

One of the most intensively studied genes regulating bone remodeling is LDL-receptor related protein 5 (LRP5). Loss-of-function mutations in LRP5 result in osteoporosis pseudoglioma (OPPG), a disease characterized by severe bone loss due to a decrease in bone formation and by the persistence of embryonic vascularization of the eyes, causing blindness. By contrast, gain-of-function mutations in LRP5 cause another bone disease, high bone mass syndrome. The involvement of Lrp5 in two human diseases of opposite nature underscores the importance of the pathways controlled by this gene in the regulation of bone formation. However, the mechanism by which LRP5 affects bone development is not known.

SUMMARY OF THE INVENTION

It has been discovered that elevated levels of serum serotonin, due to overexpression of tryptophan hydroxylase 1, the enzyme responsible for the first step of serotonin synthesis in enterochromaffin cells of the duodenum, and possibly in osteoblasts, causes decreased bone mass in LRP5 loss of function mutants. Thus, certain embodiments of the invention are directed to methods for treating or preventing low bone mass diseases such as osteoporosis and OPPG by administering a therapeutic agent that inhibits serotonin synthesis or inhibits TPH1, the enzyme necessary for serotonin synthesis in duodenum, or by administering antagonists of the serotonin receptor HT1B that is the receptor mediating the effect of serotonin on osteoblasts.

Certain other embodiments of the invention are directed to pharmaceutical compositions for increasing bone mass that include therapeutic agents that decrease serum serotonin levels including one or more TPH 1 inhibitors, or one or more serotonin receptor antagonists, or both, for use in treating or preventing low bone mass diseases. In some embodiments, the present invention includes a pharmaceutical composition for treating or preventing anxiety or depression where the pharmaceutical composition includes both an SSRI and a drug that reduces the level of serum serotonin, in order to prevent patients treated with serotonin reuptake inhibitors from developing osteoporosis or to treat osteoporosis in patients taking SSRIs.

In other embodiments, the present invention provides methods of treating patients for anxiety or depression where an SSRI and a drug that reduces the level of serum serotonin are administered to a patient via separate pharmaceutical compositions.

Diseases associated with abnormally high bone mass can be treated by increasing the levels of peripheral serotonin, either by administering serotonin itself, or serotonin reuptake inhibitors that act in the periphery, HT1B agonists, activators of TPH1, or combinations thereof.

U.S. Provisional Patent Application Ser. No. 60/976,403, filed Sep. 28, 2007, and incorporated by reference herein in its entirety, discloses that brain-derived serotonin (hereafter abbreviated BDS) has the opposite effect of peripheral serotonin. Elevated BDS increases bone mass by acting through HT2C receptors on target neurons in the hypothalamus. Thus, some embodiments of the present invention include administering a combination of therapeutic agents that includes agents that decrease peripheral serotonin and agents that increase BDS. BDS can be increased by increasing the activity of TPH2, the enzyme responsible for the first step of serotonin synthesis in neurons of the brain stem, and by administering agonists of the HT2C serotonin receptor in the brain.

Other methods disclosed herein are directed to diagnosing a person at risk of developing a low bone mass disease such as osteoporosis by determining if the serum level of serotonin in the periphery is abnormally high (about 25% or more) compared to normal individuals, taking into account the age, gender, or other factors that affect serum serotonin levels. Such a person at risk may be treated with therapeutic agents that decrease serum serotonin to prevent the low bone mass disease from developing. Those of skill in the art will understand that serum serotonin levels may vary among individuals depending on certain factors and will be able to take those factors into account to determine whether a person has abnormally high serum serotonin levels. One possible range which those skilled in the art may consider to be normal serum serotonin levels is 101-283 ng/ml (nanograms per milliliter).

Since elevated serum serotonin may not be the only cause of diseases associated with low bone mass, methods other than those measuring serum serotonin levels may also be used to determine if a person having a low bone mass disease such as osteoporosis should be treated with drugs that decrease serum serotonin.

The present invention provides a method of lowering serum serotonin levels in a patient known or suspected to be in need of lowering of serum serotonin levels comprising administering to the patient known or suspected to be in need of lowering of serum serotonin levels a TPH1 inhibitor or a serotonin receptor antagonist.

The present invention also provides a method of treating or preventing a low bone mass disease in a patient known or suspected to be in need of such treatment or prevention comprising administering to the patient known or suspected to be in need of such treatment or prevention a therapeutically effective amount of an agent that lowers the level of serum serotonin.

In certain embodiments, the agent is a TPH1 inhibitor or a serotonin receptor antagonist. In preferred embodiments, the agent is a TPH1 inhibitor that does not cross the blood brain barrier. In other embodiments, the agent is a TPH1 inhibitor that does not significantly inhibit TPH2.

In certain embodiments, the agent is a TPH1 inhibitor selected from the group consisting of:

(a)
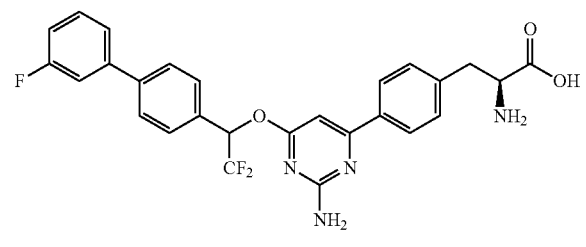
LP-533401

(b)
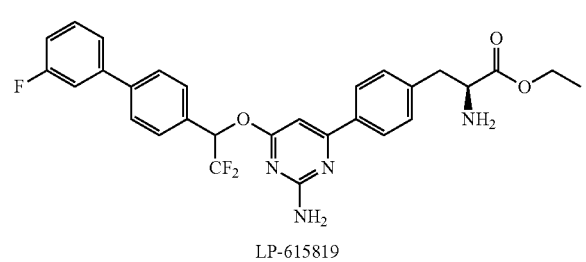
LP-615819

(c)
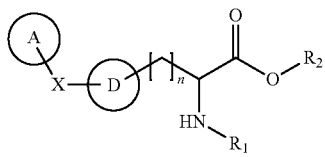

and pharmaceutically acceptable salts and solvates thereof, wherein: A is optionally substituted cycloalkyl, aryl, or heterocycle; X is a bond (i.e., A is directly bound to D), —O—, —S—, —C(O)—, —C(R4)═, ═C($R_4$)—, —C($R_3R_4$)—, —C($R_4$)═C($R_4$)—, —C≡C—, —N($R_5$)—, —N($R_5$)C(O)N($R_5$)—, —C($R_3R_4$)N($R_5$)—, —N($R_5$)C($R_3R_4$)—, —ONC($R_3$)—, —C($R_3$)NO—, —C($R_3R_4$)O—, —OC($R_3R_4$)—, —S($O_2$)—, —S($O_2$)N($R_5$)—, N($R_5$)S($O_2$)—, —($R_3R_4$)S($O_2$)—, or —S($O_2$)C($R_3R_4$)—; D is optionally substituted aryl or heterocycle; $R_1$ is hydrogen or optionally substituted alkyl, alkyl-aryl, alkyl-heterocycle, aryl, or heterocycle; $R_2$ is hydrogen or optionally substituted alkyl, alkyl-aryl, alkyl-heterocycle, aryl, or heterocycle; $R_3$ is hydrogen, alkoxy, amino, cyano, halogen, hydroxyl, or optionally substituted alkyl; $R_4$ is hydrogen, alkoxy, amino, cyano, halogen, hydroxyl, or optionally substituted alkyl or aryl; each $R_5$ is independently hydrogen or optionally substituted alkyl or aryl; and n is 0-3;

(d)
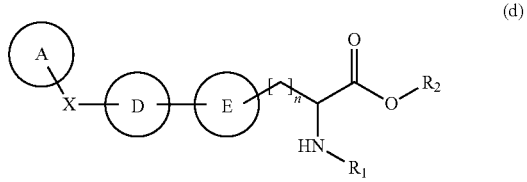

and pharmaceutically acceptable salts and solvates thereof, wherein: A is optionally substituted cycloalkyl, aryl, or heterocycle; X is a bond (i.e., A is directly bound to D), —O—, —S—, —C(O)—, —C(R4)═, ═C($R_4$)—, —C($R_3R_4$)—, —C($R_4$)═C($R_4$)—, —C≡C—, —N($R_5$)—, —N($R_5$)C(O)N($R_5$)—, —C($R_3R_4$)N($R_5$)—, —N($R_5$)C($R_3R_4$)—, —ONC($R_3$)—, —C($R_3$)NO—, —C($R_3R_4$)O—, —OC($R_3R_4$)—, —S($O_2$)—, —S($O_2$)N($R_5$)—, N($R_5$)S($O_2$)—, —C($R_3R_4$)S($O_2$)—, or —S($O_2$)C($R_3R_4$)—; D is optionally substituted aryl or heterocycle; E is optionally substituted aryl or heterocycle; $R_1$ is hydrogen or optionally substituted alkyl, alkyl-aryl, alkyl-heterocycle, aryl, or heterocycle; $R_2$ is hydrogen or optionally substituted alkyl, alkyl-aryl, alkyl-heterocycle, aryl, or heterocycle; $R_3$ is hydrogen, alkoxy, amino, cyano, halogen, hydroxyl, or optionally substituted alkyl; $R_4$ is hydrogen, alkoxy, amino, cyano, halogen, hydroxyl, or optionally substituted alkyl or aryl; each $R_5$ is independently hydrogen or optionally substituted alkyl or aryl; and n is 0-3;

(e)
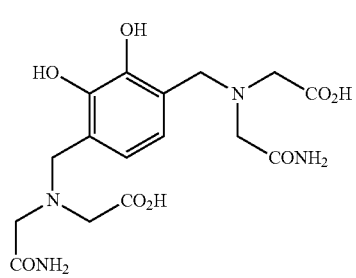 [SMILES: NC(=O)CN(CC(=O)O)Cc1ccc(CN(CC(N)=O)CC(=O)O)c(O)c1O]

(f)
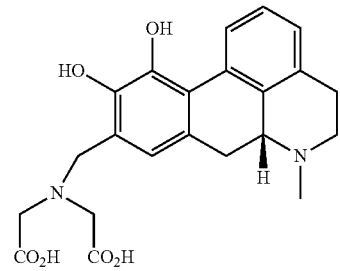

(g)
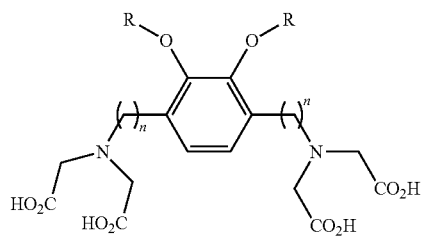

where R is hydrogen or lower alkyl; and
n is 1, 2, or 3;

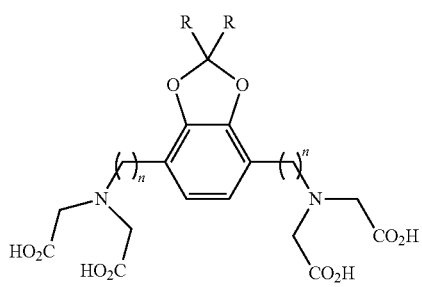
(h)

where R is hydrogen or lower alkyl; and
n is 1, 2, or 3;

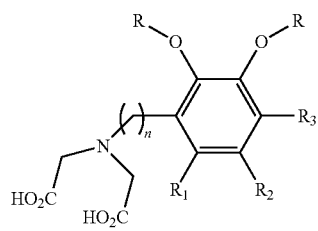
(i)

where R is hydrogen or lower alkyl;
$R_1$, $R_2$, and $R_3$, are independently:
    hydrogen;
    halogen;
    lower alkyl;
    alkoxy; or
    amino; and
n is 1, 2, or 3;

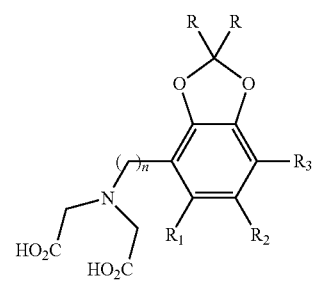
(j)

where R is hydrogen or lower alkyl;
$R_1$, $R_2$, and $R_3$, are independently:
    hydrogen;
    halogen;
    lower alkyl;
    alkoxy; or
    amino; and
n is 1, 2, or 3;

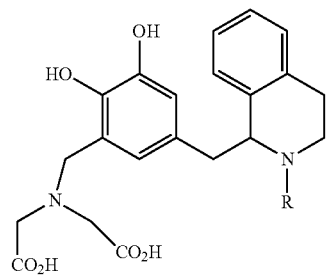
(k)

where R is hydrogen, lower alkyl, or cycloalkyl;

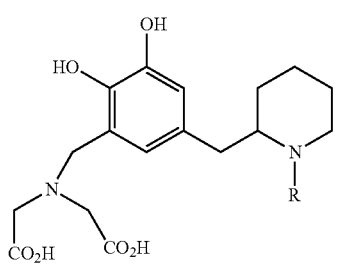
(l)

where R is hydrogen, lower alkyl, or cycloalkyl;

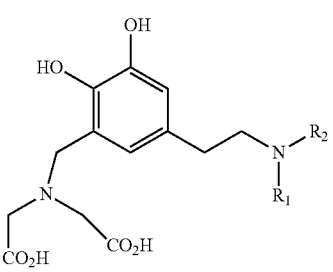
(m)

where $R_1$ and $R_2$, are independently hydrogen, lower alkyl, or cycloalkyl;

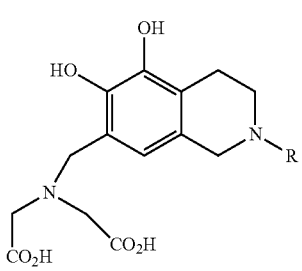
(n)

where R is hydrogen, lower alkyl, or cycloalkyl;

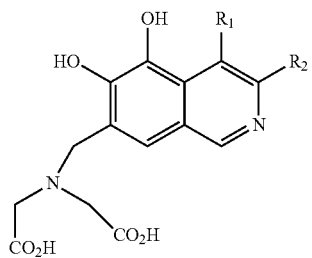

(o)

where $R_1$ and $R_2$ are independently hydrogen, lower alkyl, cycloalkyl, F, Cl, or OH;

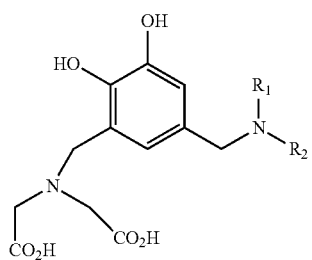

(p)

where $R_1$ and $R_2$ are independently hydrogen, lower alkyl, or cycloalkyl;
including any racemic mixtures and individual enantiomers of the agents, esters, and salts of the agents with a physiologically acceptable acid.

The present invention provides pharmaceutical compositions comprising a therapeutically effective amount of a TPH1 inhibitor disclosed above and at least one pharmaceutically acceptable excipient.

In certain embodiments, the agent is a serotonin receptor antagonist, preferably an HT1B, HT2A or HT2B serotonin receptor antagonist, and most preferably an HT1B serotonin receptor antagonist. In certain embodiments, the serotonin receptor antagonist is an HT1B serotonin receptor antagonist listed in Table 3.

The present invention also provides methods where the patient is administered both a TPH1 inhibitor and a serotonin receptor antagonist. The TPH1 inhibitor and the serotonin receptor antagonist may be administered together in a single pharmaceutical composition.

In certain embodiments of the present invention, the low bone mass disease is osteoporosis, osteoporosis pseudoglioma syndrome (OPPG), osteopenia, osteomalacia, renal osteodystrophy, faulty bone formation or resorption, Paget's disease, fractures and broken bones, or bone metastasis. Preferably, the low bone mass disease is osteoporosis.

In other embodiments of the invention, the patient is being treated with an SSRI, a bisphosphonate, or a beta blocker in addition to an agent that lowers the level of serum serotonin. In some embodiments, the methods of the present invention also comprise administering an SSRI, a bisphosphonate, or a beta blocker in addition to an agent that lowers the level of serum serotonin.

In certain embodiments, the patient is being treated with an agent that increases the level of serum serotonin (e.g., an SSRI) or the patient has a condition associated with an increased level of serum serotonin. In certain embodiments, the method also comprises treating the patient with an agent that increases the level of serum serotonin (e.g., an SSRI).

In certain embodiments, the patient's level of serum serotonin is measured prior to administering the agent that lowers the level of serum serotonin. In other embodiments, the patient's level of serum serotonin is measured after administering the agent that lowers the level of serum serotonin. In some embodiments, the patient's level of serum serotonin is measured before and after administering the agent that lowers the level of serum serotonin.

In certain embodiments, the agent that lowers the level of serum serotonin is repeatedly administered to the patient and the patient's level of serum serotonin is measured until the patient's level of serum serotonin is reduced by at least about 10% compared to the level measured prior to the first administration of the agent that lowers the level of serum serotonin.

In certain embodiments, the patient has been identified as having a serum serotonin level that is more than 25% higher than the normal level of serum serotonin.

In certain embodiments, the patient is administered an agent that increases brain derived serotonin in addition to the agent that lowers the level of serum serotonin. In preferred embodiments, the agent that increases brain derived serotonin is an agent that increases TPH2 activity.

In certain embodiments, the patient's level of serum serotonin is lowered by at least about 10% compared to the level before administering the agent that lowers the level of serum serotonin.

In certain embodiments, the agent that lowers the level of serum serotonin is administered in an amount of from about 1 mg/day to about 2 g/day.

The present invention provides a pharmaceutical composition comprising an amount of an agent that lowers the level of serum serotonin in a patient to whom the composition is administered by at least about 10%. In preferred embodiments, the agent is a TPH1 inhibitor or a serotonin receptor antagonist.

The present invention provides a pharmaceutical composition comprising a therapeutically effective amount of an agent that lowers the level of serum serotonin in a patient to whom the composition is administered. In preferred embodiments, the agent is a TPH1 inhibitor or a serotonin receptor antagonist.

In some embodiments, the pharmaceutical composition comprises an agent that lowers the level of serum serotonin and an agent that raises the level of brain-derived serotonin.

In some embodiments, the pharmaceutical composition comprises an agent that lowers the level of serum serotonin and an SSRI, a bisphosphonate, or a beta blocker. In preferred embodiments, the agent is a TPH1 inhibitor or a serotonin receptor antagonist. In certain embodiments, the serotonin receptor antagonist is an HT1B, HT2A or HT2B serotonin receptor antagonist, preferably an HT1B serotonin receptor antagonist.

In certain embodiments, the pharmaceutical composition comprises both a TPH1 inhibitor and a serotonin receptor antagonist.

The present invention also provides a method for identifying a subject at risk of developing a disease associated with low bone mass, comprising,
a) determining the level of serum serotonin in biological samples taken from the patient and from a normal subject,
b) concluding that the patient is at risk of developing the disease if the level of serum serotonin in the sample from the patient is elevated by at least about 25% above the serum serotonin level in the sample from the normal subject.

In certain embodiments, the method comprises, after step (b), administering to the patient at risk of developing the disease an agent that lowers the level of serum serotonin.

DETAILED DESCRIPTION OF THE INVENTION

Figure 1:
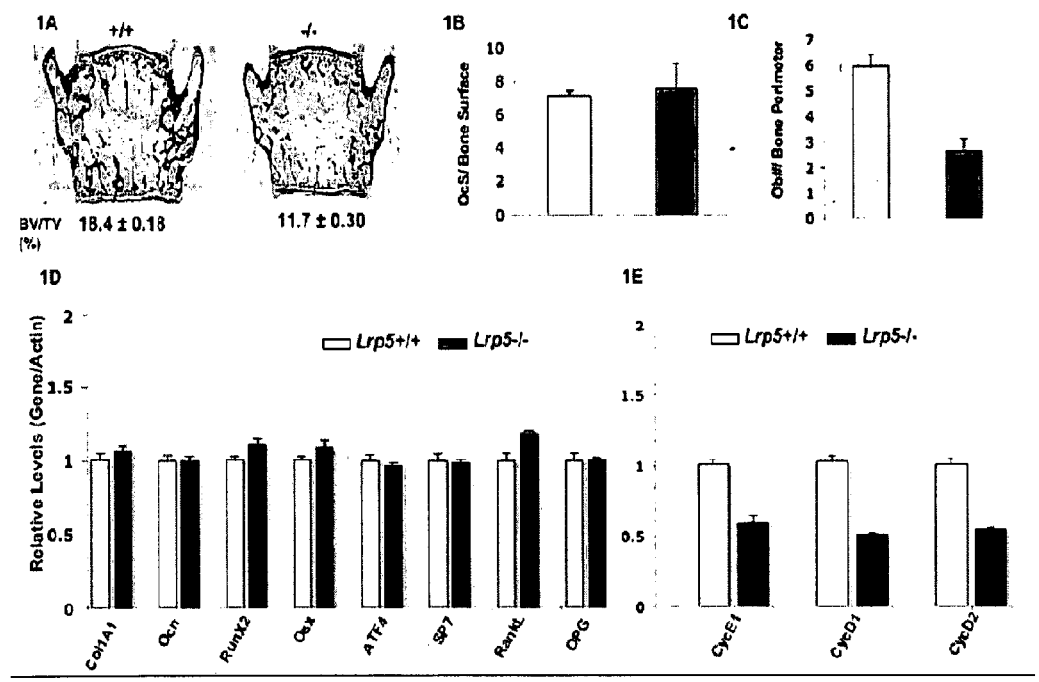
FIG. 1. Lrp5−/− mice have low bone mass (A) with no change in osteoclast surface (B) but decreased osteoblast numbers (C). Real-time PCR analysis of Lrp5−/− molecular signature. Lrp5−/− osteoblasts do not show changes in osteoblast-specific gene expression (D) but have decreased Cyclin gene expression (E).

Diseases associated with low bone density ("low bone mass diseases"), as used herein, refers to any bone disease or state that results in or is characterized by loss of health or integrity to bone due to abnormally low bone mass, and includes, but is not limited to, osteoporosis, osteoporosis pseudoglioma syndrome (OPPG), osteopenia, osteomalacia, renal osteodystrophy, faulty bone formation or resorption, Paget's disease, fractures and broken bones, and bone metastasis. More particularly, bone diseases that can be treated and/or prevented in accordance with the present invention include bone diseases characterized by a decreased bone mass relative to that of corresponding non-diseased bone.

Diseases associated with high bone density, as used herein, refers to any bone disease or state which results in or is characterized by an abnormally high bone density, such as high bone mass syndrome.

Prevention of bone disease means actively intervening as described herein prior to overt disease onset to prevent the disease or minimize the extent of the disease or slow its course of development.

Treatment of bone disease means actively intervening after onset to slow down, ameliorate symptoms of, or reverse the disease or situation in a patient who is known or suspected of having a bone disease, particularly a low bone mass disease. More specifically, treating refers to a method that modulates bone mass to more closely resemble that of corresponding non-diseased bone (that is a corresponding bone of the same type, e.g., long, vertebral, etc.) in a non-diseased state.

Unless otherwise indicated, a "therapeutically effective amount" of a compound is an amount that provides a therapeutic benefit in the treatment or management of a disease or condition, delays or minimizes one or more symptoms associated with the disease or condition, or enhances the therapeutic efficacy of another therapeutic agent. An agent is said to be administered in a "therapeutically effective amount" if the amount administered results in a desired change in the physiology of a recipient mammal, (e.g., increases bone mass in a mammal having or at risk of developing a low bone mass disease) compared to pre-treatment levels, or decreases bone mass in an animal having or at risk of developing a high bone mass disease (compared to pre-treatment levels). That is, drug therapy results in treatment, i.e., modulates bone mass to more closely resemble that of corresponding non-diseased bone (such as a corresponding bone of the same type, e.g., long, vertebral, etc.) in a non-diseased state. For example, a therapeutically effective amount of a TPH1 inhibitor or agent that reduces serotonin synthesis includes an amount that reduce serum serotonin levels to a level that is at least about 10% less than the level before drug treatment.

A therapeutic agent such as a TPH1 inhibitor significantly reduces serum serotonin if the post-treatment level of serotonin is reduced at least about 10% or more compared to pre-treatment levels. A patient is at risk of developing a low bone mass disease if his or her serum serotonin levels are elevated by about 25% or more compared to serum serotonin levels in normal subjects. Alternatively, A patient is at risk of developing a high bone mass disease if his or her serum serotonin levels are reduced by about 25% or more compared to serum serotonin levels in normal subjects.

A "patient" is a mammal, preferably a human, but can also be companion animals such as dogs or cats, or farm animals such as horses, cattle, pigs, or sheep.

A patient in need of treatment or prevention for a bone disease includes a patient known or suspected of having or being at risk of developing a bone disease. Such a patient in need of treatment could be, e.g., a person known to have osteoporosis. A patient at risk of developing a bone disease could include the elderly, post-menopausal women, patients being treated with glucocorticoids, patients being treated with SSRIs, and patients having bone density outside the normal range. Other persons in need of treatment or prevention by the methods of the present invention include persons who are known to be in need of therapy to decrease serum serotonin levels in order to treat or prevent a bone disease, e.g., osteoporosis. Such persons might include persons who have been identified as having a serum serotonin level that is about 25% or more above that of serum serotonin levels in normal subjects.

A patient in need of treatment or prevention for a bone disease by the methods of the present invention does not include a patient being treated with a TPH1 inhibitor, a serotonin HT1B antagonist, or other agent that decreases serum serotonin levels where the patient is being treated with the TPH1 inhibitor, serotonin HT1B antagonist, or other agent that decreases serum serotonin levels for a purpose other than to treat a bone disease. Thus, patient in need of treatment or prevention for a bone disease by the methods of the present invention does not include a patient being treated with a TPH1 inhibitor for the purpose of treating chemotherapy-induced emesis or gastrointestinal disorders such as irritable bowel syndrome.

A "small organic molecule" is meant organic compounds of molecular weight of more than 100 and less than about 2,500 daltons, and preferably less than 500 daltons.

A "TPH1 inhibitor" is a substance that reduces the amount of 5-hydroxytryptophan produced from tryptophan by TPH1 by at least about 10% in a suitable assay, as compared to the amount of 5-hydroxytryptophan produced from tryptophan by TPH1 in the assay in the absence of the substance. Assays for determining the level of TPH1 inhibition of an agent are described in International Patent Publication WO 2007/089335.

A "TPH2 inhibitor" is a substance that reduces the amount of 5-hydroxytryptophan produced from tryptophan by TPH2 by at least about 10% in a suitable assay, as compared to the amount of 5-hydroxytryptophan produced from tryptophan by TPH2 in the assay in the absence of the substance.

Techniques for measuring bone mass include those techniques well known to those of skill in the art including, but not limited to, skeletal X-rays, which show the lucent level of bone (the lower the lucent level, the higher the bone mass); classical bone histology (e.g., bone volume, number and aspects of trabiculi/trabiculations, numbers of osteoblasts relative to controls and/or relative to osteoclasts); and dual energy X-ray absorptiometry (DEXA) (Levis & Altman, 1998, Arthritis and Rheumatism, 41:577-587) which measures bone mass and is commonly used in osteoporosis. BFR means bone formation rate. Any method known in the art can be used to diagnose a person at risk of developing high or low bone mass diseases, or to determine the efficacy of drug therapy.

Selective serotonin reuptake inhibitors (SSRIs) mean a class of antidepressants used in the treatment of depression, anxiety disorders, and some personality disorders. They are also typically effective and used in treating premature ejaculation problems. SSRIs increase the extracellular level of the neurotransmitter serotonin by inhibiting its reuptake into the presynaptic cell, increasing the level of serotonin available to bind to the postsynaptic receptor. They have varying degrees of selectivity for the other monoamine transporters, having little binding affinity for the noradrenaline and dopamine transporters. The first class of psychotropic drugs to be rationally designed, SSRIs are the most widely prescribed antidepressants in many countries. SSRIs include: citalopram (CELEXA®, CIPRAMIL®, EMOCAL®, SEPRAM®, SEROPRAM®); escitalopram oxalate (LEXAPRO®, CIPRALEX®, ESERTIA®); fluoxetine (PROZAC®, FONTEX®, SEROMEX®, SERONIL®, SARAFEM®, FLUCTIN® (EUR), FLUOX® (NZ)); fluvoxamine maleate (LUVOX®, FAVERIN®); paroxetine (PAXIL®, SEROXAT®, AROPAX®, DEROXAT®, REXETIN®, XETANOR®, PAROXAT®); sertraline (ZOLOFT®, LUSTRAL®, SERLAIN®), and dapoxetine (no known trade name).

Lrp5 Regulates Bone Development Through More Than One Mechanism

The extreme conservation of gene function between mouse and human when it comes to skeletal biology explains why skeletal biology, and especially the study of bone remodeling and homeostasis, has been profoundly influenced by mouse and human genetic studies. Although gene inactivation experiments in mice or molecular cloning of disease genes in humans were designed initially to identify genes important during embryonic development, results of these studies went further than this initial goal by also shedding new light on the molecular bases of skeletal biology after birth. Among the genes identified either through gene deletion experiments or through human genetic studies that turned out to be important for the maintenance of bone mass in adults, one can cite the vitamin D receptor, Interleukin 6, Estrogen receptor α and LDL receptor related protein 5 (Lrp5) (Gong et al., 2001, Cell 107: 513-523; Boyden et al., 2002, N. Engl. J. Med. 346: 1513-1521; Yoshizawa et al., 1997, Nat. Genet. 16: 391-396; Ohshima et al., 1998, Proc. Natl. Acad. Sci. USA 95:8222822-6; Windahl et al., 2002, Trends Endocrinol. Metab. 13:195-200).

The identification of Lrp5 as a regulator of post-natal bone formation is one of the most vivid examples of how developmental studies can profoundly affect the understanding of physiology because this receptor is expressed during development but its function only becomes apparent post-natally. Indeed, loss-of-function mutations in Lrp5 cause osteoporosis pseudoglioma syndrome (OPPG) in humans, a pediatric disease, and gain-of-function mutations in Lrp5 cause high bone mass, a phenotype most often appearing only in adolescents and persisting into adulthood (Gong et al., 2001, Cell 107: 513-523; Boyden et al., 2002, N. Engl. J. Med. 346: 1513-1521; Johnson et al., 1997, Am. J. Hum. Genet. 60:1326-1332). Likewise, skeletogenesis is normal in Lrp5−/− mice and their low bone mass phenotype only develops post-natally (Kato et al., 2002, J. Cell. Biol. 157: 303-314).

The LDL receptor related protein 5 (LRP5) is required for normal bone mass, and a low bone mass phenotype is caused by Lrp5 inactivation in humans and mice (Gong et al., 2001, Cell 107:513-523; Kato et al., 2002, J. Cell. Biol. 157: 303-314). Lrp5−/− mice have low bone mass with no change in osteoclast surface but decreased osteoblast numbers. Realtime PCR analysis of Lrp5−/− molecular signature shows that Lrp5−/− osteoblasts do not show changes in osteoblast-specific gene expression but have decreased expression of cyclin genes (FIG. 1). Lrp5 and its closest relative Lrp6 are the vertebrate homologues of the *Drosophila* gene arrow that encodes a surface receptor functioning as a co-receptor for Wingless, the *drosophila* homologue of the Wnt proteins (Wehrli et al., 2000, Nature 407:527-530; Tamai et al., 2000, Nature 407:530-535). In vertebrate cells, Wnt signaling is mainly mediated by β-catenin. Upon binding of a Wnt ligand to its receptor, β-catenin is translocated to the nucleus where it cooperates with Lef/Tcf transcription factors to activate gene expression (Logan et al., 2004, Annu. Rev. Cell Dev. Biol. 20:781-810; Mao et al., 2001, Mol. Cell, 7:801-809). According to this canonical model, co-transfection of Lrp5 increases the ability of Wnt proteins to enhance the activity of a Tcf-dependent promoter such as the TopFlash promoter (Gong et al., 2001, Cell 107: 513-523; Boyden et al., 2002, N. Engl. J. Med. 346:1513-1521; Mao et al., 2001, Mol. Cell, 7:801-809). Together, the homology of sequence between arrow and Lrp5 and the ability of Lrp5 to favor Wnt signaling through its canonical pathway have led to a model whereby Wnt signaling would regulate bone mass post natally and during adulthood by regulating osteoblast proliferation and function. There is no reason to question the notion that Lrp5 may be a co-receptor for Wnts and that Wnt signaling is involved in the regulation of bone formation (Glass et al., 2005, Dev. Cell 8:751-764; Holmen et al., 2005, J. Biol. Chem. 280:21162-21168; Day et al., 2005, Dev. Cell, 8:739-750; Hu et al., 2005, Development 132:49-60). Nevertheless, there may be additional mechanisms that explain the bone abnormalities observed in either Lrp5 loss- or gain-of-function models.

Lrp5 Regulates Bone Mass in the Periphery Through Serotonin

TPH1 encodes the first enzyme in the biochemical pathway resulting in serotonin synthesis outside the central nervous system. It is viewed as a cell-specific gene mostly expressed in the enterochromaffin cells of the duodenum (Gershon and Tack, Gastroenterology, 2007, 132:397-414), By contrast, serotonin synthesis in the brain relies on TPH2, which is encoded by a different gene expressed in the central nervous system (CNS).

In an effort to elucidate the molecular mechanisms whereby Lrp5 inactivation affects bone formation, a microarray analysis in WT and Lrp5-/- bones was performed. Tryptophan hydroxylase 1 (TPH1) was identified as the gene most highly over expressed in Lrp5-/- bones having low bone mass disease. This result was surprising since it is the opposite of what would be expected given the role of serotonin in the brain, where it increases bone mass. Remarkably, TPH1 expression was normal in mice lacking β-catenin in osteoblasts only (Glass et al., 2005, Dev. Cell 8:751-764).

Figure 7:
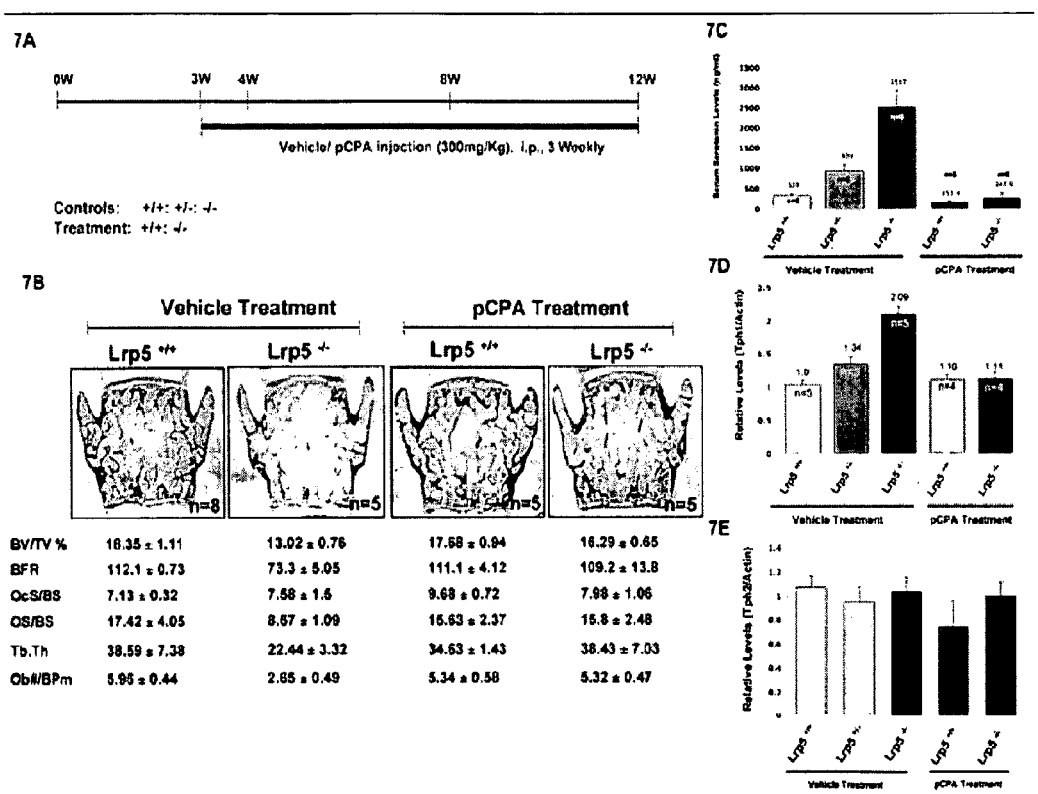
FIG. 7. Tryptophan hydroxylase inhibitor (pCPA) treatment normalizes serum serotonin levels and corrects bone abnormalities observed in Lrp5−/− mice. Treatment regimen for the pCPA treatment (A), histomorphometric analysis of bone phenotype (B), serum serotonin levels (C), gut Tph1 expression levels (D), brain Tph2 expression upon vehicle and pCPA treatment, (E) brain Tph2 expression upon vehicle and pCPA treatment.

It was shown that TPH1 is overexpressed not only in bone, but also in the duodenum in Lrp5-/- mice, where TPH1 expression is more than 1300-fold higher than in osteoblasts. It was further discovered that serum serotonin levels are normal in newborn Lrp5-/- mice but increase steadily with age as their bone phenotype develops. This is consistent with the fact that the low bone mass phenotype in Lrp5-/- mice is not present at birth but appears later during development. Further discoveries showed that treating Lrp5-/- mice with an inhibitor of serotonin synthesis called pCPA corrects their low bone phenotype (FIG. 7). Finally, it was discovered that TPH1 expression is increased in aging animals, i.e., when bone mass is well-known to decrease. Based on these and additional data described below, it can be conclude that LRP5, through yet unknown mechanisms, is a negative regulator of serotonin synthesis in the duodenum, and that increasing serum serotonin signaling negatively impacts osteoblast proliferation and function.

Serotonin, a Multifaceted Molecule

Serotonin (5-hydroxytryptamine, 5-HT) is a biogenic amine that functions both as a neurotransmitter in the mammalian central nervous system and as a hormone in the periphery, where most of it is produced (Gershon et al., 1990, Neuropsychopharmacology, 3:385-395). Serotonin is generated through an enzymatic cascade in which L-tryptophan is converted into L-5-hydroxytryptophan by an enzyme called tryptophan hydroxylase (TPH). This intermediate product is then converted to serotonin by an aromatic L-amino acid decarboxylase. There are two TPH encoding genes, TPH1 and TPH2, which are 71% identical in amino acid sequence and about 90% similar in the catalytic domain. While TPH1 controls serotonin synthesis in the periphery, TPH2 is responsible for serotonin synthesis in the brain (Walther et al., 2003, Science 299:76). Given that serotonin cannot cross the blood-brain barrier, these two genes are therefore solely responsible for regulating the level of this molecule in the periphery and in the brain, respectively. As a consequence, designing TPH1 inhibiting compounds that cannot cross the blood brain barrier is one of the ways to achieve selective inhibition of TPH1 in the periphery and decrease serotonin levels in this physiologic compartment.

TPH1 is expressed almost exclusively in cells of the duodenum, and it is responsible for the synthesis of peripheral serotonin, which represents 95% of total serotonin (Gershon & Tack, 2007, 132:397-414). TPH1 expression in any tissues other than duodenum is at least 100-1000 fold lower. Thus, TPH1 can be viewed as a duodenum-specific gene and peripheral serotonin production as a duodenum-specific process.

Besides its role as a neuromediator, and because of its abundance in the general circulation, serotonin has been implicated in a variety of developmental and physiological processes in peripheral tissues, including heart development, gastrointestinal movement, liver regeneration and mammary gland development (Lesurtel et al., 2006, Science, 312:104-107; Matsuda et al., 2004, Dev. Cell, 6:193-203; Nebigil et al., 2000, Proc. Natl. Acad. Sci. USA 97:9508-9513). To carry out its functions, serotonin can bind to at least 14 receptors, most of them being G-protein coupled receptors (GPCRs). One or several serotonin receptors are present in most cell types, including osteoblasts (Westbroek et al., 2001, J. Biol. Chem. 276:28961-28968).

Type 1 Collagen, Osteocalcin, Regulatory Genes Affecting Osteoblast Differentiation and/or Extracellular Matrix Protein Synthesis (Runx2 and Osterix and Atf4) and Osteoclast Differentiation (RankL and Osteoprotegrin) are Normal in Lrp5-Deficient Mice Lrp5-/- mice are indistinguishable by all accounts from WT mice at birth, but afterward progressively develop a significant low bone mass phenotype (Kato et al., 2002, J. Cell. Biol. 157: 303-314). Histological and histomorphometric analyses established that this low bone mass phenotype is due to a decrease in bone formation while bone resorption is unaffected. Importantly, osteoblast differentiation is not affected in the mutant mice while osteoblast proliferation is decreased two fold in the absence of Lrp5. See FIG. 1, which shows that Lrp5-/- mice have low bone mass (A) with no change in osteoclast surface (B) but have decreased osteoblast numbers (C).

Real-Time PCR Analysis of Lrp5-/- Molecular Signature.

To delineate the molecular signature of the disruption of Lrp5 signaling, the expression of multiple genes characterizing either the osteoblast lineage or determining cell proliferation was studied using Lrp5-/- mice (Kato et al., 2002, J. Cell. Biol. 157: 303-314). The expression of genes particularly relevant to bone formation was first analyzed. Expression of type I collagen and Osteocalcin, two genes highly expressed in osteoblasts, is normal in Lrp5−/− bones (data not shown). This finding is important as it establishes that the bone phenotype of the Lrp5−/− mice is not caused by a defect in type I collagen synthesis, the main constituent of the bone extracellular matrix (ECM). Expression of regulatory genes affecting osteoblast differentiation and/or extracellular matrix protein synthesis was also studied. Expression of Runx2 and Osterix and Atf4, the three known osteoblast-specific transcription factors, was unaltered in Lrp5−/− bones (FIG. 1D). Likewise, expression of RankL and Osteoprotegerin (OPG), two regulators of osteoclast differentiation expressed by osteoblasts is unaffected by Lrp5 deletion (FIG. 1D). This latter feature distinguishes Lrp5−/− from β-catenin osteoblast-specific deficient ((βcatob−/−) bones (Glass et al., 2005, Dev. Cell 8:751-764; Holmen et al., 2005, J. Biol. Chem. 280:21162-21168).

Given the decrease in osteoblast proliferation characterizing Lrp5−/− bones, the expression of marker genes of cell cycle progression was also studied. Expression of Cyclin D1, D2 and E1, three genes necessary for the transition from the G1 to S phase of the cell cycle, was decreased in the Lrp5−/− bones (FIG. 1E). Based on these results, it appears that at the molecular level the low bone mass phenotype caused by the absence of Lrp5 is purely a cell proliferation defect while expression of type I collagen, the main protein constituent of the bone extracellular matrix (ECM), and of all 3 known osteoblast-specific transcription factors is normal.

Low Bone Phenotype in Lrp5−/− Mice is not Due to Abnormal Wnt Signaling

Figure 2:
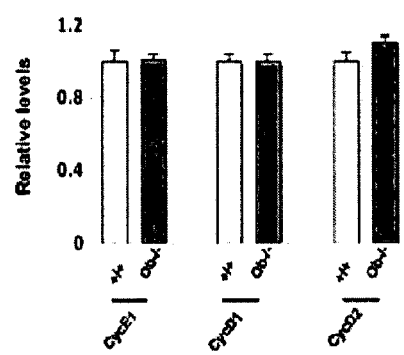
FIG. 2. Real-time PCR analysis of cell cycle marker genes in β-cat$_{ob}$−/− bones (ob−/−).

Given the sequence homology and convincing experimental arguments suggesting that Lrp5 could be a co-receptor for Wnt and may be part of the Wnt canonical signaling pathway, whether the bone phenotype of Lrp5−/− mice was due to abnormal Wnt signaling was investigated. To that end, mice lacking β-catenin in osteoblasts only were analyzed (Glass et al., 2005, Dev. Cell 8:751-764). It had been shown earlier that mice lacking β-catenin only in osteoblasts developed a low bone mass phenotype and that this phenotype was caused by a totally different mechanism than the one operating in the Lrp5−/− mice. Indeed, β-cat$_{ob}$−/− mice have a normal number of osteoblasts, an increase of the number of osteoclasts and an increase in elimination of deoxypyridinoline, abnormalities that are secondary to a decrease in OPG expression (Glass et al., 2005, Dev. Cell 8:751-764). In addition, unlike in Lrp5−/− bones, expression of the cell cycle markers Cyclin D1, D2 and E1 was normal in the in β-cat$_{ob}$−/− bones (FIG. 2). Thus, the cellular and molecular bases of the β-cat$_{ob}$−/− and Lrp5−/− mice bone phenotype appear to be quite different. Although these unexpected results do not rule out that Lrp5 could act as a Wnt co-receptor, there was still a possibility that other mechanisms could explain how the loss of Lrp5 could affect bone formation so specifically. To that end, a microarray analysis looking for genes abnormally expressed in Lrp5−/− compared to WT bones was performed.

TPH1 is Overexpressed in Bone and Duodenum in Lrp5−/− Mice

Figure 3:
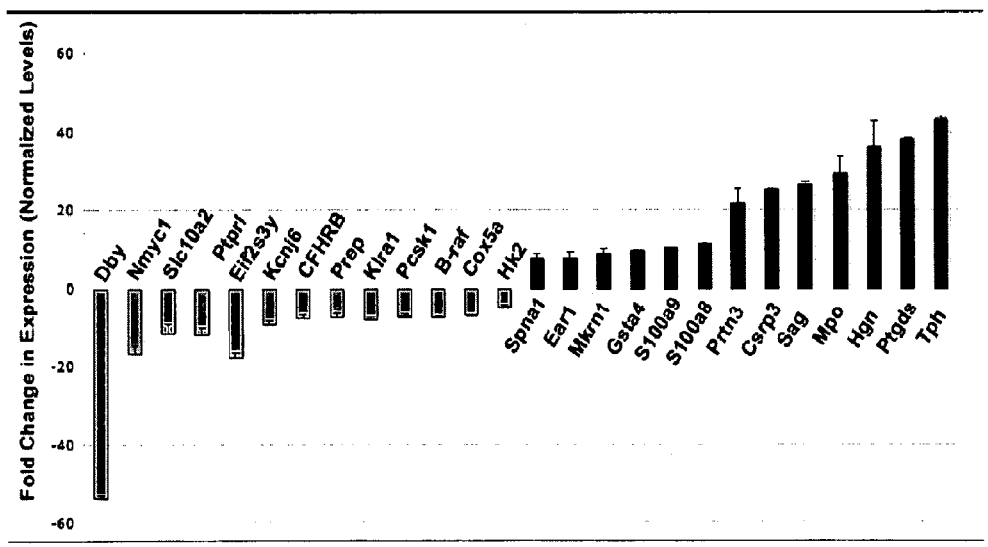
FIG. 3. Microarray analysis of Lrp5−/− bones reveals an increased expression of Tryptophan hydroxylase 1 (Tph1) gene expression compared to wt bones. Green and red bars indicate a decrease and an increase in gene expression, respectively. Genes including and to the left of Hk2 showed decreased expression while genes including and to the right of Spna1 showed increased expression.

A microarray analysis of Lrp5−/− bones surprisingly showed that one of the genes most highly over expressed was TPH1 (FIG. 3). It is important to emphasize that TPH1 expression is normal in β-cat$_{ob}$−/− bones and osteoblasts, further underscoring the molecular differences that exist between these two mutant mouse strains. Given the rather confined pattern of expression of TPH1 in WT mice, where it is restricted to the duodenum, its overexpression in Lrp5−/− bones was surprising and raised the question whether it was an osteoblast-specific feature.

Figure 4:
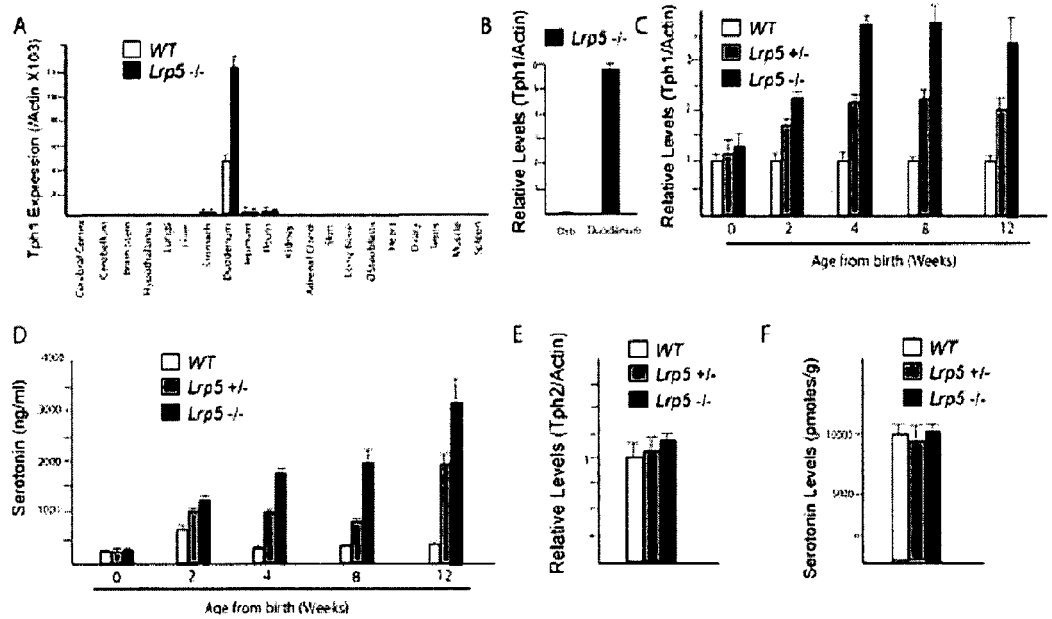
FIG. 4. Tph1 expression is increased in the duodenum of Lrp5−/− mice (A). Tph1 expression is 1000 fold higher in duodenum than in bone in Lrp5−/− mice (B). Tph1 expression in duodenum (C) and serum serotonin levels (D) increase progressively with age in Lrp5−/− mice. Neither Tph2 expression nor serotonin levels are altered in the brain of Lrp5−/− mice (E and F).
Figure 5:
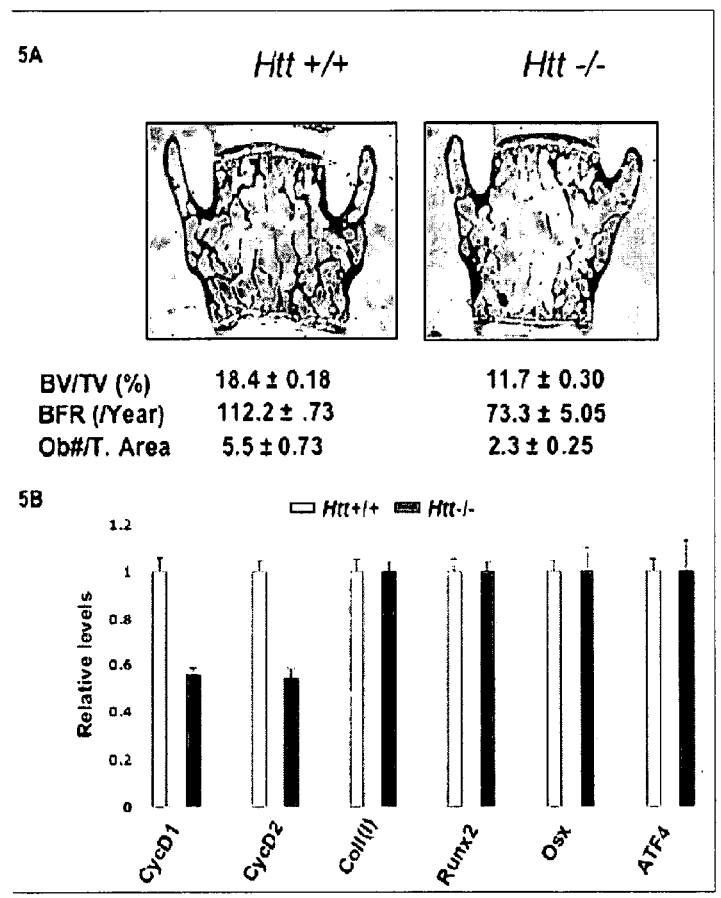
FIG. 5. 5Htt−/− mice have low bone mass and decreased osteoblast numbers (A). Real-time PCR analysis of gene expression in bone revealed a decreased expression of cyclins in 5Htt−/− mice while no changes in the expression of osteoblast differentiation markers or type I collagen genes can be detected (B).
Figure 6:
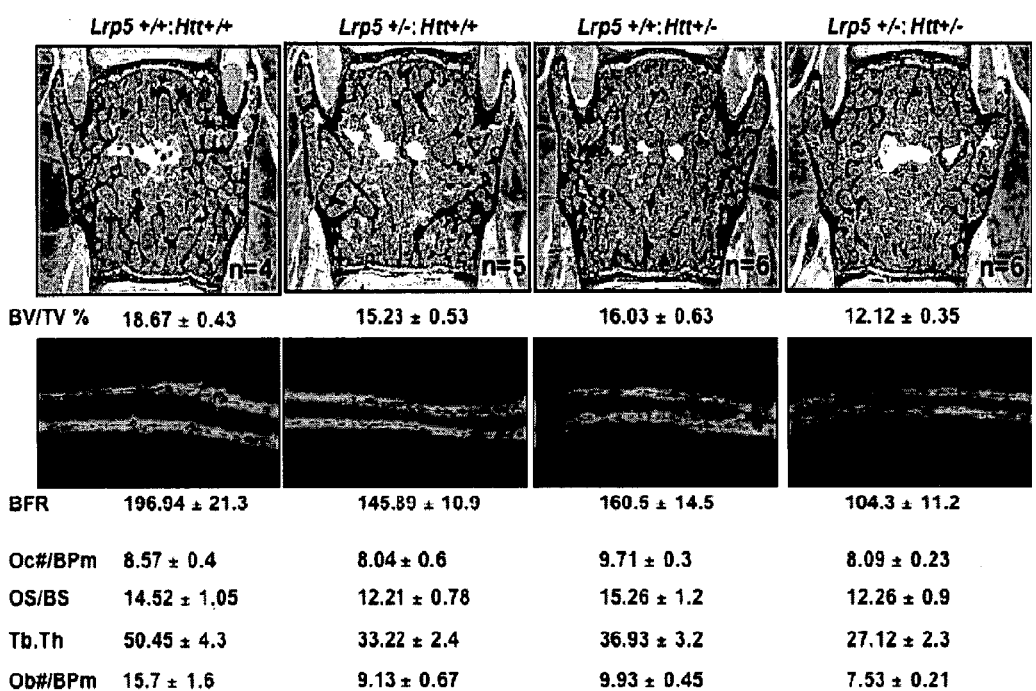
FIG. 6. Histologic and histomorphometric comparison of Lrp5/5Htt (Htt) compound mice. Lrp5+/−; Htt+/− double heterozygous mice have a more severe decrease in bone mass than the Lrp5+/− or 5Htt+/− single heterozygous mice. This is also true for the decrease in osteoblast numbers.

To answer this question, TPH1 expression in all tissues of WT and Lrp5−/− mice was analyzed by qPCR. It was found that TPH1 expression was also increased 3 fold in duodenum of Lrp5−/− compared to WT mice (FIG. 4A). However, TPH1 expression remained more than 1300 fold higher in duodenum than in osteoblasts in Lrp5−/− mice (FIG. 4B). These latter data suggested for the first time that the bone phenotype observed in Lrp5−/− mice may primarily have a gut origin. The increase in expression of TPH1 was also observed, albeit as expected to a lower level, in Lrp5+/− mice (FIG. 4C). This is an important observation since heterozygous Lrp5+/− mice also have a low bone mass phenotype. Importantly, in agreement with the absence of a bone phenotype in newborn Lrp5−/− mice, TPH1 expression was not elevated in newborn mice (FIG. 4C). The changes in TPH1 expression were reflected in increased serum serotonin levels in both Lrp5+/− and Lrp5−/− mice (FIG. 4D); which were absent at birth but present at 2, 4 and 8 weeks of age. Moreover these changes preceded the appearance of the bone phenotype in Lrp5−/− mice.

By contrast, the expression of TPH2 in the brain was not affected in Lrp5−/− mice and serotonin content in the brain was similar in WT and Lrp5−/− mice (FIGS. 4E and 4F). This observation is consistent with the fact that serotonin does not cross the blood brain barrier (Mann et al., 1992, Arch. Gen. Psychiatry, 49:442-446) and indicates that the link between Lrp5 function and serotonin biology has to be with peripheral serotonin.

Expression of the TPH1 gene was decreased compared to wild type (WT) in mice engineered with a mutation causing high bone mass in humans in one allele (Lrp5+/act duo) or both alleles (Lrp5 act duo) of the mouse Lrp5 gene specifically in cells of the duodenum. RNA was extracted from duodenum of one-month-old mice and expression of the TPH1 gene quantified by real-time PCR (FIG. 12).

TABLE 1

|  | WT | Lrp5+/act duo | Lrp5 act duo |
| --- | --- | --- | --- |
| Relative Tph1 expression | 1 | 0.77 ± 0.000 | 0.54 ± 0.005 |

Figure 12:
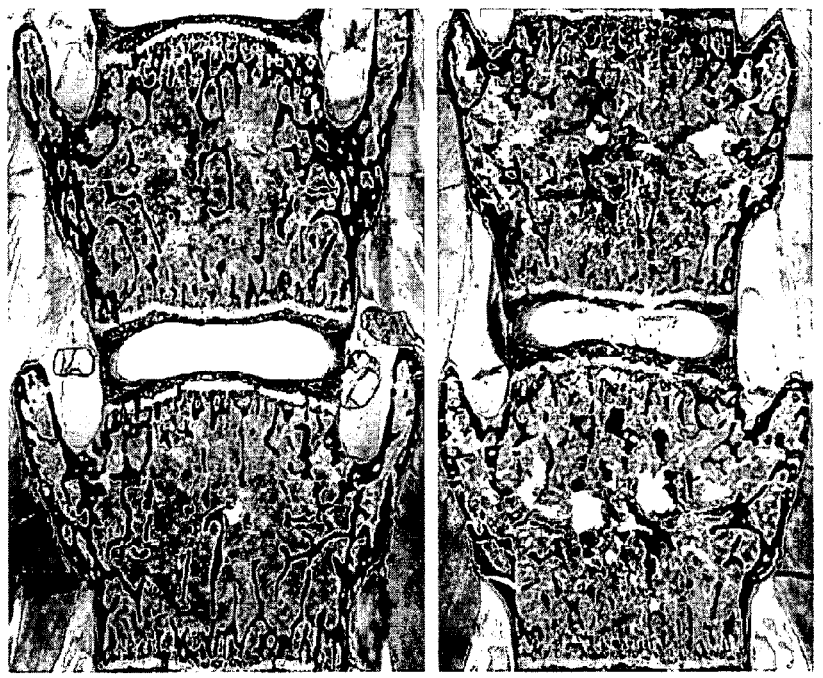
FIG. 12. Mice engineered to express in both alleles of their Lrp5 genes of their duodenal cells a mutation that in humans leads to high bone mass show a higher bone mass than wild-type (WT) mice. Vertebrae were embedded in plastic medium, sectioned at 5 micrometers and stained with the von Kossa/Van gieson reagent. The bone matrix was stained in black.

Mice engineered with a mutation causing high bone mass in human in the Lrp5 gene specifically in cells of the duodenum (Lrp5 act duo) show a higher bone mass than wild type mice (FIG. 12).

Taken together, the results of these analyses indicated that the increase in TPH expression caused by Lrp5 deficiency was restricted to TPH1 (and therefore to peripheral serotonin) and that it occurs both in osteoblasts and duodenal cells although its expression is at least 1300-fold higher in duodenum. This result raises two questions: is the increase in serum serotonin the cause of the Lrp5−/− mice bone phenotype and is this an endocrine effect mediated by the production of serotonin by duodenal cells and/or an autocrine effect related to the local production of serotonin by osteoblasts?

Lrp5−/− and 5Htt−/− Mice have Identical Bone Phenotypes

If the bone phenotype of the Lrp5−/− mice is secondary to an increase in the level of serum serotonin, then a mouse model characterized by an increase in serum serotonin should have not only the same histological bone phenotype as the Lrp5−/− mice but also the same molecular signature defined previously, i.e., decreased cyclin gene expression and normal type I collagen expression (FIG. 1). This is what was observed.

The Serotonin Synthesis Inhibitor (pCPA) Rescues the Bone Phenotype of Lrp5−/− Mice Consistent with the conclusion that the increase in serum serotonin level is responsible fully or partly for the bone phenotype of the Lrp5−/− mice is the discovery that pCPA, a serotonin synthesis inhibitor (Eldridge et al., 1981, Ann. Rev. Physiol. 43:121-135), prevented the appearance of the Lrp5−/− bone phenotype by decreasing serotonin production. WT and Lrp5−/− mice were treated with 300 mg/kg pCPA intraperitoneally three times per week, from 3 weeks to 12 weeks of age (FIG. 7A) and the changes in serum serotonin levels, TPH1 expression in gut and TPH2 expression in brain stem were analyzed. Bone histomorphometry was also performed. As shown in FIG. 7B, pCPA treatment corrected the bone abnormalities observed in Lrp5−/− mice without overtly affecting bone mass in WT mice. This rescue of the Lrp5−/− phenotype was achieved by normalization of the gut TPH1 mRNA and of serum serotonin levels (FIGS. 7C and 7D). Brain TPH2 mRNA levels were not affected in the treated mice, further demonstrating that the phenotype observed in Lrp5−/− bones is directly caused by changes in serum, not brain, serotonin levels.

Serotonin Binds to Specific Serotonin Receptors in Osteoblasts

From the working hypothesis that Lrp5 acts on bone formation through serum serotonin, a third inference was tested: osteoblasts should express some serotonin receptors, and serotonin treatment of osteoblasts should blunt the expression of Cyclin D1, D2 and E1 without affecting the expression of α(I) collagen, Runx2 or Osteocalcin. To address the first part of this point, the expression of each of the known serotonin receptors was analyzed by qPCR in WT osteoblasts. The expression of three different serotonin receptors in osteoblasts, all belonging to the G-protein coupled receptor superfamily was detected (Noda et al., 2004, Mol. Neurobiol. 29:31-39). HT1B was the most highly expressed receptor. It is coupled to $G_i$-type G proteins and inhibits adenylyl cyclase activity. HT2B is the second most abundant receptor and is coupled to the G proteins that activate a phosphatidyl-inositol-calcium second messenger system. Lastly, HT2A is the third receptor significantly expressed in osteoblasts. Like HT2B, it is coupled to the G proteins that activate a phosphatidylinositol-calcium second messenger system. Remarkably, HT1B, the most highly expressed serotonin receptor in osteoblasts, is also more highly expressed in these cells than in any other cells. Thus, there is at least a partially cell-specific signaling pathway occurring in osteoblasts that could be able to specifically transduce serotonin signaling in these cells. See FIG. 8 which shows real-time PCR analysis of the expression of known serotonin receptors expression in WT osteoblasts (A) and of the expression of cyclins and osteoblast-specific genes in primary osteoblasts treated with serotonin or vehicle (B).

To test whether serotonin regulates the expression of cyclins in osteoblasts, a real-time PCR analysis of cyclin expression in primary osteoblasts treated with serotonin or vehicle was performed. As shown in FIG. 8B, expression of Cyclin D1 and D2 was decreased in the presence of serotonin. In contrast, expression of Runx2, Osteocalcin and Type I collagen was not modified (FIG. 8B). That the molecular signature of serotonin treatment of osteoblasts is similar to the one displayed in absence of Lrp5 further strengthens the hypothesis of a functional link between Lrp5 and serotonin signaling in osteoblasts.

Figure 8:
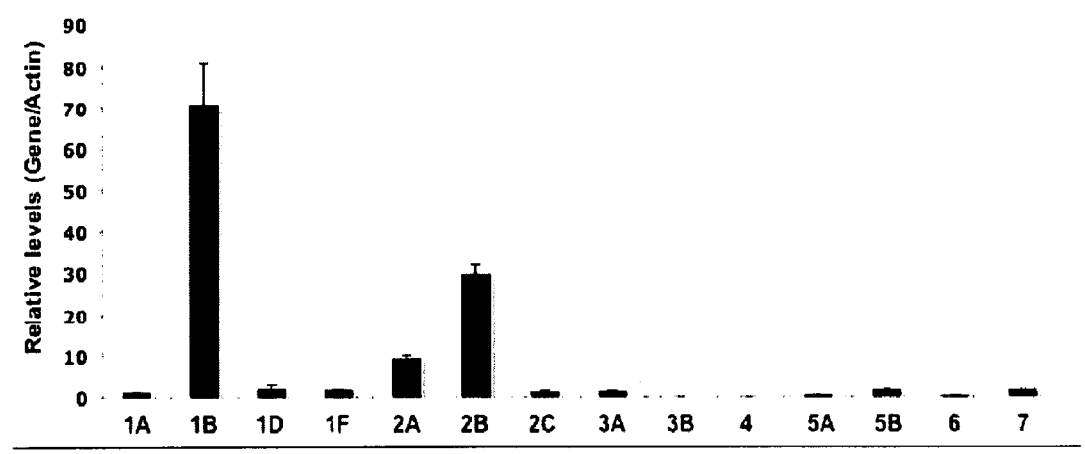
FIG. 8. Real-time PCR analysis of the expression of known serotonin receptors in WT osteoblasts (A) and the expression of cyclins and osteoblast-specific genes in primary osteoblasts treated with serotonin or vehicle (B).
Figure 8:
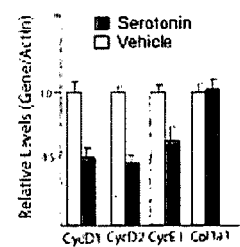
Figure 9:
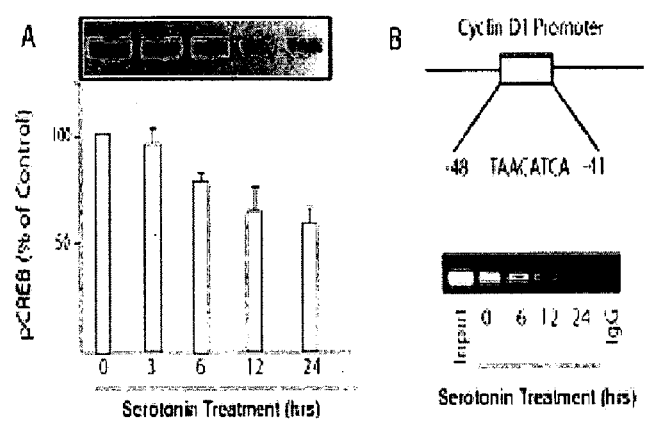
FIG. 9. Western blot analysis of CREB phosphorylation (A) and ChIP analysis of CREB binding to the Cyclin D1 promoter (B) in primary osteoblasts treated with serotonin for the indicated times.

Decreased expression of Cyclin D1 is a major feature of both Lrp5 deficiency and serotonin treatment of osteoblasts (FIGS. 1 and 8). One transcription factor that is known to modulate the expression of cyclin genes and is expressed in osteoblasts is CREB (Fu et al., 2005, Cell 122:803-815). Therefore, whether serotonin could decrease CREB activity in these cells was tested. As shown in FIG. 9A, serotonin treatment significantly decreased CREB phosphorylation in primary osteoblasts. Furthermore, a CREB binding site in the Cyclin D1 mouse promoter was identified and it was shown using ChIP assays that serotonin decreased binding of CREB to this promoter (FIG. 9B). These two observations raise the hypothesis that CREB could be mediating serotonin action on osteoblasts.

TPH1 Expression is Increased in Aging Animals

Figure 10:
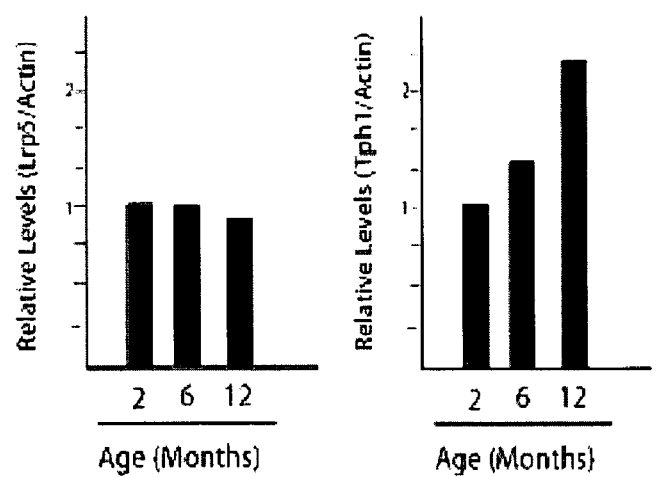
FIG. 10. Real-time PCR analysis of the expression of Tph1 (left panel) and Lrp5 (right panel) in duodenum of WT mice at the indicated ages.

It has been shown in *C. elegans* that TPH1 expression increases with age (Murakami et al., 2007 Feb. 28 [Epub ahead of print], Neurobiol Aging). To test if this was also the case in mammals, TPH1 expression in aging mice was analyzed. Using real time PCR, it was shown that, while expression of Lrp5 remained stable with age, expression of TPH1 doubled in 1 year-old compared to 2 month-old mice (FIG. 10). Since serum serotonin acts as a negative regulator of bone formation, such an increase in TPH1 expression with age exacerbates the bone loss associated with aging and therefore is a target for therapeutic intervention for age-related bone loss.

Methods of Diagnosis

The results disclosed herein show that elevated serum serotonin decreases bone mass and low serum serotonin increases it. Thus, certain embodiments of the invention are directed to methods for diagnosing persons at risk of developing high or low bone mass diseases and to methods for treating or preventing diseases associated with abnormally low bone mass (such as osteoporosis and OPPG) and abnormally high bone mass (such as high bone mass syndrome) by administering drugs that either decrease or increase, respectively, the level of peripheral serum serotonin. Other embodiments are directed to new pharmaceutical compositions for treating or preventing bone diseases of high or low bone mass.

One embodiment of the invention is directed to a method for determining if a patient is at risk of developing a bone disease by determining the patient's level of serum serotonin. If the patient's level is significantly lower (at least about 25% lower) than the level in a normal subject, then the patient is at risk of developing abnormally high bone mass and serotonin can be administered (preferably intravenously) to normalize serum serotonin, thereby preventing high bone mass from developing. Alternatively, if the patient level of serum serotonin is significantly higher (more than about 25% higher) than the level in a normal subject, then the patient is at risk of developing abnormally low bone mass and TPH1 inhibitors or other therapeutic agents that reduce serotonin synthesis, or serotonin receptor antagonists (that target HT1B, HT2A and/or HT2B) can be administered to reduce (and preferably normalize) serum serotonin levels, thereby preventing low bone mass from developing. Patient monitoring will determine if an abnormal serum serotonin profile is chronic. If it is chronic, then the patient may need to continue treatment to normalize serum serotonin.

In this context, when a patient's level of serum serotonin is compared to the level of serum serotonin in a normal subject, it should be understood that "normal subject" refers to a person who is matched to the patient in those characteristics that would be expected to affect serum serotonin levels, e.g., gender, age, general health, medications being taken, etc.

Methods of Treatment and Prevention of Low and High Bone Mass Diseases

The present invention provides a method of preventing or treating a low bone mass disease in a patient known or suspected to be in need of such prevention or treatment comprising administering to the patient a therapeutically effective amount of an agent that decreases serum serotonin levels.

In certain embodiments, the agent that decreases serum serotonin levels is a TPH1 inhibitor or a serotonin receptor antagonist.

In certain embodiments, the agent that decreases serum serotonin levels is a TPH1 inhibitor that reduces serum serotonin to a level that is at least about 10% less than the level before treatment with the TPH1 inhibitor. In certain embodiments, the TPH1 inhibitor reduces serum serotonin to a level that is about 10% less, about 20% less, about 30% less, about 40% less, about 50% less, about 60% less, about 70% less, about 80% less, or about 90% less, than the level before treatment with the TPH1 inhibitor.

In certain embodiments, the agent is a TPH1 inhibitor selected from the group consisting of:
pCPA;
CBMIDA;
LP-533401;
LP-615819;
(S)-2-Amino-3-(4-(4-amino-6-((R)-1-(naphthalen-2-yl)ethylamino)-1,3,5-triazin-2-yl)phenyl)propanoic acid;
(S)-2-Amino-3-(4-(4-amino-6-((4'-methylbiphenyl-4-yl)methylamino-1,3,5-triazin-2-yl)phenyl)propanoic acid;
(S)-2-Amino-3-(4-(4-morpholino-6-(naphthalen-2-ylmethylamino)-1,3,5-triazin-2-yl)phenyl)propanoic acid;
(2S)-2-Amino-3-(4-(2-amino-6-(2,2,2-trifluoro-1-(2-(trifluoromethyl)phenyl)ethoxy)pyrimidin-4-yl)phenyl)propanoic acid;
(2S)-2-Amino-3-(4-(2-amino-6-(2,2,2-trifluoro-1-p-tolylethoxy)pyrimidin-4-yl)phenyl)propanoic acid;
(2S)-2-Amino-3-(4-(2-amino-6-(1-cyclohexyl-2,2,2-trifluoroethoxy)pyrimidin-4-yl(phenyl)propanoic acid;
(S)-2-Amino-3-(4-(6-(2-fluorophenoxy)pyrimidin-4-yl)phenyl)propanoic acid;
(2S)-2-Amino-3-(4-(4-(3-(4-chlorophenyl)piperidin-1-yl)-1,3,5-triazin-2-yl)phenyl)propanoic acid;
(2S)-2-Amino-3-(4-(4-amino-6-(2,2,2-trifluoro-1-phenylethoxy)-1,3,5-triazin-2-yl)phenyl)propanoic acid;
(S)-2-Amino-3-(5-(4-amino-6-((R)-(naphthalen-2-yl)ethylamino)-1,3,5-triazin-2-yl)pyridin-2-yl)propanoic acid;
(S)-2-Amino-3-(3-(4-amino-6-(R)-1-(naphthalen-2-yl)ethylamino)-1,3,5-triazin-2-yl)-1H-pyrazol-1-yl)propanoic acid;
(S)-2-Amino-3-(4'-(3-(cyclopentyloxy)-4-methoxybenzylamino)biphenyl-4-yl)propanoic acid;
(S)-2-Amino-3-(4-(6-(3-(cyclopentyloxy)-4-methoxybenzylamino)pyrimidin-4-yl)phenyl)propanoic acid;
(S)-2-Amino-3-(4-(6-(3-(cyclopentyloxy)-4-methoxybenzylamino)pyrazin-2-yl)phenyl)propanoic acid;
(S)-2-Amino-3-(4-(5-((4'-methylbiphenyl-2-yl)methylamino)pyrazin-2-yl)phenyl)propanoic acid;
(2S)-2-Amino-3-(4-(6-(2,2,2-trifluoro-1-phenylethoxy)-pyrimidin-4-yl)phenyl)propanoic acid;
(2S)-2-Amino-3-(4-(6-(1-(3,4-difluorophenyl)-2,2,2-trifluoroethoxy)pyrimidin-4-yl)phenyl)propanoic acid;
(S)-2-Amino-3-(4-(5-(3-(cyclopentyloxy)-4-methoxybenzylamino)-pyrazin-2-yl)phenyl)propanoic acid;
(S)-2-Amino-3-(4-(5-((3-(cyclopentyloxy)-4-methoxybenzyl)-(methyl)amino)pyrazin-2-yl)phenyl)propanoic acid;
(S)-2-Amino-3-(4-(5-((1,3-dimethyl-1H-pyrazol-4-yl)methylamino)pyrazin-2-yl)phenyl)propanoic acid;
(S)-2-Amino-3-(4-(4-amino-6-((S)-1-(naphthalen-2-yl)ethylamino)-1,3,5-triazin-2-yloxy)phenyl)propanoic acid;
(S)-2-Amino-3-(4-(4-amino-6-((R)-1-(biphenyl-2-yl)-2,2,2-trifluoroethoxy)-1,3,5-triazin-2-yl) phenyl)propanoic acid;
(2S)-2-Amino-3-(4-(4-amino-6-(1-(6,8-difluoronaphthalen-2-yl)ethylamino)-1,3,5-triazin-2-yl)phenyl)propanoic acid;
(2S)-2-Amino-3-(4-(4-amino-6-(2,2,2-trifluoro-1-(3'-methylbiphenyl-2-yl)ethoxy)-1,3,5-triazin-2-yl)phenyl)propanoic acid;
(S)-2-Amino-3-(4-(5-(3,4-dimethoxyphenylcarbamoyl)-pyrazin-2-yl)phenyl)propanoic acid;
(S)-2-Amino-3-(4-(2-amino-6-(4-(2-(trifluoromethyl)phenyl)-piperidin-1-yl)pyrimidin-4-yl)phenyl)propanoic acid;
(S)-2-Amino-3-(4-(2-amino-6-((R)-1-(naphthalen-2-yl)ethylamino)pyrimidin-4-yl)phenyl)propanoic acid;
(S)-2-Amino-3-(4-(2-amino-6-(methyl(R)-1-(naphthalen-2-yl)ethyl)amino)pyrimidin-4-yl)phenyl)propanoic acid;
(S)-2-Amino-3-(4-(2-amino-6-((S)-2,2,2-trifluoro-1-(6-methoxynaphthalen-2-yl)ethoxy)pyrimidin-4-yl)phenyl)propanoic acid;
(S)-2-Amino-3-(4-(5-(biphenyl-4-ylmethylamino)pyrazin-2-yl)phenyl)propanoic acid;
(S)-2-Amino-3-(4-(5-(naphthalen-2-ylmethylamino)pyrazin-2-yl)phenyl)propanoic acid;
(S)-2-(Tert-butoxycarbonylamino)-3-(4-(5-(naphthalen-2-ylmethylamino)pyrazin-2-yl)phenyl)propanoic acid;
(S)-2-Morpholinoethyl 2-amino-3-(4-(5-(naphthalen-2-ylmethylamino)pyrazin-2-yl)phenyl)propanoate;
(S)-2-Amino-3-(4-(2-amino-6-(2,2,2-trifluoro-1-(3'-fluorobiphenyl-4-yl)ethoxy)pyrimidin-4-yl)phenyl)propanoic acid;
(S)-2-Amino-3-(4-(2-amino-6-(benzylthio)pyrimidin-4-yl)phenyl)propanoic acid;
(S)-2-Amino-3-(4-(2-amino-6-(naphthalen-2-ylmethylthio)pyrimidin-4-yl)phenyl)propanoic acid;
(2S)-2-Amino-3-(4-(2-amino-6-(1-(3,4-difluorophenyl)-2,2,2-trifluoroethoxy)pyrimidin-4-yl)phenyl)propanoic acid;
(2S)-2-Amino-3-(4-(2-amino-6-(2,2,2-trifluoro-1-(3'-methylbiphenyl-2-yl)ethoxy)pyrimidin-4-yl)phenyl)propanoic acid;
(S)-2-Amino-3-(4-(5-(3-(cyclopentyloxy)-4-methoxybenzylamino)pyridin-3-yl)phenyl)propanoic acid;
2-Amino-3-(3-(4-amino-6-((R)-1-(naphthalen-2-yl)ethylamino)-1,3,5-triazin-2-yl)phenyl)propanoic acid;
2-Amino-3-(4-(4-amino-6-((R)-1-(naphthalen-2-yl)ethylamino)-1,3,5-triazin-2-yl)-2-fluorophenyl)propanoic acid;
(2S)-2-Amino-3-(4-(4-amino-6-(1-(adamantyl)ethylamino)-1,3,5-triazin-2-yl)phenyl)propanoic acid;
(S)-2-Amino-3-(4-(5-fluoro-4-((R)-1-(naphthalen-2-yl)ethylamino)pyrimidin-2-yl)phenyl)propanoic acid;
(S)-2-Amino-3-(4-(2-amino-6-(4-(trifluoromethyl)-benzylamino)pyrimidin-4-yl)phenyl) propanoic acid;
2-Amino-3-(5-(5-phenylthiophen-2-yl)-1H-indol-3-yl)propanoic acid;
(S)-2-Amino-3-(4-(4-(4-phenoxyphenyl)-1H-1,2,3-triazol-1-yl)phenyl)propanoic acid;
(S)-2-Amino-3-(4-(4-(4-(thiophene-2-carboxamido)phenyl)-1H-1,2,3-triazol-1-yl)phenyl)propanoic acid; and
(S)-2-Amino-3-(4-(2-amino-6-(phenylethynyl)pyrimidin-4-yl)phenyl)propanoic acid;
as well as racemic mixtures and individual enantiomers of said compounds, and salts of said compounds with a physiologically acceptable acid.

Additional TPH1 inhibitors that may be used in the present invention are listed in the table below.

TABLE 2

(S)-2-amino-3-(4-(5-(2-fluoro-4,5-dimethoxybenzylamino)pyrazin-2-yl)phenyl)propanoic acid
(S)-2-amino-3-(4-(2-amino-6-(4-(2-methoxyphenyl)piperidin-1-yl)pyrimidin-4-yl)phenyl)propanoic acid
(S)-2-amino-3-(4-(6-(3-(cyclopentyloxy)-4-methoxybenzylamino)-2-(dimethylamino)pyrimidin-4-yl)phenyl)propanoic acid
(S)-2-amino-3-(4-(5-(3,4-dimethylbenzylamino)pyrazin-2-yl)phenyl)propanoic acid
(S)-2-amino-3-(4-(5-(biphenyl-2-ylmethylamino)pyrazin-2-yl)phenyl)propanoic acid
(S)-ethyl 2-amino-3-(4-(2-amino-6-(4-(trifluoromethyl)benzylamino)pyrimidin-4-yl)phenyl)propanoate
(S)-2-amino-3-(4-(5-(cyclopentylmethylamino)pyrazin-2-yl)phenyl)propanoic acid
(2S)-2-amino-3-(4-(2-amino-6-(3-(2-(trifluoromethyl)phenyl)pyrrolidin-1-yl)pyrimidin-4-yl)phenyl)propanoic acid
(2S)-2-amino-3-(4-(2-amino-6-(1,2,3,4-tetrahydronaphthalen-1-ylamino)pyrimidin-4-yl)phenyl)propanoic acid
(S)-2-amino-3-(4-(2-amino-6-((R)-1-(naphthalen-2-yl)ethoxy)pyrimidin-4-yl)phenyl)propanoic acid
(2S)-2-amino-3-(4-(2-amino-6-(1,2-diphenylethylamino)pyrimidin-4-yl)phenyl)propanoic acid
(S)-2-amino-3-(4-(2-amino-6-((R)-1-(4-(benzo[b]thiophen-3-yl)phenyl)ethylamino)pyrimidin-4-yl)phenyl)propanoic acid
(S)-2-amino-3-(4-(4-amino-6-((R)-1-(4'-methoxybiphenyl-4-yl)ethylamino)-1,3,5-triazin-2-yl)phenyl)propanoic acid
2-amino-3-(1-(4-amino-6-((R)-1-(naphthalen-2-yl)ethylamino)-1,3,5-triazin-2-yl)piperidin-4-yl)propanoic acid
(2S)-2-amino-3-(4-(4-amino-6-(1-(4-fluoronaphthalen-1-yl)ethylamino)-1,3,5-triazin-2-yl)phenyl)propanoic acid
(S)-2-amino-3-(4-(4-amino-6-((3'-fluorobiphenyl-4-yl)methylamino)-1,3,5-triazin-2-yl)phenyl)propanoic acid
2-amino-3-(4-(4-amino-6-((R)-1-(naphthalen-2-yl)ethylamino)-1,3,5-triazin-2-yl)-2-fluorophenyl)propanoic acid
(S)-2-amino-3-(4-(2-amino-6-((R)-2,2,2-trifluoro-1-(3'-methoxybiphenyl-4-yl)ethoxy)pyrimidin-4-yl)phenyl)propanoic acid
(2S)-2-amino-3-(4-(4-amino-6-(2,2,2-trifluoro-1-(3'-fluorobiphenyl-4-yl)ethoxy)-1,3,5-triazin-2-yl)phenyl)propanoic acid
(2S)-2-amino-3-(4-(4-amino-6-(1-(4-tert-butylphenyl)ethylamino)-1,3,5-triazin-2-yl)phenyl)propanoic acid
(2S)-2-amino-3-(4-(2-amino-6-(2,2,2-trifluoro-1-(3'-fluorobiphenyl-4-yl)ethoxy)pyrimidin-4-yl)phenyl)propanoic acid
(2S)-2-amino-3-(4-(4-amino-6-(6,7-dihydroxy-1-methyl-3,4-dihydroisoquinolin-2(1H)-yl)-1,3,5-triazin-2-yl)phenyl)propanoic acid
(2S)-2-amino-3-(4-(4-amino-6-(2,2,2-trifluoro-1-(3'-methylbiphenyl-4-yl)ethoxy)-1,3,5-triazin-2-yl)phenyl)propanoic acid
(S)-2-amino-3-(4-(4-amino-6-((R)-1-(naphthalen-2-yl)ethylamino)pyrimidin-2-yl)phenyl)propanoic acid
(S)-2-amino-3-(4-(2-amino-6-(benzylthio)pyrimidin-4-yl)phenyl)propanoic acid
(2S)-2-amino-3-(4-(2-amino-6-(2,2,2-trifluoro-1-(4'-fluorobiphenyl-4-yl)ethoxy)pyrimidin-4-yl)phenyl)propanoic acid
(2S)-2-amino-3-(4-(6-(3-(4-chlorophenoxy)piperidin-1-yl)pyrimidin-4-yl)phenyl)propanoic acid
(S)-3-(4-(4-amino-6-((R)-1-(naphthalen-2-yl)ethylamino)-1,3,5-triazin-2-yl)phenyl)-2-(2-aminoacetamido)propanoic acid
(S)-2-amino-3-(4-(6-((R)-1-(naphthalen-2-yl)ethylamino)-2-(trifluoromethyl)pyrimidin-4-yl)phenyl)propanoic acid
(S)-2-amino-3-(4-(2-amino-6-(4-(3-chlorophenyl)piperazin-1-yl)pyrimidin-4-yl)phenyl)propanoic acid
(S)-2-amino-3-(4-(2-amino-6-((R)-2,2,2-trifluoro-1-phenylethoxy)pyrimidin-4-yl)phenyl)propanoic acid
(2S)-2-amino-3-(4-(2-amino-6-(1,4-diphenylbutylamino)pyrimidin-4-yl)phenyl)propanoic acid
(2S)-2-amino-3-(4-(6-(1-(3'-chlorobiphenyl-2-yl)-2,2,2-trifluoroethoxy)pyrimidin-4-yl)phenyl)propanoic acid
(2S)-2-amino-3-(4-(4-amino-6-(1-(biphenyl-4-yl)-2,2,2-trifluoroethoxy)-1,3,5-triazin-2-yl)phenyl)propanoic acid
(2S)-2-amino-3-(4-(2-amino-6-(2,2,3,3,3-pentafluoro-1-(3-fluoro-4-methylphenyl)propoxy)pyrimidin-4-yl)phenyl)propanoic acid
(S)-ethyl 2-amino-3-(4-(2-amino-6-((R)-2,2,2-trifluoro-1-(3'-methoxybiphenyl-4-yl)ethoxy)pyrimidin-4-yl)phenyl)propanoate
(S)-2-amino-3-(4-(2-amino-6-((S)-2,2,2-trifluoro-1-(3'-methoxybiphenyl-4-yl)ethoxy)pyrimidin-4-yl)phenyl)propanoic acid
(2S)-2-amino-3-(4-(2-amino-6-(2,2,2-trifluoro-1-(3-fluoro-3'-methoxybiphenyl-4-yl)ethoxy)pyrimidin-4-yl)phenyl)propanoic acid
(2S)-2-amino-3-(4-(2-amino-6-(1-(3'-(dimethylamino)biphenyl-2-yl)-2,2,2-trifluoroethoxy)pyrimidin-4-yl)phenyl)propanoic acid
(2S)-2-amino-3-(4-(2-amino-6-(2,2,2-trifluoro-1-(3'-methoxy-5-methylbiphenyl-2-yl)ethoxy)pyrimidin-4-yl)phenyl)propanoic acid
(2S)-2-amino-3-(4-(2-amino-6-(2,2,2-trifluoro-1-(4'-methoxy-5-methylbiphenyl-2-yl)ethoxy)pyrimidin-4-yl)phenyl)propanoic acid
(2S)-2-amino-3-(4-(2-amino-6-(2,2,2-trifluoro-1-(3'-methoxy-3-(methylsulfonyl)biphenyl-4-yl)ethoxy)pyrimidin-4-yl)phenyl)propanoic acid
(2S)-2-amino-3-(4-(2-amino-6-(1-(2-(cyclopropylmethoxy)-4-fluorophenyl)-2,2,2-trifluoroethoxy)pyrimidin-4-yl)phenyl)propanoic acid
(2S)-2-amino-3-(4-(6-(1-(2-(cyclopropylmethoxy)-4-fluorophenyl)-2,2,2-trifluoroethoxy)pyrimidin-4-yl)phenyl)propanoic acid
(2S)-2-amino-3-(4-(2-amino-6-(2,2,2-trifluoro-1-(2-(isopentyloxy)phenyl)ethoxy)pyrimidin-4-yl)phenyl)propanoic acid
(2S)-2-amino-3-(4-(5-(2,2,2-trifluoro-1-(3'-fluorobiphenyl-4-yl)ethoxy)pyrazin-2-yl)phenyl)propanoic acid
(2S)-2-amino-3-(4-(2-amino-6-(2,2,2-trifluoro-1-(4'-methoxybiphenyl-2-yl)ethoxy)pyrimidin-4-yl)phenyl)propanoic acid
(2S)-2-amino-3-(4-(2-amino-6-(1-(3'-carbamoylbiphenyl-2-yl)-2,2,2-trifluoroethoxy)pyrimidin-4-yl)phenyl)propanoic acid
(2S)-2-amino-3-(4-(2-amino-6-(1-(4'-carbamoylbiphenyl-2-yl)-2,2,2-trifluoroethoxy)pyrimidin-4-yl)phenyl)propanoic acid
(2S)-2-amino-3-(4-(2-amino-6-(2,2,2-trifluoro-1-(4-(2-methoxyphenoxy)phenyl)ethoxy)pyrimidin-4-yl)phenyl)propanoic acid
(2S)-2-amino-3-(4-(6-(2,2,2-trifluoro-1-(4-(2-methoxyphenoxy)phenyl)ethoxy)pyrimidin-4-yl)phenyl)propanoic acid
(2S)-2-amino-3-(4-(6-(2,2,2-trifluoro-1-(2-(isopentyloxy)phenyl)ethoxy)pyrimidin-4-yl)phenyl)propanoic acid
(2S)-3-(4-(6-(1-(3'-acetamidobiphenyl-2-yl)-2,2,2-trifluoroethoxy)-2-aminopyrimidin-4-yl)phenyl)-2-aminopropanoic acid
(2S)-3-(4-(6-(1-(4'-acetamidobiphenyl-2-yl)-2,2,2-trifluoroethoxy)-2-aminopyrimidin-4-yl)phenyl)-2-aminopropanoic acid
(2S)-2-amino-3-(4-(2-amino-6-(1-(4-cyanophenyl)-2,2,2-trifluoroethoxy)pyrimidin-4-yl)phenyl)propanoic acid
(S)-ethyl 2-amino-3-(4-(2-amino-6-((R)-2,2,2-trifluoro-1-p-tolylethoxy)pyrimidin-4-yl)phenyl)propanoate
(2S)-2-amino-3-(4-(2-amino-6-(2,2,2-trifluoro-1-(1-methoxybicyclo[2.2.2]oct-5-en-2-yl)ethoxy)pyrimidin-4-yl)phenyl)propanoic acid
(2S)-2-amino-3-(4-(2-amino-6-(1-(4-(cyclopentyloxy)phenyl)-2,2,2-trifluoroethoxy)pyrimidin-4-yl)phenyl)propanoic acid
(2S)-2-amino-3-(4-(6-(1-(4-(cyclopentyloxy)phenyl)-2,2,2-trifluoroethoxy)pyrimidin-4-yl)phenyl)propanoic acid
(2S)-2-amino-3-(4-(2-amino-6-(2,2,2-trifluoro-1-(4-(3-methoxyphenoxy)phenyl)ethoxy)pyrimidin-4-yl)phenyl)propanoic acid
(2S)-2-amino-3-(4-(2-amino-6-(1-(4,5-dimethoxybiphenyl-2-yl)-2,2,2-trifluoroethoxy)pyrimidin-4-yl)phenyl)propanoic acid
(2S)-2-amino-3-(4-(2-amino-6-(1-(4,5-dimethoxy-3'-methylbiphenyl-2-yl)-2,2,2-trifluoroethoxy)pyrimidin-4-yl)phenyl)propanoic acid
(2S)-2-amino-3-(4-(5-(2,2,2-trifluoro-1-(2'-methylbiphenyl-2-yl)ethoxy)pyrazin-2-yl)phenyl)propanoic acid
(2S)-2-amino-3-(4-(6-(2,2,2-trifluoro-1-(4-(3-

TABLE 2-continued methoxyphenoxy)phenyl)ethoxy)pyrimidin-4-
yl)phenyl)propanoic acid
(2S)-2-amino-3-(4-(2-amino-6-(1-(2-(3,5-
difluorophenoxy)phenyl)-2,2,2-trifluoroethoxy)pyrimidin-4-
yl)phenyl)propanoic acid
(2S)-2-amino-3-(4-(2-amino-6-(2,2,2-trifluoro-1-(4-(4-
methoxyphenoxy)phenyl)ethoxy)pyrimidin-4-
yl)phenyl)propanoic acid
(2S)-2-amino-3-(4-(2-amino-6-(1-(4'-((S)-2-amino-2-
carboxyethyl)biphenyl-2-yl)-2,2,2-trifluoroethoxy)pyrimidin-4-
yl)-phenyl)propanoic acid
(2S)-2-amino-3-(4-(2-amino-6-(1-(2-bromophenyl)-2,2,2-
trifluoroethoxy)pyrimidin-4-yl)phenyl)propanoic acid
(2S)-2-amino-3-(4-(5-(2,2,2-trifluoro-1-(3'-methylbiphenyl-2-
yl)ethoxy)pyrazin-2-yl)phenyl)propanoic acid
(2S)-2-amino-3-(4-(2-amino-6-(2,2,2-trifluoro-1-(4-
methoxybiphenyl-2-yl)ethoxy)pyrimidin-4-yl)phenyl)propanoic
acid
(2S)-2-amino-3-(4-(5-(2,2,2-trifluoro-1-(2-(4-methylthiophen-3-
yl)phenyl)ethoxy)pyrazin-2-yl)phenyl)propanoic acid
(2S)-2-amino-3-(4-(2-amino-6-(2,2,2-trifluoro-1-(4-methoxy-3'-
methylbiphenyl-2-yl)ethoxy)pyrimidin-4-yl)phenyl)propanoic
acid
(2S)-2-amino-3-(4-(2-amino-6-(2,2,2-trifluoro-1-(3'-
(hydroxymethyl)biphenyl-2-yl)ethoxy)pyrimidin-4-
yl)phenyl)propanoic acid
(2S)-2-amino-3-(4-(2-amino-6-(1-(3'-cyanobiphenyl-2-yl)-2,2,2-
trifluoroethoxy)pyrimidin-4-yl)phenyl)propanoic acid
(2S)-2-amino-3-(4-(6-(1-(2-(3,5-difluorophenoxy)phenyl)-2,2,2-
trifluoroethoxy)pyrimidin-4-yl)phenyl)propanoic acid
(2S)-2-amino-3-(4-(6-(2,2,2-trifluoro-1-(4-(4-
methoxyphenoxy)phenyl)othoxy)pyrimidin-4-
yl)phenyl)propanoic acid
(2S)-2-amino-3-(4-(2-amino-6-(2,2,2-trifluoro-1-(2-(4-
methylthiazol-2-yl)thiophen-3-yl)ethoxy)pyrimidin-4-
yl)phenyl)propanoic acid
(2S)-2-amino-3-(4-(2-amino-6-(2,2,2-trifluoro-1-(5-(4-
methoxyphenyl)isoxazol-3-yl)ethoxy)pyrimidin-4-
yl)phenyl)propanoic acid
(2S)-2-amino-3-(4-(2-amino-6-(2,2,2-trifluoro-1-(1-phenyl-5-
(trifluoromethyl)-1H-pyrazol-4-yl)ethoxy)pyrimidin-4-
yl)phenyl)propanoic acid
(2S)-2-amino-3-(4-(2-amino-6-(1-(2-(cyclohexyloxy)-4-
methylphenyl)-2,2,2-trifluoroethoxy)pyrimidin-4-
yl)phenyl)propanoic acid
(2S)-2-amino-3-(4-(2-amino-6-(1-(2-(cyclopentyloxy)-4-
methylphenyl)-2,2,2-trifluoroethoxy)pyrimidin-4-
yl)phenyl)propanoic acid
(2S)-2-amino-3-(4-(2-amino-6-(1-(benzo[d]thiazol-6-yl)-2,2,2-
trifluoroethoxy)pyrimidin-4-yl)phenyl)propanoic acid
(2S)-2-amino-3-(4-(2-amino-6-(2,2,2-trifluoro-1-(1-methyl-1H-
imidazol-5-yl)ethoxy)pyrimidin-4-yl)phenyl)propanoic acid
(2S)-2-amino-3-(4-(6-(1-(2-(cyclopentyloxy)-4-methylphenyl)-
2,2,2-trifluoroethoxy)pyrimidin-4-yl)phenyl)propanoic acid
(2S)-2-amino-3-(4-(6-(1-(2-(cyclohexyloxy)-4-methylphenyl)-
2,2,2-trifluoroethoxy)pyrimidin-4-yl)phenyl)propanoic acid
(2S)-2-amino-3-(4-(2-amino-6-(2,2,2-trifluoro-1-(pyridin-3-
yl)ethoxy)pyrimidin-4-yl)phenyl)propanoic acid
(2S)-2-amino-3-(4-(2-amino-6-(1-(1,3-dimethyl-1H-pyrazol-5-
yl)-2,2,2-trifluoroethoxy)pyrimidin-4-yl)phenyl)propanoic acid
(S)-2-amino-3-(4-(2-amino-6-(3-hydroxyphenyl)pyrimidin-4-
yl)phenyl)propanoic acid
(2S)-2-amino-3-(4-(2-amino-6-(2,2,2-trifluoro-1-(3'-
hydroxybiphenyl-2-yl)ethoxy)pyrimidin-4-yl)phenyl)propanoic
acid
(S)-2-amino-3-(4-(2-amino-6-(3,5-difluorophenyl)pyrimidin-4-
yl)phenyl)propanoic acid
(2S)-2-amino-3-(4-(2-amino-6-(1-(3',5'-difluorobiphenyl-2-yl)-
2,2,2-trifluoroethoxy)pyrimidin-4-yl)phenyl)propanoic acid
(2S)-2-amino-3-(4-(6-(2,2,2-trifluoro-1-(3'-fluorobiphenyl-3-
yl)ethoxy)pyrazin-2-yl)phenyl)propanoic acid
(2S)-2-amino-3-(4-(2-amino-6-(1-(5-ethoxy-2-methyl-2,3-
dihydrobenzofuran-6-yl)-2,2,2-trifluoroethoxy)pyrimidin-4-
yl)phenyl)propanoic acid
(2S)-2-amino-3-(4-(2-amino-6-(1-(benzofuran-5-yl)-2,2,2-
trifluoroethoxy)pyrimidin-4-yl)phenyl)propanoic acid
(2S)-2-amino-3-(4-(2-amino-6-(2,2,2-trifluoro-1-(2-m-
tolylfuran-3-yl)ethoxy)pyrimidin-4-yl)phenyl)propanoic acid
(S)-ethyl 3-(4-(2-amino-6-((R)-2,2,2-trifluoro-1-(3'-
methoxybiphenyl-4-yl)ethoxy)pyrimidin-4-yl)phenyl)-2-(2-
aminoacetamido)propanoate
(2S)-2-amino-3-(4-(6-(2,2,2-trifluoro-1-(2-(4-methylthiophen-3-
yl)phenyl)ethoxy)pyrazin-2-yl)phenyl)propanoic acid
(2S)-2-amino-3-(4-(2-amino-6-(2,2,2-trifluoro-1-(5-methyl-3-
phenylisoxazol-4-yl)ethoxy)pyrimidin-4-yl)phenyl)propanoic
acid
(S)-2-amino-3-(4-(2-amino-6-(3-(methylthio)phenyl)pyrimidin-
4-yl)phenyl)propanoic acid
(2S)-2-amino-3-(4-(2-amino-6-(2,2,2-trifluoro-1-(3'-
(methylthio)biphenyl-2-yl)ethoxy)pyrimidin-4-
yl)phenyl)propanoic acid
(2S)-2-amino-3-(4-(2-amino-6-(1-(3'-
((dimethylamino)methyl)biphenyl-2-yl)-2,2,2-
trifluoroethoxy)pyrimidin-4-yl)phenyl)propanoic acid
(S)-2-amino-3-(4-(2-amino-6-(3-
(trifluoromethoxy)phenyl)pyrimidin-4-yl)phenyl)propanoic acid
(2S)-2-amino-3-(4-(2-amino-6-(2,2,2-trifluoro-1-(3'-
(trifluoromethoxy)biphenyl-2-yl)ethoxy)pyrimidin-4-
yl)phenyl)propanoic acid
(S)-3-(4-(2-amino-6-((R)-2,2,2-trifluoro-1-(3'-methoxybiphenyl-
4-yl)ethoxy)pyrimidin-4-yl)phenyl)-2-(2-
aminoacetamido)propanoic acid
(2S)-2-amino-3-(4-(2-amino-6-(2,2,2-trifluoro-1-(1-methyl-5-
phenyl-1H-pyrazol-4-yl)ethoxy)pyrimidin-4-
yl)phenyl)propanoic acid
(2S)-2-amino-3-(4-(2-amino-6-(2,2,2-trifluoro-1-(4-
(methylsulfonyl)phenyl)ethoxy)pyrimidin-4-
yl)phenyl)propanoic acid
(S)-2-amino-3-(4-(2-amino-6-((R)-1-(3'-
(dimethylamino)biphenyl-2-yl)-2,2,2-trifluoroethoxy)pyrimidin-
4-yl)phenyl)propanoic acid
(2S)-2-amino-3-(4-(2-amino-6-(1-(2-chloro-4-
(methylsulfonyl)phenyl)-2,2,2-trifluoroethoxy)pyrimidin-4-
yl)phenyl)propanoic acid
(2S)-2-amino-3-(4-(2-amino-6-(2,2,2-trifluoro-1-(3-(furan-2-
yl)thiophen-2-yl)ethoxy)pyrimidin-4-yl)phenyl)propanoic acid
(2S)-2-amino-3-(4-(2-amino-6-(1-(2-(cyclopentyloxy)-4-
fluorophenyl)-2,2,2-trifluoroethoxy)pyrimidin-4-
yl)phenyl)propanoic acid
(2S)-2-amino-3-(4-(2-amino-6-(2,2,2-trifluoro-1-(2-(3-
methoxyphenyl)cyclohex-1-enyl)ethoxy)pyrimidin-4-
yl)phenyl)propanoic acid
(2S)-2-amino-3-(4-(2-amino-6-(2,2,2-trifluoro-1-(pyrimidin-5-
yl)ethoxy)pyrimidin-4-yl)phenyl)propanoic acid
(2S)-2-amino-3-(4-(5-(2,2,2-trifluoro-1-(3'-methoxybiphenyl-3-
yl)ethoxy)pyrazin-2-yl)phenyl)propanoic acid
(S)-2-amino-3-(4-(2-amino-6-((S)-1-(3'-
(dimethylamino)biphenyl-2-yl)-2,2,2-trifluoroethoxy)pyrimidin-
4-yl)phenyl)propanoic acid
(2S)-2-amino-3-(4-(2-amino-6-(2,2,2-trifluoro-1-(2-(furan-2-
carboxamido)phenyl)ethoxy)pyrimidin-4-yl)phenyl)propanoic
acid
(2S)-2-amino-3-(4-(2-amino-6-(1-(4-chloro-2-
(methylsulfonyl)phenyl)-2,2,2-trifluoroethoxy)pyrimidin-4-
yl)phenyl)propanoic acid
(S)-isopropyl 2-amino-3-(4-(2-amino-6-((R)-2,2,2-trifluoro-1-
(3'-methoxybiphenyl-4-yl)ethoxy)pyrimidin-4-
yl)phenyl)propanoate
(2S)-2-amino-3-(4-(6-(1-(2-(cyclopentyloxy)-4-fluorophenyl)-
2,2,2-trifluoroethoxy)pyrimidin-4-yl)phenyl)propanoic acid
(2S)-2-amino-3-(4-(6-(1-(2-(cyclohexyloxy)-4-fluorophenyl)-
2,2,2-trifluoroethoxy)pyrimidin-4-yl)phenyl)propanoic acid
(2S)-2-amino-3-(4-(2-amino-6-(2,2,2-trifluoro-1-(1-(thiophen-2-
yl)cyclohexyl)ethoxy)pyrimidin-4-yl)phenyl)propanoic acid
(2S)-2-amino-3-(4-(2-(2,2,2-trifluoro-1-(3'-methoxybiphenyl-4-
yl)ethoxy)thiazol-5-yl)phenyl)propanoic acid
(2S)-2-amino-3-(4-(2-amino-6-(1-(2-(cyclohexyloxy)-4-
fluorophenyl)-2,2,2-trifluoroethoxy)pyrimidin-4-
yl)phenyl)propanoic acid
(2S)-2-amino-3-(4-(2-amino-6-(2,2,2-trifluoro-1-(1-(4-
methoxyphenyl)cyclohexyl)ethoxy)pyrimidin-4-
yl)phenyl)propanoic acid
(2S)-2-amino-3-(4-(6-(2,2,2-trifluoro-1-(4-fluoro-2-
methylphenyl)ethoxy)pyrimidin-4-yl)phenyl)propanoic acid
(2S)-2-amino-3-(4-(2-amino-6-(2,2,2-trifluoro-1-(4-fluoro-2-
methylphenyl)ethoxy)pyrimidin-4-yl)phenyl)propanoic acid
(2S)-2-amino-3-(4-(2-amino-6-(oxazol-2-
yl(phenyl)methoxy)pyrimidin-4-yl)phenyl)propanoic acid
(S)-2-amino-3-(4-(2-amino-6-(1-cyclohexyl-2,2,2-

| TABLE 2-continued |
|---|
| trifluoroethylideneaminooxy)pyrimidin-4-yl)phenyl)propanoic acid |
| (2S)-2-amino-3-(4-(2-amino-6-(1-(2-(3-(dimethylamino)phenyl)furan-3-yl)-2,2,2-trifluoroethoxy)pyrimidin-4-yl)phenyl)propanoic acid |
| (2S)-2-amino-3-(4-(2-amino-6-(2,2,2-trifluoro-1-(5-phenylthiophen-2-yl)ethoxy)pyrimidin-4-yl)phenyl)propanoic acid |
| (S)-phenyl 2-amino-3-(4-(2-amino-6-((R)-2,2,2-trifluoro-1-(3'-methoxybiphenyl-4-yl)ethoxy)pyrimidin-4-yl)phenyl)propanoate |
| (S)-2-amino-3-(4-(2-amino-6-((R)-1-(3'-((dimethylamino)methyl)biphenyl-4-yl)-2,2,2-trifluoroethoxy)pyrimidin-4-yl)phenyl)propanoic acid |
| (S)-2-amino-3-(4-(1-(3-methoxybenzoyl)-1H-pyrazol-4-yl)phenyl)propanoic acid |
| (2S)-2-amino-3-(4-(6-(2,2,2-trifluoro-1-(5-phenylfuran-2-yl)ethoxy)pyrimidin-4-yl)phenyl)propanoic acid |
| (2S)-2-amino-3-(4-(2-amino-6-(1-(4-chloro-2-fluorophenyl)-2,2,2-trifluoroethoxy)pyrimidin-4-yl)phenyl)propanoic acid |
| (S,E)-2-amino-3-(4-(2-amino-6-(4-(trifluoromethyl)styryl)pyrimidin-4-yl)phenyl)propanoic acid |
| (2S)-2-amino-3-(4-(2-amino-6-(1-(3,4-dichlorophenyl)-2,2,2-trifluoroethoxy)pyrimidin-4-yl)phenyl)propanoic acid |
| (2S)-2-amino-3-(4-(2-amino-6-(1-(4-chloro-3-fluorophenyl)-2,2,2-trifluoroethoxy)pyrimidin-4-yl)phenyl)propanoic acid |
| (S)-2-amino-3-(4-(2-amino-6-((R)-1-(3'-(dimethylamino)biphenyl-4-yl)-2,2,2-trifluoroethoxy)pyrimidin-4-yl)phenyl)propanoic acid |
| (2S)-2-amino-3-(4-(2-amino-6-(1-chloro-2,2,2-trifluoro-1-(4-methoxybiphenyl-2-yl)ethoxy)pyrimidin-4-yl)phenyl)propanoic acid |
| (2S)-2-amino-3-(4-(6-(2,2,2-trifluoro-1-(5-phenylthiophen-2-yl)ethoxy)pyrimidin-4-yl)phenyl)propanoic acid |
| (S)-2-amino-3-(4-(5-(4-phenoxyphenyl)-1H-1,2,3-triazol-1-yl)phenyl)propanoic acid |
| (S,E)-2-amino-3-(4-(2-amino-6-(2-(biphenyl-4-yl)vinyl)pyrimidin-4-yl)phenyl)propanoic acid |
| (S)-2-amino-3-(4-(4-amino-6-((R)-2,2,2-trifluoro-1-(3'-methoxybiphenyl-4-yl)ethoxy)pyrimidin-2-yl)phenyl)propanoic acid |
| (S)-2-amino-3-(4-(4'-methoxybiphenyl-4-ylsulfonamido)phenyl)propanoic acid |
| (2S)-2-amino-3-(4-(2-amino-6-(2,2,2-trifluoro-1-(6-(3-methoxyphenyl)pyridin-3-yl)ethoxy)pyrimidin-4-yl)phenyl)propanoic acid |
| (2S)-2-amino-3-(4-(2-amino-6-(2,2,2-trifluoro-1-(6-(2-fluoro-3-methoxyphenyl)pyridin-3-yl)ethoxy)pyrimidin-4-yl)phenyl)propanoic acid |
| 2-amino-3-(5-(4'-methylbiphenyl-4-yl)-1H-indol-3-yl)propanoic acid |
| 2-amino-3-(5-m-tolyl-1H-indol-3-yl)propanoic acid |
| (2S)-2-amino-3-(4-(2-(2-methoxyphenyl)furan-3-carboxamido)phenyl)propanoic acid |
| 2-amino-3-(5-(1-benzyl-1H-pyrazol-4-yl)-1H-indol-3-yl)propanoic acid |
| (2S)-2-amino-3-(4-(2-amino-6-(2,2,2-trifluoro-1-(6-(thiophen-2-yl)pyridin-3-yl)ethoxy)pyrimidin-4-yl)phenyl)propanoic acid |
| 2-amino-3-(6-(1-benzyl-1H-pyrazol-4-yl)-1H-indol-3-yl)propanoic acid |
| (S)-2-amino-3-(4-((2-(4-(trifluoromethyl)phenyl)thiazol-4-yl)methylamino)phenyl)propanoic acid |
| (S)-2-amino-3-(4-((4'-methoxybiphenyl-4-ylsulfonamido)methyl)phenyl)propanoic acid |
| (S)-2-amino-3-(4-(3-(2-methoxydibenzo[b,d]furan-3-yl)ureido)phenyl)propanoic acid |
| (S)-2-amino-3-(4-(3-(2,2-diphenylethyl)ureido)phenyl)propanoic acid |
| (S)-2-amino-3-(4-(phenylethynyl)phenyl)propanoic acid |
| (S)-2-amino-3-(4-(2-amino-6-((5-(1-methyl-5-(trifluoromethyl)-1H-pyrazol-3-yl)thiophen-2-yl)methoxy)pyrimidin-4-yl)phenyl)propanoic acid |
| (2S)-2-amino-3-(4-(2-amino-6-(1,1,1-trifluoro-3-((R)-2,2,3-trimethylcyclopent-3-enyl)propan-2-yloxy)pyrimidin-4-yl)phenyl)propanoic acid |
| (2S)-2-amino-3-(4-(2-amino-6-(3-(2-hydroxyethylcarbamoyl)piperidin-1-yl)pyrimidin-4-yl)phenyl)propanoic acid |
| (2S)-2-amino-3-(4-(2-amino-6-(3-(pyridin-2-yloxy)piperidin-1-yl)pyrimidin-4-yl)phenyl)propanoic acid |

| TABLE 2-continued |
|---|
| (S)-2-amino-3-(4-(2-amino-6-(4-chloro-3-(piperidine-1-carbonyl)phenyl)pyrimidin-4-yl)phenyl)propanoic acid |

Additional TPH1 inhibitors that may be used in the present invention include:

N-[(1R,4R,9aS)-4-phenyl octahydropyrido[2,1-c][1,4]oxazin-1-yl]3,4,5-trimethoxybenzamide;

2,6-Piperidinedione, 3-[3-(dimethylamino)propyl]-3-(3-methoxyphenyl)-4,4-dimethyl-, monohydrochloride; and Triptosine (CAS registry number 86248-47-7; U.S. Pat. No. 4,472,387).

Methods of making many of the therapeutic agents disclosed in the preceding paragraphs are disclosed in International Patent Publication WO 2007/089335. Such disclosures are incorporated herein by reference.

In certain embodiments, the therapeutic agent is a TPH1 inhibitor having the structure:

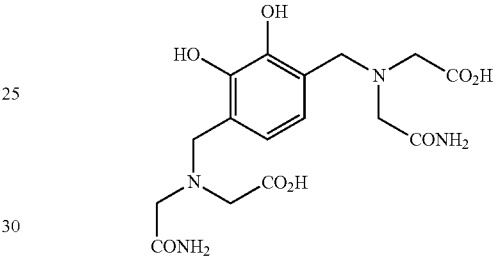

In certain embodiments, the therapeutic agent is a TPH1 inhibitor having the structure:

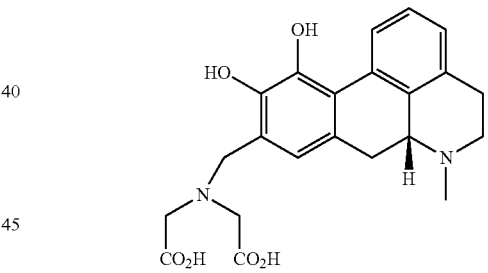

In certain embodiments, the therapeutic agent is a TPH1 inhibitor having the structure:

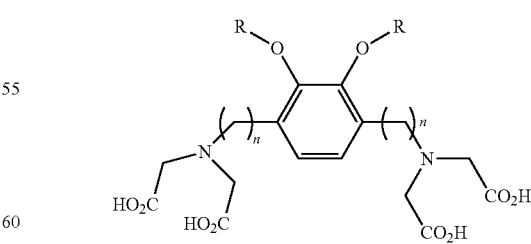

where R is hydrogen or lower alkyl, where lower alkyl refers to a straight-chain or branched-chain hydrocarbon group having 1 to 6 carbon atoms (e.g., methyl, ethyl, propyl, isopropyl, butyl, isobutyl, pentyl and hexyl); and n is 1, 2, or 3.

In certain embodiments, the therapeutic agent is a TPH1 inhibitor having the structure:

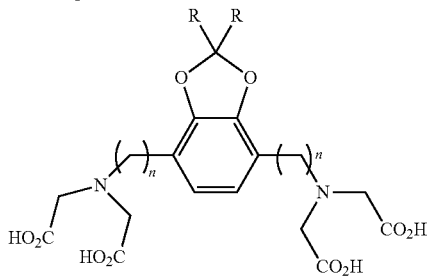

where R is hydrogen or lower alkyl, where lower alkyl refers to a straight-chain or branched-chain hydrocarbon group having 1 to 6 carbon atoms (e.g., methyl, ethyl, propyl, isopropyl, butyl, isobutyl, pentyl and hexyl); and
n is 1, 2, or 3.

In certain embodiments, the therapeutic agent is a TPH1 inhibitor having the structure:

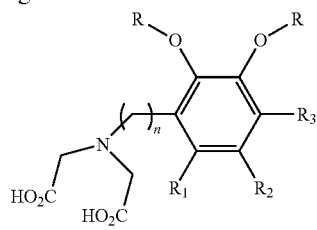

where R is hydrogen or lower alkyl, where lower alkyl refers to a straight-chain or branched-chain hydrocarbon group having 1 to 6 carbon atoms (e.g., methyl, ethyl, propyl, isopropyl, butyl, isobutyl, pentyl and hexyl);
$R_1$, $R_2$, and $R_3$, are independently:
  hydrogen;
  halogen (preferably F or Cl);
  lower alkyl, where lower alkyl refers to a straight-chain or branched-chain hydrocarbon group having 1 to 6 carbon atoms (e.g., methyl, ethyl, propyl, isopropyl, butyl, isobutyl, pentyl and hexyl);
  alkoxy, where alkoxy refers to a group R'—O—, where R' is lower alkyl as defined above;
  amino; or
  nitro;
and
n is 1, 2, or 3.

In certain embodiments, the therapeutic agent is a TPH1 inhibitor having the structure:

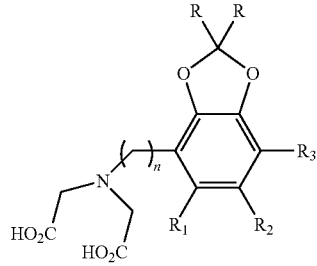

where R is hydrogen or lower alkyl, where lower alkyl refers to a straight-chain or branched-chain hydrocarbon group having 1 to 6 carbon atoms (e.g., methyl, ethyl, propyl, isopropyl, butyl, isobutyl, pentyl and hexyl);
$R_1$, $R_2$, and $R_3$, are independently:
  hydrogen;
  halogen (preferably F or Cl);
  lower alkyl, where lower alkyl refers to a straight-chain or branched-chain hydrocarbon group having 1 to 6 carbon atoms (e.g., methyl, ethyl, propyl, isopropyl, butyl, isobutyl, pentyl and hexyl);
  alkoxy, where alkoxy refers to a group R'—O—, where R' is lower alkyl as defined above;
  amino; or
  nitro;
and
n is 1, 2, or 3.

In certain embodiments, the therapeutic agent is a TPH1 inhibitor having the structure:

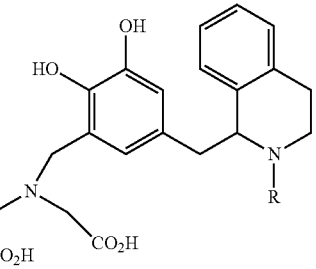

where R is hydrogen; lower alkyl, where lower alkyl refers to a straight-chain or branched-chain hydrocarbon group having 1 to 6 carbon atoms (e.g., methyl, ethyl, propyl, isopropyl, butyl, isobutyl, pentyl and hexyl); or cycloalkyl, where cycloalkyl refers a cyclic hydrocarbon group having 3 to 8 carbon atoms.

In certain embodiments, the therapeutic agent is a TPH1 inhibitor having the structure:

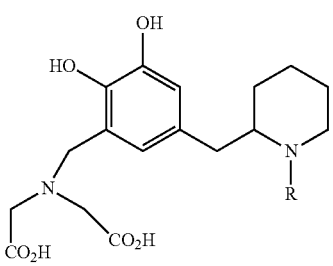

where R is hydrogen; lower alkyl, where lower alkyl refers to a straight-chain or branched-chain hydrocarbon group having 1 to 6 carbon atoms (e.g., methyl, ethyl, propyl, isopropyl, butyl, isobutyl, pentyl and hexyl); or cycloalkyl, where cycloalkyl refers a cyclic saturated hydrocarbon group having 3 to 8 carbon atoms.

In certain embodiments, the therapeutic agent is a TPH1 inhibitor having the structure:

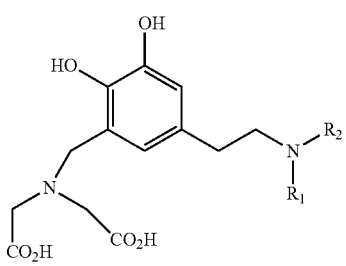

where $R_1$ and $R_2$ are, independently, hydrogen; lower alkyl, where lower alkyl refers to a straight-chain or branched-chain hydrocarbon group having 1 to 6 carbon atoms (e.g., methyl, ethyl, propyl, isopropyl, butyl, isobutyl, pentyl and hexyl); or cycloalkyl, where cycloalkyl refers a cyclic saturated hydrocarbon group having 3 to 8 carbon atoms.

In certain embodiments, the therapeutic agent is a TPH1 inhibitor having the structure:

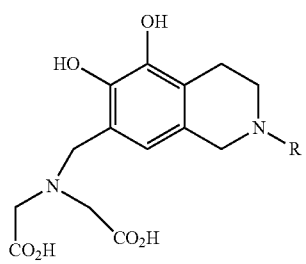

where R is hydrogen; lower alkyl, where lower alkyl refers to a straight-chain or branched-chain hydrocarbon group having 1 to 6 carbon atoms (e.g., methyl, ethyl, propyl, isopropyl, butyl, isobutyl, pentyl and hexyl); or cycloalkyl, where cycloalkyl refers a cyclic saturated hydrocarbon group having 3 to 8 carbon atoms.

In certain embodiments, the therapeutic agent is a TAH1 inhibitor having the structure:

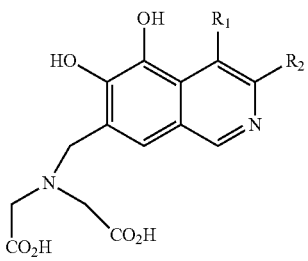

where $R_1$ and $R_2$ are, independently, hydrogen; lower alkyl, where lower alkyl refers to a straight-chain or branched-chain hydrocarbon group having 1 to 6 carbon atoms (e.g., methyl, ethyl, propyl, isopropyl, butyl, isobutyl, pentyl and hexyl); cycloalkyl, where cycloalkyl refers a cyclic saturated hydrocarbon group having 3 to 8 carbon atoms; F, Cl, or OH.

In certain embodiments, the therapeutic agent is a TPH1 inhibitor having the structure:

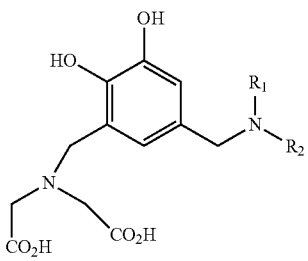

where $R_1$ and $R_2$ are, independently, hydrogen; lower alkyl, where lower alkyl refers to a straight-chain or branched-chain hydrocarbon group having 1 to 6 carbon atoms (e.g., methyl, ethyl, propyl, isopropyl, butyl, isobutyl, pentyl and hexyl); or cycloalkyl, where cycloalkyl refers a cyclic saturated hydrocarbon group having 3 to 8 carbon atoms.

In certain embodiments where the agent is a TPH1 inhibitor that is administered without also administering another pharmaceutically active substance (e.g., an SSRI, a beta blocker, or a serotonin receptor antagonist), the TPH1 inhibitor is not pCPA, CBMIDA, or a compound as follows:

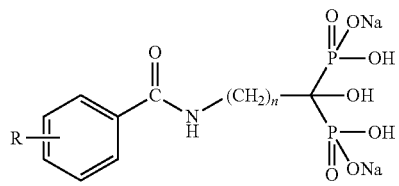

where n is 2, 3, or 5; and
R is, independently, $OCH_3$, $CH_2O_2$, $CH_3$, $NO_2$, or Cl.

The structure of pCPA is:

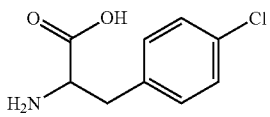

The structure of CBMIDA is:

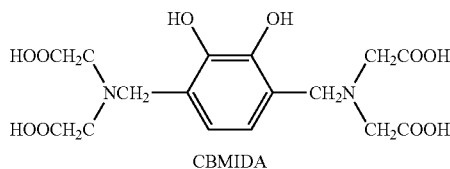

CBMIDA

The ability of selective TPH1 inhibitor CBMIDA to reduce peripheral serotonin measured in serum was tested. Either 250 or 500 mg/kg doses of CBMIDA were administered orally twice in 20 hours to 4 week old mice, 4-5 mice per group. As a control, some mice were untreated and some received 250 mg/kg pCPA orally. The results showed that there was a dose response to CBMIDA administration such that 250 mg/kg caused about a 45% reduction of peripheral serotonin, and 500 mg/kg reduced peripheral serotonin by about 80%. pCPA (250 mg/kg) caused about a 50% reduction of serum serotonin. These results showed that pCPA was more effective than CBMIDA and at the amounts used (250 mg/kg), pCPA did not cross the blood brain barrier. Therefore, pCPA did not decrease serotonin in the brain, where serotonin has the opposite effect of peripheral serotonin. CBMIDA has been reported to be an EDTA analog that increases osteoid volume in beagle dogs and induces proliferation of rat calvarial-derived osteoblasts in vitro (Xie, et al., Bioorganic & Medicinal Chemistry Letters 15 (2005) 3267-3270, incorporated herein by reference in its entirety).

It should be understood that the present invention may encompass the use of pCPA and CBMIDA when those agents are used to decrease serum serotonin levels together with another pharmaceutically active substance, where the other pharmaceutically active substance may be used for another purpose (e.g., an SSRI used to treat depression) or where the other pharmaceutically active substance is used to decrease serum serotonin by a method that does not involve inhibition of TPH1.

The present invention also may further encompass the use of a compound as follows:

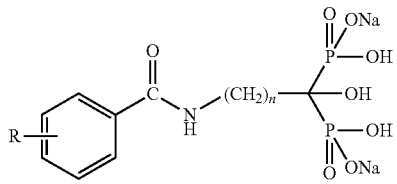

where n is 2, 3, or 5; and
R is, independently, $OCH_3$, $CH_2O_2$, $CH_3$, $NO_2$, or Cl,
where the compound is used with another pharmaceutically active substance that decreases serum serotonin levels.

Methods of making the compounds described in the preceding paragraphs can be found in Xie, et al., Bioorganic & Medicinal Chemistry Letters 15 (2005) 3267-3270, incorporated herein by reference in its entirety.

The present invention also encompasses the use of certain derivatives of the TPH1 inhibitors disclosed herein. For example, prodrugs of the TPH1 inhibitors could be produced by esterifying the carboxylic acid functions of the TPH1 inhibitors with a lower alcohol, e.g., methanol, ethanol, propanol, isopropanol, butanol, etc. The use of prodrugs of the TPH1 inhibitors that are not esters is also contemplated. For example, pharmaceutically acceptable carbonates, thiocarbonates, N-acyl derivatives, N-acyloxyalkyl derivatives, quaternary derivatives of tertiary amines, N-Mannich bases, Schiff bases, amino acid conjugates, phosphate esters, metal salts and sulfonate esters of the TPH1 inhibitors are also contemplated. In some embodiments, the prodrugs will contain a biohydrolyzable moiety (e.g., a biohydrolyzable amide, biohydrolyzable carbamate, biohydrolyzable carbonate, biohydrolyzable ester, biohydrolyzable phosphate, or biohydrolyzable ureide analog). Guidance for the preparation of prodrugs of the TPH1 inhibitors disclosed herein can be found in publications such as *Design of Prodrugs*, Bundgaard, A. Ed., Elsevier, 1985; *Design and Application of Prodrugs, A Textbook of Drug Design and Development*, Krosgaard-Larsen and H. Bundgaard, Ed., 1991, Chapter 5, pages 113-191; and Bundgaard, H., Advanced Drug Delivery Review, 1992, 8, pages 1-38.

In certain embodiments, the TPH1 inhibitor inhibits TPH1 without significantly affecting the level of brain-derived serotonin. Methods of obtaining such inhibitors include: (1) screening for compounds that inhibit TPH1 to a much greater extent than TPH2; and (2) screening for compounds that, while they inhibit both TPH1 and TPH2, cannot cross the blood brain barrier and thus are effectively specific for TPH1 when administered to the patient outside the central nervous system. Of course, compounds that both inhibit TPH1 to a much greater extent than TPH2 and cannot cross the blood brain barrier are also suitable. Preferably, compounds that inhibit TPH1 to a much greater extent than TPH2 have an $IC_{50}$ for TPH2 that is at least about 10-fold greater than their $IC_{50}$ for TPH1.

Several facts suggest that CBMIDA does not cross the blood brain barrier and is therefore TPH2 selective. First, the structure of CBMIDA is EDTA based and when given orally it is poorly transport into the circulation (only 3-5%). Second, EDTA-based compounds in general have poor transport across the blood brain barrier.

In certain embodiments, the agent is a TPH1 inhibitor that does not significantly affect the level of expression of Type 1 collagen, osteocalcin, Runx2, Osterix, or Atf4 in osteoblasts. In certain embodiments, the agent is a TPH1 inhibitor that decreases the expression of Cyclin D1, D2 and E1 in osteoblasts.

In certain embodiments, the agent is a TPH1 inhibitor having the structure:

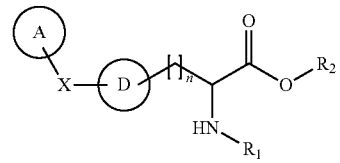

and pharmaceutically acceptable salts and solvates thereof, wherein: A is optionally substituted cycloalkyl, aryl, or heterocycle; X is a bond (i.e., A is directly bound to D), —O—, —S—, —C(O)—, —C(R4)=, =C($R_4$)—, —C($R_3R_4$)—, —C($R_4$)=C($R_4$)—, —C≡C—, —N($R_5$)—, —N($R_5$)C(O)N($R_5$)—, —C($R_3R_4$)N($R_5$)—, —N($R_5$)C($R_3R_4$)—, —ONC($R_3$)—, —C($R_3$)NO—, —C($R_3R_4$)O—, —OC($R_3R_4$)—, —S($O_2$)—, —S($O_2$)N($R_5$)—, —N($R_5$)S($O_2$)—, —C($R_3R_4$)S($O_2$)—, or —S($O_2$)C($R_3R_4$)—; D is optionally substituted aryl or heterocycle; $R_1$ is hydrogen or optionally substituted alkyl, alkyl-aryl, alkyl-heterocycle, aryl, or heterocycle; $R_2$ is hydrogen or optionally substituted alkyl, alkyl-aryl, alkyl-heterocycle, aryl, or heterocycle; $R_3$ is hydrogen, alkoxy, amino, cyano, halogen, hydroxyl, or optionally substituted alkyl; $R_4$ is hydrogen, alkoxy, amino, cyano, halogen, hydroxyl, or optionally substituted alkyl or aryl; each $R_5$ is independently hydrogen or optionally substituted alkyl or aryl; and n is 0-3. Such TPH1 inhibitors are described in International Patent Publication WO 2007/089335, where they are disclosed as being useful for treatment of carcinoid syndrome as well as gastrointestinal diseases and disorders.

In certain embodiments, the agent is a TPH1 inhibitor having the structure:

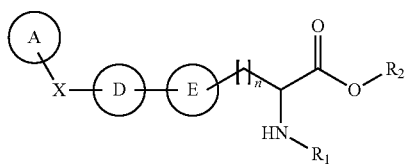

and pharmaceutically acceptable salts and solvates thereof, wherein: A is optionally substituted cycloalkyl, aryl, or heterocycle; X is a bond (i.e., A is directly bound to D), —O—, —S—, —C(O)—, —C(R4)=, =C($R_4$)—, —C($R_3R_4$)—, —C($R_4$)=C($R_4$)—, —C≡—, —N($R_5$)—, —N($R_5$)C(O)N($R_5$)—, —C($R_3R_4$)N($R_5$)—, —N($R_5$)C($R_3R_4$)—, —ONC($R_3$)—, —C($R_3$)NO—, —C($R_3R_4$)O—, —OC($R_3R_4$)—, —S($O_2$)—, —S($O_2$)N($R_5$)—, —N($R_5$)S($O_2$)—, —C($R_3R_4$)S($O_2$)—, or —S($O_2$)C($R_3R_4$)—; D is optionally substituted aryl or heterocycle; E is optionally substituted aryl or heterocycle; $R_1$ is hydrogen or optionally substituted alkyl, alkyl-aryl, alkyl-heterocycle, aryl, or heterocycle; $R_1$ is hydrogen or optionally substituted alkyl, alkyl-aryl, alkyl-heterocycle, aryl, or heterocycle; $R_3$ is hydrogen, alkoxy, amino, cyano, halogen, hydroxyl, or optionally substituted alkyl; $R_4$ is hydrogen, alkoxy, amino, cyano, halogen, hydroxyl, or optionally substituted alkyl or aryl; each $R_5$ is independently hydrogen or optionally substituted alkyl or aryl; and n is 0-3. Such TPH1 inhibitors are described in International Patent Publication WO 2007/089335, where they are disclosed as being useful for treatment of carcinoid syndrome as well as gastrointestinal diseases and disorders.

In the compounds disclosed in the two paragraphs immediately above:

"cycloalkyl" means a cyclic hydrocarbon having from 1 to 20 (e.g., 1 to 10 or 1 to 4) carbon atoms. Cycloalkyl moieties may be monocyclic or multicyclic, and examples include cyclopropyl, cyclobutyl, cyclopentyl, cyclohexyl, and adamantyl;

"aryl" means an aromatic ring or an aromatic or partially aromatic ring system composed of carbon and hydrogen atoms. An aryl moiety may comprise multiple rings bound or fused together. Examples of aryl moieties include anthracenyl, azulenyl, biphenyl, fluorenyl, indan, indenyl, naphthyl, phenanthrenyl, phenyl, 1,2,3,4-tetrahydro-naphthalene, and tolyl;

"heterocycle" refers to an aromatic, partially aromatic or non-aromatic monocyclic or polycyclic ring or ring system comprised of carbon, hydrogen and at least one heteroatom (e.g., N, O or S). A heterocycle may comprise multiple (i.e., two or more) rings fused or bound together. Heterocycles include heteroaryls. Examples include benzo[1,3]dioxolyl, 2,3-dihydro-benzo[1,4]dioxinyl, cinnolinyl, furanyl, hydantoinyl, morpholinyl, oxetanyl, oxiranyl, piperazinyl, piperidinyl, pyrrolidinonyl, pyrrolidinyl, tetrahydrofuranyl, tetrahydropyranyl, tetrahydropyridinyl, tetrahydropyrimidinyl, tetrahydrothiophenyl, tetrahydrothiopyranyl and valerolactamyl;

"alkyl" means a straight chain, branched and/or cyclic ("cycloalkyl") hydrocarbon having from 1 to 20 (e.g., 1 to 10 or 1 to 4) carbon atoms. Examples of alkyl groups include methyl, ethyl, propyl, isopropyl, n-butyl, t-butyl, isobutyl, pentyl, hexyl, isohexyl, heptyl, 4,4-dimethylpentyl, octyl, 2,2,4-trimethylpentyl, nonyl, decyl, undecyl and dodecyl. Cycloalkyl moieties may be monocyclic or multicyclic, and examples include cyclopropyl, cyclobutyl, cyclopentyl, cyclohexyl, and adamantyl. Additional examples of alkyl moieties have linear, branched and/or cyclic portions (e.g., 1-ethyl-4-methyl-cyclohexyl). The term "alkyl" includes saturated hydrocarbons as well as alkenyl and alkynyl moieties;

"alkyl-aryl" means an alkyl moiety bound to an aryl moiety;

"alkyl-heteroaryl" means an alkyl moiety bound to a heteroaryl moiety;

alkoxy" means an —O-alkyl group. Examples of alkoxy groups include —OCH₃, —OCH₂CH₃, —O(CH₂)₂CH₃, —O(CH₂)₃CH₃, —O(CH₂)₄CH₃, and —O(CH₂)₅CH₃;

In certain embodiments, the agent is a TPH1 inhibitor having the structure:

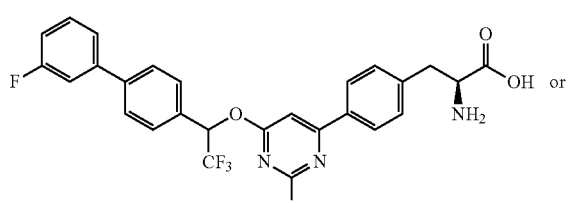

LP-533401

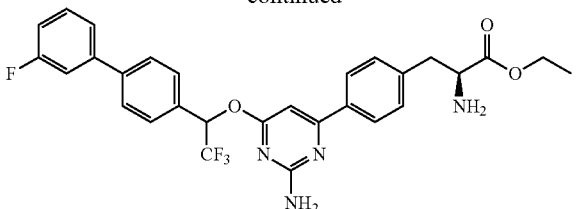

LP-615819

LP-533401 and LP-615819 are described in Liu et al., J. Pharmacol. Exp. Ther., 2008, Jan. 11 [Epub ahead of print] #132670, incorporated herein by reference in its entirety. LP-615819 is a prodrug (i.e., the ethyl ester) of LP-533401. As described in Liu et al., both LP-533401 and LP-615819 were administered to mice twice per day over a 3-4 day period in amounts of from about 30-90 mg/kg. Serotonin levels in the small intestine were significantly lowered after just six consecutive doses, while brain-derived serotonin was unchanged. Even though LP-533401 inhibits TPH2 as effectively as TPH1, it did not cross the blood-brain barrier in vivo, and therefore did not cause a decrease in brain-derived serotonin. Liu et al. disclosed that LP-533401 and LP-615819 may be useful for treating chemotherapy-induced emesis and irritable bowel syndrome.

LP-533401 and LP-615819 selectively reduce peripheral as opposed to brain-derived serotonin. In animal studies, LP-533401 reduced serotonin in the GI tract to less than about ⅔ normal levels using 135 mg/kg, po, qd. The effect followed a dose response curve. In the amounts administered to mice, brain serotonin levels were not affected. Lexicon Pharmaceuticals Incorporated developed these. TPH1 inhibitors specifically to treat diarrhea or irritable bowel syndrome. LP-533401 is presently being evaluated in Phase I clinical trials by Lexicon Pharmaceuticals. In a single dose regimen, 250 mg to 2,000 mg/day was administered orally. LP-533401 was also administered in multiple doses orally in amounts from 250-1,000 mg/day. In one format, the drug was given as a 500 mg dose twice per day or as a 500 mg dose four times per day for over 14 days. Infrequent adverse events were reported at all dose levels. These TPH1 inhibitors can be used in the present invention for treating or preventing low bone mass diseases including osteoporosis and osteoporosis pseudoglioma.

Various other TPH1 inhibitors related to LP-533401 and LP-615819, including multicyclic amino acid derivatives, are described in U.S. Patent Application Publication 2007/191370, and in related applications including International Patent Publication WO 2007/089335, which references are incorporated herein by reference in their entirety. These inhibitors can also be used in the methods of the present invention to treat or prevent low bone mass diseases.

In certain embodiments of the invention, a therapeutically effective amount of one or more of the compounds described in the preceding paragraphs is administered alone or in combination with other compounds that are known to increase bone mass to a subject who has or is at risk of developing a low bone mass disease in order to treat or prevent such disease.

The efficacy of low bone density therapy by administering TPH1 inhibitors can be monitored by measuring bone density changes before and over time after treatment to determine drug efficacy.

The present invention provides a method of preventing or treating a low bone mass disease in a patient known or suspected to be in need of such prevention or treatment comprising administering to the patient a therapeutically effective amount of serotonin receptor antagonist.

In certain embodiments, the serotonin receptor antagonist is an HT1B, HT2A or HT2B receptor antagonist. In preferred embodiments, the serotonin receptor antagonist is an HT1B antagonist.

The serotonin receptor antagonist may be one of the many known antagonists of peripheral serotonin receptors HT1B, HT2A or HT2B that are present on osteoblasts. Antagonists that are selective for HT1B, HT2A or HT2B receptors are preferred. The efficacy of low bone density therapy by administering HT1B, HT2A or HT2B antagonists can be monitored by measuring bone density changes before and over time after treatment to determine drug efficacy. Diseases associated with low bone mass can be treated with HT1B antagonists such as those listed in Table 3 below.

TABLE 3

| | |
|---|---|
| selective 5-HT1B antagonist GR 55562 | Mlinar and Corradetti, Neurosci., 2003, 18: 1559-1571 |
| elzasonan | U.S. Patent Application |
| AZD1134 | Publication 2005/0203130 |
| AR-A2 | |
| trazodone hydrochloride (antidepressant) | U.S. Pat. No., 7,198,914 |
| highly selective 5-HT 1B antagonist (SB216641) | U.S. Patent Application Publication 2006/0135415 |
| the selective antagonist at terminal 5-HT$_{1B}$ receptors, N-[3-(2-dimethylamino) ethoxy-4-methoxyphenyl]-2'-methyl-4'-(5-methyl-1,2,4-oxadiazol-3-yl)-(1,1'-biphenyl)-4-carboxamide (SB216641, 0.1-0.8 mg/kg) | Rojas-Corrales et al., Eur. J. Pharmacol., 511: 21-26 |
| GR 127,935 Mixed HT1B/1D antagonist | Naunyn Schmiedebergs Arch. Pharmacol., 1997, 355: 423-430; Wurch, et al., British J. Pharmacol., 1997, 120: 153-159 |
| Cyanopindolol GR 125,743 Methiothepin ketanserin | J. Neurochem., 2000, 75: 2113-2122 2'-Methyl-4-(5-methyl-[1,2,4]oxadiazol-3-yl)-biphenyl-4-carboxylic acid [4-methoxy-3-(4-methyl-piperazin-1-yl)-phenyl]amide (GR 127,935), ketanserin and methiothepin and each behaved as silent, competitive antagonists at rb 5-HT1B receptors British Journal of Pharmacology (1997) 120, 153 ± 159 |
| ICS 205-930 (Sandoz) is a selective antagonist at 5-hydroxytryptamine3 receptors and exerts marked effects on gastrointestinal motility in animalsGut specific | Br J Clin Pharmacol. 1989 September; 28(3): 315-322 |
| pindolol a beta-adrenoceptor blocker/5-hydroxytryptamine$_{1A/1B}$ receptor antagonist | Pindolol is also a nonselective beta blocker; rapidly and well absorbed from the GI tract |
| AR-A000002 - A Novel Selective 5-HT$_{1B}$ Antagonist anxiolytic and antidepressant potential of the selective 5-HT$_{1B}$ antagonist, AR-A000002 ((R)-N-[5-Methyl-8-(4-methylpiperazin-1-yl)-1,2,3,4-tetrahydro-2-naphthyl]-4-morpholinobenzamide). AR-A000002 functions as a 5-HT$_{1B}$ antagonist in vivo | Journal of Pharmacology And Experimental Therapeutics Fast Forward First published on November 25, 2002; |
| cyanopindolol, 5-HT-moduline and methiothepin | Daws, et al., Neuroscience Letters, 1999, 266: 165-168; Daws, et al., J. Neurochem., 2000, 75: 2113-2122 |
| GR 55562, a selective 5-HT1B antagonist selective 5-HT$_{1B}$ receptor antagonist 3-[3-(dimethylamino)propyl]-4-hydroxy-N-[4-(4-pyridinyl)phenyl]benzamide dihydrochloride (GR 55562; K$_B$ ≈100 nM) | British Journal of Pharmacology (2003) 138, 71-80 |
| SB224289 | Brain Res. 2004 May 8; 1007(1-2): 86-97 |
| SB 216641 | Roca-Vinardell et al., Anesthesiology, 2003,98: 741-747 |
| Nonselective 5-HT(1B/D) receptor antagonists such as ketanserin, ritanserin and methiothepin | |

In certain embodiments, the agent that increases peripheral serum serotonin levels is a small organic molecule, an antibody, antibody fragment, a protein, or polypeptide.

The present invention also provides a method of preventing or treating a low bone mass disease in a patient known or suspected to be in need of such prevention or treatment comprising administering to the patient both a TPH1 inhibitor and a serotonin receptor antagonist.

In certain embodiments, the TPH1 inhibitor and the serotonin receptor antagonist are administered together in a single pharmaceutical composition. In other embodiments, the TPH1 inhibitor and the serotonin receptor antagonist are administered in separate pharmaceutical compositions.

In certain embodiments of the methods described herein, the low bone mass disease is osteoporosis, osteoporosis pseudoglioma syndrome (OPPG), osteopenia, osteomalacia, renal osteodystrophy, faulty bone formation, faulty bone resorption, Paget's disease, bone fracture, broken bones, or bone metastasis. In preferred embodiments, the low bone mass disease is osteoporosis.

The amount of therapeutic agent to be used depends on many factors, as discussed herein. However, in humans, for example, the amount ranges from about 1 mg/day to about 2 g/day; preferably from about 15 mg/day to about 500 mg/day; or from about 20 mg/day to about 250 mg/day; or from about 40 mg/day to about 100 mg/day. Other preferred dosages include about 2 mg/day, about 5 mg/day, about 10 mg/day, about 15 mg/day, about 20 mg/day, about 25 mg/day, about 30 mg/day, about 40 mg/day, about 50 mg/day, about 60 mg/day, about 70 mg/day, about 80 mg/day, about 90 mg/day, about 100 mg/day, about 125 mg/day, about 150 mg/day, about 175 mg/day, about 200 mg/day, about 250 mg/day, about 300 mg/day, about 350 mg/day, about 400 mg/day, about 500 mg/day, about 600 mg/day, about 700 mg/day, about 800 mg/day, and about 900 mg/day. Routine experimentation will determine the appropriate value for each patient by monitoring the compound's effect on serum serotonin levels, which can be frequently and easily monitored. The agent can be administered once or multiple times per day. Serum serotonin levels can be monitored before and during therapy to determine the appropriate amount of TPH1 inhibitor to administer to lower serum serotonin levels or bring serum serotonin levels to normal and to maintain normal levels over extended periods of time. In a preferred embodiment, a patient is tested to determine if his/her serum serotonin levels are significantly elevated above normal levels (about 25% above) before administering treatment with TPH1 inhibitors and/or HT1B, HT2A or HT2B receptor antagonists. The frequency of administration may vary from a single dose per day to multiple doses per day. Preferred routes of administration include oral, intravenous and intraperitoneal, but other forms of administration may be chosen as well.

Another embodiment of the present invention is directed to pharmaceutical formulations of TPH1 inhibitors or serotonin synthesis inhibitors combined with SSRIs for administration to a subject being treated with long term SSRI administration, in order to prevent bone loss or to maintain or increase normal bone mass.

In certain embodiments, the therapeutic agents of the invention act selectively on peripheral serotonin or are administered in an amount that decreases serum serotonin without increasing brain-derived serotonin.

In other embodiments, the TPH1 inhibitors and serotonin receptor antagonists are formulated and administered together with bisphosphonates such as FOSAMAX® (alendronate sodium), FOSAMAX PLUS D™ (alendronate sodium/cholecalciferol) or other bone building drugs, vitamins or minerals to potentiate their effects on increasing bone mass.

Monitoring the therapeutic efficacy of TPH1 inhibitors and serotonin synthesis inhibitors is straightforward, as one can administer the inhibitors in an amount and for a duration that reduces peripheral serum serotonin levels, and over time increases bone mass. Both serum serotonin and bone mass can be easily measured. Example 1 provides the details of one immunoassay for monitoring the level of serum serotonin. Example 3 provides further assays for serum serotonin that may be used. Monitoring serum serotonin is simple and can be done frequently during the course of therapy to establish the appropriate dose for each patient. Any method known in the art for assaying serum serotonin can be used. Increased bone mass can be measured as described herein using various means of measuring bone density and markers of bone growth or can be measured by other methods known in the art.

In another embodiment, low bone mass diseases are treated by administering anti-serotonin antibodies or antibody fragments, preferably by intravenous or intraperitoneal injections. Such antibodies will not cross the blood brain barrier, and will neutralize serotonin, thereby preventing it from reducing bone mass. Antibodies or antibody fragments that recognize and inactivate TPH1 or a serotonin receptor (e.g., HT1B), and thus lower serum serotonin levels, can also be used in the present invention.

The terms "antibody" and "antibodies" include polyclonal antibodies, monoclonal antibodies, humanized or chimeric antibodies, single chain Fv antibody fragments, Fab fragments, and F(ab')$_2$ fragments. Polyclonal antibodies are heterogeneous populations of antibody molecules that are specific for a particular antigen, while monoclonal antibodies are homogeneous populations of antibodies to a particular epitope contained within an antigen. Monoclonal antibodies are particularly useful in the present invention.

Antibody fragments that have specific binding affinity for a target of interest (e.g., TPH1 or HT1B) can be generated by known techniques. Such antibody fragments include, but are not limited to, F(ab')$_2$ fragments that can be produced by pepsin digestion of an antibody molecule, and Fab fragments that can be generated by reducing the disulfide bridges of F(ab')$_2$ fragments. Alternatively, Fab expression libraries can be constructed. See, for example, Huse et al., 1989, Science 246:1275-1281. Single chain Fv antibody fragments are formed by linking the heavy and light chain fragments of the Fv region via an amino acid bridge (e.g., 15 to 18 amino acids), resulting in a single chain polypeptide. Single chain Fv antibody fragments recognizing a target of interest can be produced through standard techniques, such as those disclosed in U.S. Pat. No. 4,946,778.

Once produced, antibodies or fragments thereof can be tested for recognition of the target of interest by standard immunoassay methods including, for example, enzyme-linked immunosorbent assay (ELISA) or radioimmunoassay assay (RIA). See, *Short Protocols in Molecular Biology*, eds. Ausubel et al., Green Publishing Associates and John Wiley & Sons (1992).

The amount of antibody or antibody fragment to administer will depend, inter alia, on how high the level of peripheral serotonin is compared to normal levels. Monoclonal and polyclonal anti-serotonin antibodies known in the art, or newly designed, can be used and can be administered as a single therapy or as combination therapy with TPH1 inhibitors and/or HT1B antagonists.

U.S. Provisional Patent Application Ser. No. 60/976,403, filed Sep. 28, 2007, and incorporated by reference herein in its entirety, discloses that brain-derived serotonin increases bone mass and decreases sympathetic tone. Another embodiment of the present invention for treating or preventing low bone mass diseases is directed to methods for treating or preventing low bone mass by administering agents that decrease sympathetic tone, such as beta blockers, together with a TPH1 inhibitor, serotonin synthesis inhibitor, HT1B, HT2A or HT2B antagonist and/or anti-serotonin antibodies, either in a single formulation or separately. The use of any compound that decreases sympathetic tone comes within the scope of the invention. Preferably the compound is a beta-2 receptor antagonist, many of which are described in the art. Among the beta blockers that can be used are three beta-2 specific blockers that can be used to reduce sympathetic tone and increase bone mass, alone or in combination with other therapeutic agents described herein: IPS339, ICI118,551, and Sandoz L1 32-468 (Br. J. Ophthalmol. 1984 April; 68(4): 245-247). Butaxamine is also a beta-2 blocker that may be used in the present invention. Non-selective beta blockers include: metipranolol, nadol (a beta-specific sympatholytic which non-selectively blocks beta-2 adrenergic receptors); oxprenolol (a lipophilic beta blocker which passes the blood-brain barrier more easily than water soluble beta blockers), penbutolol, pindolol (a beta blocker that acts on serotonin 5-HT1A receptors in the brain, resulting in increased postsynaptic serotonin concentrations), and propranolol (known to readily cross the blood-brain barrier, timolol and sotalol. The beta blockers can be administered together with agents that directly or indirectly increase brain-derived serotonin, including HT2C receptor agonists, agents that increase TPH2 activity or expression, and agents that specifically decrease reuptake of BDS.

Certain other embodiments of the invention are directed to a pharmaceutical composition that includes a TPH1 inhibitor; HT1B, HT2A or HT2B antagonist; and/or anti-serotonin antibodies, individually or in combination. More than one type of TPH1 inhibitor, HT1B, HT2A or HT2B antagonist, or anti-serotonin antibody can be administered together for treating diseases associated with low bone mass, and certain embodiments include corresponding pharmaceutical compositions comprising these compounds. In other embodiments, the different types of agents are administered separately at one or more times on the same day, or over a period of days; sometimes alternating administration of the various respective agents.

Some embodiments are directed to pharmaceutical compositions for treating or preventing anxiety or depression that include both SSRIs and drugs that reduce the level of serum serotonin (e.g., TPH1 inhibitors or HT1B antagonists) in order to prevent patients who take serotonin reuptake inhibitors from developing osteoporosis. These preparations would permit the SSRIs to elevate brain-derived serotonin to treat anxiety without increasing peripheral serotonin, which can cause low bone mass diseases like osteoporosis.

Elevated brain-derived serotonin increases bone mass by acting through HT2C receptors on target neurons in the hypothalamus. Thus, some embodiments of the present invention include administering combination drug therapy using pharmaceuticals that decrease peripheral serotonin and increase brain-derived serotonin. For example, an HT2C agonist may be combined with a TPH1 inhibitor or an HT1B antagonist.

Diseases associated with abnormally high bone mass such as high bone mass syndrome can be treated by administering serotonin, serotonin reuptake inhibitors, TPH1 activators, TPH2 inhibitors, serontonin receptor agonists, or combinations thereof, to increase serum serotonin, which will in turn decrease bone mass. HT1B agonists, or other serotonin receptor agonists, can be used to activate the receptors on osteoblasts to decrease bone mass. TPH1 inhibitors, HT1B agonists, HT2A agonists or HT2B agonists can be administered together with serotonin. Thus, certain embodiments of the present invention are directed to methods for treating high bone mass disease by administering serotonin, preferably orally, intraperitoneally or intravenously, alone or together with TPH1 inhibitors, HT1B agonists, HT2A agonists or HT2B agonists to decrease bone mass, preferably to normal levels.

In certain embodiments, the methods of the present invention comprise the step of identifying a patient in need of therapy for a bone disease. Thus, the present invention provides a method comprising:

(a) identifying a patient in need of therapy for a bone disease;

(b) administering to the patient a therapeutically effective amount of an agent that increases or decreases serum serotonin levels.

In certain embodiments, the present invention provides a method comprising:

(a) identifying a patient in need of therapy for a low bone mass disease;

(b) administering to the patient a therapeutically effective amount of an agent that decreases serum serotonin levels.

In certain embodiments, the present invention provides a method comprising:

(a) identifying a patient in need of therapy for a high bone mass disease;

(b) administering to the patient a therapeutically effective amount of an agent that increases serum serotonin levels.

The present invention encompasses the use of a TPH1 inhibitor or a serotonin receptor antagonist (e.g., an HT1B antagonist) for the manufacture of a medicament for preventing or treating a bone disease (e.g., a low bone mass disease such as osteoporosis). The present invention encompasses the use of a TPH1 inhibitor or a serotonin receptor antagonist (e.g., an HT1B antagonist) for preventing or treating a bone disease (e.g., a low bone mass disease such as osteoporosis).

Pharmaceutical Compositions

Therapeutic agents such as the TPH1 inhibitors, serotonin receptor antagonists, serotonin receptor agonists, SSRIs, and beta blockers described herein may be formulated into pharmaceutical compositions. The therapeutic agents may be present in the pharmaceutical compositions in the form of salts of pharmaceutically acceptable acids or in the form of bases. The therapeutic agents may be present in amorphous form or in crystalline forms, including hydrates and solvates. Preferably, the pharmaceutical compositions comprise a therapeutically effective amount of a TPH1 inhibitor or serotonin receptor antagonist.

Pharmaceutically acceptable derivatives of any of the TPH1 inhibitors, serotonin receptor antagonists, or serotonin receptor agonists described herein come within the scope of the invention. A "pharmaceutically acceptable derivative" of a TPH1 inhibitor, serotonin receptor antagonist, or serotonin receptor agonist means any non-toxic derivative of a TPH1 inhibitor, serotonin receptor antagonist, or serotonin receptor agonist described herein that, upon administration to a recipient, exhibits that same or similar biological activity with respect to reducing or increasing serum serotonin expression as the TPH1 inhibitor, serotonin receptor antagonist, or serotonin receptor agonists described herein.

Pharmaceutically acceptable salts of the therapeutic agents described herein for use in treating or preventing bone diseases associated with abnormally high or abnormally low bone mass, include those salts derived from pharmaceutically acceptable inorganic and organic acids and bases. Examples of suitable acid salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, oxalate, palmoate, pectinate, persulfate, 3-phenylpropionate, phosphate, picrate, pivalate, propionate, salicylate, succinate, sulfate, tartrate, thiocyanate, tosylate and undecanoate salts. Other acids, such as oxalic, while not in themselves pharmaceutically acceptable, may be employed in the preparation of salts useful as intermediates in obtaining the compounds of the invention and their pharmaceutically acceptable acid addition salts.

Salts derived from appropriate bases include alkali metal (e.g., sodium and potassium), alkaline earth metal (e.g., magnesium), ammonium and $N^+(C_{1-4}\text{ alkyl})_4$ salts. This invention also envisions the quaternization of any basic nitrogen-containing groups of the therapeutic agents disclosed herein. Water or oil-soluble or dispersible products may be obtained by such quaternization.

The therapeutic agents of the present invention are also meant to include all stereochemical forms of the therapeutic agents (i.e., the R and S configurations for each asymmetric center). Therefore, single enantiomers, racemic mixtures, and diastereomers of the therapeutic agents are within the scope of the invention. Also within the scope of the invention are steric isomers and positional isomers of the therapeutic agents. The therapeutic agents of the present invention are also meant to include compounds which differ only in the presence of one or more isotopically enriched atoms. For example, therapeutic agents in which a molecule of hydrogen is replaced by deuterium or tritium, or the replacement of a carbon molecule by $^{13}C$- or $^{14}C$-enriched carbon are within the scope of this invention.

In a preferred embodiment, the therapeutic agents of the present invention are administered in a pharmaceutical composition that includes a pharmaceutically acceptable carrier, adjuvant, or vehicle. The term "pharmaceutically acceptable carrier, adjuvant, or vehicle" refers to a non-toxic carrier, adjuvant, or vehicle that does not destroy or significantly diminish the pharmacological activity of the compound with which it is formulated. Pharmaceutically acceptable carriers, adjuvants or vehicles that may be used in the compositions of this invention encompass any of the standard pharmaceutically accepted liquid carriers, such as a phosphate-buffered saline solution, water, as well as emulsions such as an oil/water emulsion or a triglyceride emulsion. An example of an acceptable triglyceride emulsion useful in the intravenous and intraperitoneal administration of the compounds is the triglyceride emulsion commercially known as INTRALIPID RTM®. Solid carriers may include excipients such as starch, milk, sugar, certain types of clay, stearic acid, talc, gums, glycols, or other known excipients. Carriers may also include flavor and color additives or other ingredients.

In the practice of the invention, the pharmaceutical compositions of the present invention are preferably administered orally. However, the pharmaceutical compositions may be administered parenterally, by inhalation spray, topically, rectally, nasally, buccally, vaginally or via an implanted reservoir. Preferably, the pharmaceutical compositions are administered orally, intraperitoneally or intravenously. Sterile injectable forms of the pharmaceutical compositions may be aqueous or oleaginous suspensions. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutical compositions of this invention may be orally administered in any orally acceptable dosage form including, but not limited to, solid forms such as capsules and tablets. In the case of tablets for oral use, carriers commonly used include microcrystalline cellulose, lactose and corn starch. Lubricating agents, such as magnesium stearate, are also typically added. When aqueous suspensions are required for oral use, the active ingredient may be combined with emulsifying and suspending agents. If desired, certain sweetening, flavoring or coloring agents may also be added.

The pharmaceutical compositions of this invention may also be administered by nasal aerosol or inhalation. Such pharmaceutical compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Should topical administration be desired, it can be accomplished using any method commonly known to those skilled in the art and includes but is not limited to incorporation of the pharmaceutical composition into creams, ointments, or transdermal patches.

Where the pharmaceutical compositions contain both agents that act peripherally like HT1B antagonists or TPH1 inhibitors and agents that act centrally like HT2C agonists, the compositions can be formulated to increase delivery of the centrally acting therapeutic agents to the central nervous system. If a compound having therapeutic utility does not easily cross the blood brain barrier, it can be modified using various methods in medicinal chemistry known in the art that attach various side groups to improve permeability through the blood brain barrier.

Serotonin receptor antagonists (e.g., HT1B receptor antagonists) can be derivatized or otherwise designed to enhance uptake by bone, using medicinal chemistry methods known in the art.

The TPH1 inhibitors and HT1B antagonists of the present invention can be derivatized by the formation of a reversible linkage with one or more suitable groups to yield "pro-drugs," i.e., chemical derivatives that, after absorption by the host, are converted into the parent compound. Liberation of the parent compound may be by chemical hydrolysis or enzymatic attack. A derivative or pro-drug can have enhanced permeability for the target organ. In the case of TPH1 inhibitors, the target organ is the duodenum where 95% of peripheral serotonin is made. HT1B antagonists could be formulated to have enhanced penetration of bone to reach the osteoblast target. The prodrug has an enhanced permeability according to the present invention if, after administration of the pro-drug or derivative thereof to a living organism, a higher amount of the compound reaches the target organ, resulting in a higher level of effective agent, as compared to administration of the base compound without derivatization.

The amount of the therapeutic agents of the present invention that may be combined with the carrier materials to produce a pharmaceutical composition in a single dosage form will vary depending upon the host treated and the particular mode of administration. It should be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician as well as the severity of the particular disease being treated. Despite their variety, accounting for these factors in order to select an appropriate dosage or treatment regimen would require no more than routine experimentation.

Additional therapeutic agents, which are normally administered to treat bone diseases associated with abnormally high or abnormally low bone mass, may also be present in the pharmaceutical compositions of this invention. As used herein, additional therapeutic agents that are normally administered to treat a particular disease, or condition, are known as "appropriate for the disease, or condition, being treated." Examples of appropriate agents for osteoporosis include FOSAMAX®, other bisphosphonates, FORTEO® (parathyroid hormone) and beta-blockers. Those additional agents may be administered separately from the therapeutic agents of the invention, as part of a multiple dosage regimen. Alternatively, those agents may be part of a single dosage form, mixed together with the therapeutic agents of the invention in a single pharmaceutical composition. If administered as part of a multiple dosage regime, the two active agents may be administered simultaneously, sequentially or within a period of time from one another. The amount of both the therapeutic agent of the invention and the additional therapeutic agent (in those compositions which comprise an additional therapeutic agent as described above) that may be combined with the carrier materials to produce a single dosage form will vary depending upon the host treated and the particular mode of administration as well as on the nature of the therapeutic agent of the invention and the additional therapeutic agent.

TPH1 inhibitors and the other therapeutic agents described herein (e.g., HT1B antagonists, HT2C agonists) may be proteins or polypeptides, as well as any biologically active fragment, epitope, modification, derivative or variant thereof. Biologically active fragments of a protein or polypeptide are those fragments of the protein or polypeptide exhibiting activity similar to, but not necessarily identical to, an activity of the entire protein or polypeptide. The biological activity of the fragments may include an improved desired activity, or a decreased undesirable activity. Variants include (i) substitutions of one or more of the amino acid residues, where the substituted amino acid residues may or may not be one encoded by the genetic code, or (ii) substitution with one or more of amino acid residues having a substituent group, or (iii) fusion of the mature polypeptide with another compound, such as a compound to increase the stability and/or solubility of the polypeptide (e.g., polyethylene glycol), or other molecule that facilitates transport through stomach (if administered orally) or through the endothelium (if administered intravenously), and (iv) fusion of the polypeptide with additional amino acids, such as an IgG Fc peptide, or a leader or secretary sequence, or a sequence facilitating purification. Such variant polypeptides are deemed to be within the scope of the present invention if they retain therapeutic efficacy.

"Amino acid residue" refers to an amino acid which is part of a polypeptide. The amino acid residues described herein are preferably in the L isomeric form. However, residues in the D isomeric form can be substituted for any L-amino acid residue, as long as the desired functional property is retained by the polypeptide. $NH_2$ refers to the free amino group present at the amino terminus of a polypeptide. COOH refers to the free carboxyl group present at the carboxyl terminus of a polypeptide. "Amino acid residue" is broadly defined to include the 20 amino acids commonly found in natural proteins, as well as modified and unusual amino acids, such as those referred to in 37 C.F.R. Sections 1.821-1.822, the entire contents of which are hereby incorporated by reference as if fully set forth herein. In a polypeptide or protein, suitable conservative substitutions of amino acids are known to those of skill in this art and can be made generally without altering the biological activity of the resulting molecule. Those of skill in the art recognize that, in general, single amino acid substitutions in non-essential regions of a polypeptide do not substantially alter biological activity (see, e.g., Watson et al. Molecular Biology of the Gene, 4th Edition, 1987, The Benjamin/Cummings Pub. Co., p. 224).

Examples of conservative substitutions are the replacements, one for another, among the hydrophobic amino acids Ala, Val, Leu, and Ile; interchange of the hydroxyl residues Ser and Thr; exchange of the acidic residues Asp and Glu; substitution between the amide residues Asn and Gln; exchange of the basic residues Lys, His and Arg; replacements among the aromatic residues Phe, Trp and Tyr; exchange of the polar residues Gln and Asn; and exchange of the small residues Ala, Ser, Thr, Met, and Gly.

Acylation of the N-terminal amino group can be accomplished using a hydrophilic compound, such as hydroorotic acid or the like, or by reaction with a suitable isocyanate, such as methylisocyanate or isopropylisocyanate, to create a urea moiety at the N-terminus. Other agents can also be N-terminally linked that will increase the duration of action of the variant as known in this art.

Reductive amination is the process by which ammonia is condensed with aldehydes or ketones to form imines which are subsequently reduced to amines. For therapeutic agents bearing one or more amino groups, reductive amination is a potentially useful method for conjugation to poly(ethylene glycol) (PEG). Covalent linkage of PEG to drug molecules results in water-soluble conjugates with altered bioavailability, pharmacokinetics, immunogenic properties, and biological activities. For drugs bearing one or more amino groups, reductive amination is a potentially useful method for conjugation to PEG (Bentley et al., *J. Pharm. Sci.* 1998 November; 87(11):1446-1449).

As is also well known, polypeptides are not always entirely linear. For instance, polypeptides may be branched as a result of ubiquitination, and they may be circular, with or without branching, generally as a result of post-translational events, including natural processing events and events brought about by human manipulation which do not occur naturally. Circular, branched and branched circular polypeptides for use in the present invention may be synthesized by non-translational natural processes and by synthetic methods.

Modifications can occur anywhere in a protein or polypeptide for use in the present invention, including the peptide backbone, the amino acid side-chains and the amino or carboxyl termini. Blockage of the amino or carboxyl group in a polypeptide, or both, by a covalent modification, is common in naturally-occurring and synthetic polypeptides. For instance, the amino-terminal residue of polypeptides made in *E. coli*, prior to proteolytic processing, almost invariably will be N-formylmethionine.

The modifications can be a function of how the protein is made. For recombinant polypeptides used in the present invention, for example, the modifications will be determined by the host cell posttranslational modification capacity and the modification signals in the polypeptide amino acid sequence. Accordingly, when glycosylation is desired, a polypeptide should be expressed in a glycosylating host, generally a eukaryotic cell. Insect cells often carry out the same posttranslational glycosylations as mammalian cells, and, for this reason, insect cell expression systems have been developed to efficiently express mammalian proteins having native patterns of glycosylation. Accordingly, the use of insect systems in the present invention is contemplated. Similar considerations apply to other modifications besides glycosylation. The same type of modification may be present in the same or varying degree at several sites in a given polypeptide. Also, a given polypeptide may contain more than one type of modification.

The following table illustrates some of the common modifications of proteins and polypeptides that may be used in the present invention.

TABLE 4

| Protein Modification | Description |
|---|---|
| Acetylation | Acetylation of N-terminus or ε-lysines. Introducing an acetyl group into a protein, specifically, the substitution of an acetyl group for an active hydrogen atom. |
| | A reaction involving the replacement of the hydrogen atom of a hydroxyl group with an acetyl group ($CH_3CO$) yields a specific ester, the acetate. Acetic anhydride is commonly used as an acetylating agent, which reacts with free hydroxyl groups. |
| | Acylation may facilitate addition of other functional groups. A common reaction is acylation of e.g., conserved lysine residues with a biotin appendage. |
| ADP-ribosylation | Covalently linking proteins or other compounds via an arginine-specific reaction. |
| Alkylation | Alkylation is the transfer of an alkyl group from one molecule to another. The alkyl group may be transferred as an alkyl carbocation, a free radical or a carbanion (or their equivalents). Alkylation is accomplished by using certain functional groups such as alkyl electrophiles, alkyl nucleophiles or sometimes alkyl radicals or carbene acceptors. A common example is methylation (usually at a lysine or arginine residue). |
| Amidation | Reductive amidation of the N-terminus. Methods for amidation are described in U.S. Pat. No. 4,489,159. |
| Carbamylation | Adding a carbamoyl group to a protein or polypeptide. |
| Carboxylation | Carboxylation typically occurs at the glutamate residues of a protein. Carboxylation may be catalyzed by a carboxylase enzyme (in the presence of Vitamin K - a cofactor). |
| Citrullination | Citrullination involves the addition of citrulline amino acids to the arginine residues of a protein, which is catalyzed by peptidylarginine deaminase enzymes (PADs). This generally converts a positively charged arginine into a neutral citrulline residue, which may affect the hydrophobicity of the protein (and can lead to unfolding). |
| Condensation of amines with aspartate or glutamate | Such reactions may be used, e.g., to attach a peptide to other proteins or to attach labels to proteins or polypeptides. |
| Covalent attachment of flavin | Flavin mononucleotide (FAD) may be covalently attached to serine and/or threonine residues. May be used, e.g., as a light-activated tag. |
| Covalent attachment of heme moiety | A heme moiety is generally a prosthetic group that consists of an iron atom contained in the center of a large heterocyclic organic ring, which is referred to as a porphyrin. The heme moiety may be used, e.g., as a tag for the peptide. |
| Attachment of a nucleotide or nucleotide derivative | May be used as a tag or as a basis for further derivatising a peptide. |
| Cross-linking | Cross-linking is a method of covalently joining two proteins. Cross-linkers contain reactive ends to specific functional groups (primary amines, sulfhydryls, etc.) on proteins or other molecules. Several chemical groups may be targets for reactions in proteins and peptides. For example, Ethylene glycol bis[succinimidylsuccinate, Bis[2-(succinimidooxycarbonyloxy)ethyl]sulfone, and Bis[sulfosuccinimidyl] suberate link amines to amines. |
| Cyclization | For example, cyclization of amino acids to create optimized delivery forms that are resistant to, e.g., aminopeptidases (e.g., formation of pyroglutamate, a cyclized form of glutamic acid). |
| Disulfide bond formation | Disulfide bonds in proteins are formed by thiol-disulfide exchange reactions, particularly between cysteine residues (e.g., formation of cystine). |
| Demethylation | See, e.g., U.S. Pat. No. 4,250,088 (Process for demethylation). |
| Formylation | The addition of a formyl group to, e.g., the N-terminus of a protein. See, e.g., U.S. Pat. Nos. 4,059,589, 4,801,742, and 6,350,902. |
| Glycosylation | Glycosylation may be used to add saccharides (or polysaccharides) to the hydroxy oxygen atoms of serine and |

TABLE 4-continued

| Protein Modification | Description |
|---|---|
| | threonine side chains (which is also known as O-linked Glycosylation). Glycosylation may also be used to add saccharides (or polysaccharides) to the amide nitrogen of asparagine side chains (which is also known as N-linked Glycosylation), e.g., via oligosaccharyl transferase. |
| GPI anchor formation | The addition of glycosylphosphatidylinositol to the C-terminus of a protein. GPI anchor formation involves the addition of a hydrophobic phosphatidylinositol group - linked through a carbohydrate containing linker (e.g., glucosamine and mannose linked to phosphoryl ethanolamine residue) - to the C-terminal amino acid of a protein. |
| Hydroxylation | A chemical process that introduces one or more hydroxyl groups (—OH) into a protein (or polypeptide). Hydroxylation reactions are typically catalyzed by hydroxylases. Proline is the principal residue to be hydroxylated in proteins, which occurs at the $C^\gamma$ atom, forming hydroxyproline (Hyp). In some cases, proline may be hydroxylated at its $C^\beta$ atom. Lysine may also be hydroxylated on its $C^\delta$ atom, forming hydroxylysine (Hyl). These three reactions are catalyzed by large, multi-subunit enzymes known as prolyl 4-hydroxylase, prolyl 3-hydroxylase and lysyl 5-hydroxylase, respectively. These reactions require iron (as well as molecular oxygen and α-ketoglutarate) to carry out the oxidation, and use ascorbic acid to return the iron to its reduced state. |
| Iodination | See, e.g., U.S. Pat. No. 6,303,326 for a disclosure of an enzyme that is capable of iodinating proteins or polypeptides. U.S. Pat. No. 4,448,764 discloses, e.g., a reagent that may be used to iodinate proteins. |
| ISGylation | Covalently linking a peptide to the ISG15 (Interferon-Stimulated Gene 15) protein, for, e.g., modulating immune response. |
| Methylation | Reductive methylation of protein amino acids with formaldehyde and sodium cyanoborohydride has been shown to provide up to 25% yield of N-cyanomethyl (—CH$_2$CN) product. The addition of metal ions, such as Ni$^{2+}$, which complex with free cyanide ions, improves reductive methylation yields by suppressing by-product formation. The N-cyanomethyl group itself, produced in good yield when cyanide ion replaces cyanoborohydride, may have some value as a reversible modifier of amino groups in proteins. Methylation may occur at the arginine and lysine residues of a protein, as well as the N- and C-terminus thereof. |
| Myristoylation | Myristoylation involves the covalent attachment of a myristoyl group (a derivative of myristic acid), via an amide bond, to the alpha-amino group of an N-terminal glycine residue. This addition is catalyzed by the N-myristoyltransferase enzyme. |
| Oxidation | Oxidation of cysteines.<br>Oxidation of N-terminal Serine or Threonine residues (followed by hydrazine or aminooxy condensations).<br>Oxidation of glycosylations (followed by hydrazine or aminooxy condensations). |
| Palmitoylation | Palmitoylation is the attachment of fatty acids, such as palmitic acid, to cysteine residues of proteins. Palmitoylation increases the hydrophobicity of a protein. |
| (Poly)glutamylation | Polyglutamylation occurs at the glutamate residues of a protein. Specifically, the gamma-carboxy group of a glutamate will form a peptide-like bond with the amino group of a free glutamate whose alpha-carboxy group may be extended into a polyglutamate chain. The glutamylation reaction is catalyzed by a glutamylase enzyme (or removed by a deglutamylase enzyme). Polyglutamylation has been carried out at the C-terminus of proteins to add up to about six glutamate residues. |
| Phosphopantetheinylation | The addition of a 4'-phosphopantetheinyl group. |
| Phosphorylation | A process for phosphorylation of a protein or peptide by contacting a protein or peptide with phosphoric acid in the presence of a non-aqueous apolar organic solvent and contacting the resultant solution with a dehydrating agent is disclosed e.g., in U.S. Pat. No. 4,534,894. Typically, phosphorylation occurs at the serine, threonine, and tyrosine residues of a protein. |
| Prenylation | Prenylation (or isoprenylation or lipidation) is the addition of hydrophobic molecules to a protein. Protein prenylation involves the transfer of either a farnesyl (linear grouping of |

TABLE 4-continued

| Protein Modification | Description |
|---|---|
| | three isoprene units) or a geranyl-geranyl moiety to C-terminal cysteine(s) of the target protein or polypeptide. |
| Proteolytic Processing | Processing, e.g., cleavage of a protein at a peptide bond. |
| Selenoylation | The exchange of, e.g., a sulfur atom in the peptide for selenium, using a selenium donor, such as selenophosphate. |
| Sulfation | Processes for sulfating hydroxyl moieties, particularly tertiary amines, are described in, e.g., U.S. Pat. No. 6,452,035. A process for sulfation of a protein or polypeptide by contacting the protein or polypeptide with sulfuric acid in the presence of a non-aqueous apolar organic solvent and contacting the resultant solution with a dehydrating agent is disclosed. |
| SUMOylation | Covalently linking a protein or polypeptide to a SUMO (small ubiquitin-related modifier) protein, for, e.g., stabilizing the peptide. |
| Transglutamination | Covalently linking other protein(s) or chemical groups (e.g., PEG) via a bridge at glutamine residues |
| tRNA-mediated addition of amino acids (e.g., arginylation) | For example, the site-specific modification (insertion) of an amino acid analog into a peptide. |
| Ubiquitination | The small peptide ubiquitin is covalently linked to, e.g., lysine residues of a protein. The ubiquitin-proteasome system can be used to carryout such reaction. See, e.g., U.S. Patent Application Publication 2007/0059731. |

Identifying Therapeutic Agents of the Present Invention

Inhibitors of TPH1 may be identified by any methods known in the art. In particular, inhibitors of TPH1 may be identified by a method comprising:

(a) providing a source of TPH1;

(b) exposing the source of TPH1 to L-tryptophan in the absence of a candidate compound;

(c) measuring the amount of 5-hydroxytryptophan produced by the source of TPH1 in the absence of the candidate compound;

(d) exposing the source of TPH1 to L-tryptophan in the presence of the candidate compound;

(e) measuring the amount of 5-hydroxytryptophan produced by the source of TPH1 in the presence of the candidate compound;

(f) where, if the amount of 5-hydroxytryptophan produced by the source of TPH1 in the presence of the candidate compound is less than the amount of 5-hydroxytryptophan produced by the source of TPH1 in the absence of the candidate compound, the candidate compound is a TPH1 inhibitor.

In certain embodiments, the method described above includes the further step of administering the TPH1 inhibitor identified in step (f) to a patient in need of therapy for a low bone mass disease.

"Less than" for the purpose of the herein-described methods of identifying therapeutic agents from a collection of candidate compounds refers to an amount that would not be attributed by those of skill in the art to normal variation seen in the method. Preferably, "less than" is at least about 10%, at least about 20%, at least about 50%, at least about 75%, or at least about 95% less than the amount observed in the absence of the candidate compound.

In certain embodiments, the source of TPH1 is an isolated TPH1 enzyme, preferably human. Isolated TPH1 can be produced by in vitro expression of TPH1, e.g., in a coupled in vitro transcription/translation system. Alternatively, the source of TPH1 may be partially or highly purified preparations from cells expressing TPH1. In other embodiments, the source of TPH1 is a whole cell expressing TPH1, preferably human. In some embodiments, the whole cell has been transfected with a expression vector comprising TPH1 so that the cell expresses recombinant TPH1, preferably human.

The mRNA and amino acid sequence of human TPH1 can be found in GenBank, at accession no. X52836. The genomic sequence can be found at AF057280. These nucleotide sequences can be used in methods well-known in the art to construct suitable expression vectors for expressing TPH1 recombinantly in cells, or in vitro.

Activators of TPH2 may be identified by a method comprising:

(a) providing a source of TPH2;

(b) exposing the source of TPH2 to L-tryptophan in the absence of a candidate compound;

(c) measuring the amount of 5-hydroxytryptophan produced by the source of TPH2 in the absence of the candidate compound;

(d) exposing the source of TPH2 to L-tryptophan in the presence of the candidate compound;

(e) measuring the amount of 5-hydroxytryptophan produced by the source of TPH2 in the presence of the candidate compound;

(f) where, if the amount of 5-hydroxytryptophan produced by the source of TPH2 in the presence of the candidate compound is greater than the amount of 5-hydroxytryptophan produced by the source of TPH2 in the absence of the candidate compound, the candidate compound is a TPH2 activator.

"Greater than" for the purpose of the herein-described methods of identifying therapeutic agents from a collection of candidate compounds refers to an amount that would not be attributed by those of skill in the art to normal variation seen in the method. Preferably, "greater than" is at least about 50%, at least about 75%, at least about 100%, at least about 250%, or at least about 500% more than the amount observed in the absence of the candidate compound.

In certain embodiments, the method described above includes the further step of administering the TPH2 activator identified in step (f) to a patient I need of therapy for a low bone mass disease.

In certain embodiments, the source of TPH2 is an isolated TPH2 enzyme, preferably human. Isolated TPH2 can be produced by in vitro expression of TPH1, e.g., in a coupled in vitro transcription/translation system. Alternatively, the source of TPH2 may be partially or highly purified preparations from cells expressing TPH2. In other embodiments, the source of TPH2 is a whole cell expressing TPH2, preferably human. In some embodiments, the whole cell has been transfected with a expression vector comprising TPH2 so that the cell expresses recombinant TPH2, preferably human.

The mRNA and amino acid sequence of human TPH2 can be found in GenBank, at accession no. AY098914. The genomic sequence can be found at AC090109. These nucleotide sequences can be used in methods well-known in the art to construct suitable expression vectors for expressing TPH2 recombinantly in cells, or in vitro.

Antagonists of a serotonin receptor may be identified by a method comprising:

(a) providing a cell expressing the serotonin receptor;

(b) exposing the cell expressing the serotonin receptor to serotonin or a serotonin analogue in the absence of a candidate compound;

(c) measuring the activation of the serotonin receptor in the absence of the candidate compound;

(d) exposing the cell expressing the serotonin receptor to serotonin or a serotonin analogue in the presence of a candidate compound;

(e) measuring the activation of the serotonin receptor in the presence of the candidate compound;

(f) where, if the amount of activation of the serotonin receptor in the presence of the candidate compound is less than the amount of activation of the serotonin receptor in the absence of the candidate compound, the candidate compound is a serotonin receptor antagonist.

Antagonists of a serotonin receptor may also be identified by a method comprising:

(a) providing a cell expressing the serotonin receptor;

(b) exposing the cell expressing the serotonin receptor to serotonin or a serotonin analogue in the absence of a candidate compound;

(c) measuring the binding of the serotonin or the serotonin analogue to the serotonin receptor in the absence of the candidate compound;

(d) exposing the cell expressing the serotonin receptor to serotonin or a serotonin analogue in the presence of a candidate compound;

(e) measuring the binding of the serotonin or the serotonin analogue to the serotonin receptor in the presence of the candidate compound;

(f) where, if the binding of the serotonin or the serotonin analogue to the serotonin receptor in the presence of the candidate compound is less than the binding of the serotonin or the serotonin analogue to the serotonin receptor in the absence of the candidate compound, the candidate compound is a serotonin receptor antagonist.

By "serotonin analogue" is meant a substance that binds to a serotonin receptor with binding characteristics similar to those of serotonin and/or activates a serotonin receptor in a manner similar to that of serotonin.

In certain embodiments, the present invention provides a method of lowering serum serotonin levels in a patient known or suspected to be in need of lowering of serum serotonin levels comprising:

(a) providing a plurality of candidate compounds;

(b) determining that one of the plurality of candidate compounds is an inhibitor of TPH1;

(c) administering to the patient known or suspected to be in need of lowering of serum serotonin levels a therapeutically effective amount of the candidate compound determined to be a TPH1 inhibitor in step (b).

In certain embodiments, the present invention provides a method of lowering serum serotonin levels in a patient known or suspected to be in need of lowering of serum serotonin levels comprising:

(a) providing a plurality of candidate compounds;

(b) determining that one of the plurality of candidate compounds is a serotonin receptor antagonist;

(c) administering to the patient known or suspected to be in need of lowering of serum serotonin levels a therapeutically effective amount of the candidate compound determined to be a serotonin receptor antagonist in step (b).

In the present specification, the invention has been described with reference to specific embodiments thereof. It will, however, be evident that various modifications and changes may be made thereto without departing from the broader spirit and scope of the invention. The specification and drawings are, accordingly, to be regarded in an illustrative rather than a restrictive sense.

EXAMPLES

Example 1

Assessment of Effect of Catechol-3,6-bis methyleneiminodiacetic acid (CBMIDA) on Peripheral Serotonin Production in Mice Animals One month old C57Bl/6 inbred male mice, weighing 15-16 g were used in the experiments. Animals were housed under 12 h light/12 h dark conditions in a room with controlled temperature (22° C.) and humidity (60%). Mice had ad libitum access to food and water, and were used after a minimum of 4 days of acclimatization to the housing conditions. All experiments were conducted following Columbia University Guidelines for the Animal Use and Care of laboratory mice.

Experimental Protocol

Before the experiments, animals were separated into individual cages one day prior to the experiment. Compounds were fed orally (gavage) to the mouse, calculated according to the weight of the mouse, twice a day at 1700 h and at 1100 h. Oral feeding was selected over intravenous or intraperitoneal infusion of the compound for better inhibition of Tryptophan hydroxylase-1 (TPH1) present in the gut vs TPH2 that synthesizes serotonin and is present in the brain. This route created two potential barriers for the compound to reach the brain. First, the intestinal blood barrier that has poor permeability to the EDTA-based compounds (as is the case with CBMIDA), hence does not allow all the amount given orally to be absorbed in the circulation (only 5-10% is transported to blood). The second barrier is the blood-brain barrier that shows poor permeability to a large number of compounds including EDTA compounds. Control animals received the same volume of vehicle. Blood was collected through heart puncture on isofluorane-anaesthesized animals and allowed to clot for 5 minutes on ice. The serum was separated, snap chilled in liquid nitrogen and frozen at −80° C. till analyzed. Brainstems from all the animals were collected and processed for brain serotonin measurement through HPLC. Mice were observed for any physical or behavioral abnormality during the course of investigation.

Serotonin Measurements in Serum

The Serotonin ELISA kit obtained from the Fitzgerald company was used to measure derivatized serotonin from serum. Derivatization is part of the sample preparation. Serotonin present in the serum was first quantitatively acylated into N-Acylserotonin using the acylation reagent. The principle of the assay is based on competitive ELISA, wherein serotonin that is bound to the solid phase of the plate and the N-acylserotonin compete for the fixed number of antiserum binding sites. When the reaction is in equilibrium, free antigen and free antigen-antiserum complexes are removed by washing.

The antibody bound to the solid phase serotonin is then detected using antirabbit/peroxidase. The substrate TMB/Peroxidase reaction is read at 450 nm. The amount of antibody bound to the solid phase serotonin is inversely proportional to the concentration of serotonin in the sample.

Drugs Used in the Study

Catechol-3,6-bis methyleneiminodiacetic acid (CBMIDA) (basic structure is an EDTA-like compound and the catechol ring is at the centre) synthesized at the Columbia University Chemistry division, and para-chlorophenylalanine (pCPA) obtained from Sigma Aldrich Corp. were used. Each compound was dissolved with twice molar solution of $NaHCO_3$ in water and given to mouse orally at 250 and 500 mg/kg/dose.

Results

Figure 11:
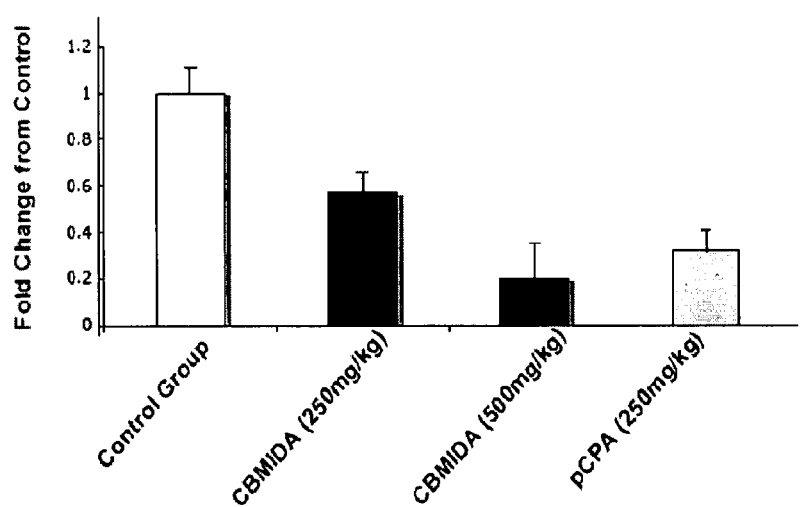
FIG. 11. Oral feeding of CBMIDA reduces peripheral serotonin.

As can be seen in FIG. 11, oral administration of CBMIDA decreased serotonin serum levels to 80% below normal at a dose of 500 mg/kg twice daily. Lowering this dose to 250 mg/kg produced the effect but to a lesser extent. In fact when one compares the two doses versus control animals, a dose response curve is produced. While pCPA, a well known inhibitor of tryptophan hydroxylase used as a control, decreased the serum serotonin levels as expected to >60% below normal range.

Example 2

Synthesis of catechol TPH1 Inhibitors

Synthesis of 2,2',2'',2'''-(2,3-dihydroxy-1,4-phenylene)bis(methylene) bis(azanetriyl)tetraacetic acid

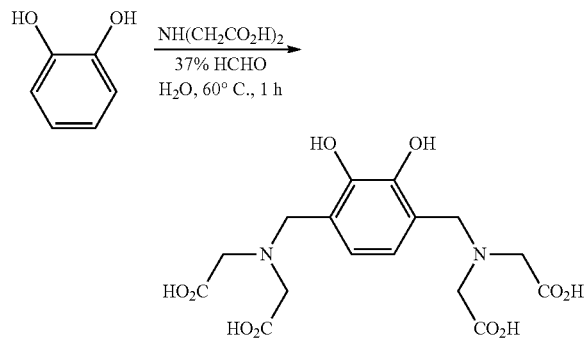

Catechol (5.5 g, 0.05 mol) and iminodiacetic acid (11.3 g, 0.1 mol) were suspended in a mixture of acetic acid (20 ml) and water (40 ml). Formaldehyde (37%, 10 ml) was added slowly. The reaction was stirred at 60° C. for 1 hour. The solution was cooled and white precipitate was filtered, washed with water and ethanol, dried. 15.0 g of product was obtained (yield: 75%).

Synthesis of 2,2'-(2,3-dihydroxy-1,4-phenylene)bis(methylene)bis((2-amino-2-oxoethyl)azanediyl)diacetic acid

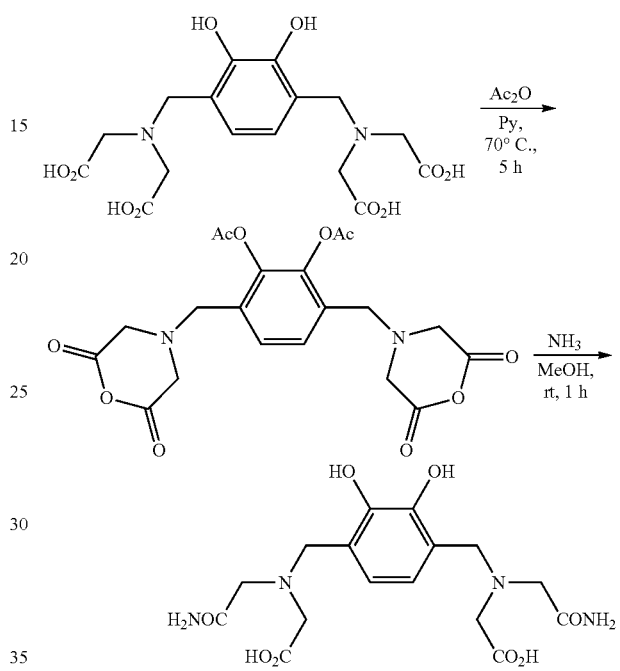

2,2',2'',2'''-(2,3-dihydroxy-1,4-phenylene)bis(methylene)bis(azanetriyl)tetraacetic acid (5 g, 12.5 mmol) was added to acetyl anhydride (10 ml) followed by pyridine (3 ml). The reaction was heated at 70° C. for 5 h. The excess anhydride and pyridine were removed under reduced pressure and the residue was recrystallized in acetyl anhydride. 2.8 g of 3,6-bis((2,6-dioxomorpholino)methyl)-1,2-phenylene diacetate was obtained as white solid (yield: 51%).

3,6-bis((2,6-dioxomorpholino)methyl)-1,2-phenylene diacetate (2.24 g, 10 mmol) was added to the solution of ammonia in methanol (7N, 20 ml). The reaction was stirred at room temperature for 1 hour. After removing methanol, the residue was recrystallized in methanol and acetone. 3.5 g of product was obtained as white solid (yield: 88%).

Synthesis of 2,2'-((11,12-dihydroxy-6-methyl-4,5,6,8-tetrahydropyrido[3,2,1-de]phenanthridin-10-yl)methylazanediyl)diacetic acid

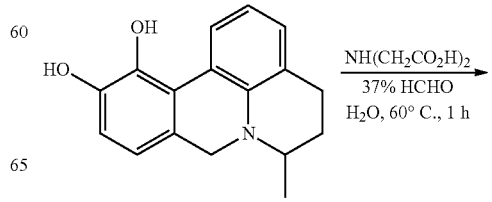

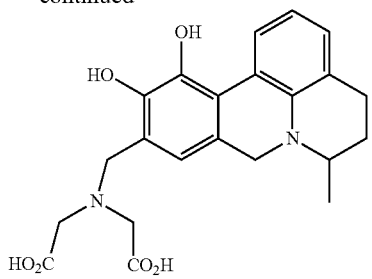

Catechol (5.5 g, 0.05 mol) and iminodiacetic acid (11.3 g, 0.1 mol) were suspended in the mixture of acetic acid (20 ml) and water (40 ml). Formaldehyde (37%, 10 ml) was added slowly. The reaction was stirred at 60° C. for 1 hour. The solution was cooled and the white precipitate was filtered, washed with water and ethanol, and dried. 15.0 g of product was obtained (yield: 75%).

6-methyl-4,5,6,8-tetrahydropyrido[3,2,1-de]phenanthridine-11,12-diol (1.33 g, 5 mmol) and iminodiacetic acid (1.13 g, 10 mmol) were suspended in a mixture of acetic acid (2 ml) and water (4 ml). Formaldehyde (37%, 1 ml) was added slowly. The reaction was stirred at 60° C. for 3 hours. The solvent was removed under reduced pressure and the residue was recrystallized in methanol and water. 1.8 g of product was obtained as a white solid (yield: 87%).

Example 3

Measurement of Serum Serotonin

Two possible methods of measuring serum serotonin levels are as follows:

(1) Initial steps are performed at room temperature using polypropylene tubes and pipettes. Establishing free flow by venipuncture, blood is collected from an antecubital vein with a 19-gauge, thin-walled butterfly needle into EDTA-containing vacuum tubes. The tubes are centrifuged (Sorvall GLC-2B) at 800 rpm (100×g) for 15 minutes at room temperature. The upper layer of platelet-rich plasma (PRP), about 0.3 cm from the interface layer (buffy coat), is removed with a plastic pipette and transferred to a new polypropylene test tube. The tube containing the platelet-poor plasma (PRP) is iced for 10 min before being centrifuged at 11,000 rpm (14,500×g) in a Sorvall SS-34 rotor for 6 min at 4° C. to yield the platelet pellet and platelet poor plasma (PPP). The supernate containing PPP is removed and placed into a new polypropylene test tube in a volume of 500 microliters in Eppendorf tubes. The platelet-rich pellets are resuspended in 1 ml saline. Mixing or vortexing, before transfer to an Eppendorf tube, is sometimes required to maintain a homogenous suspension without clumps. The aliquoted plasma supernate (PPP) and the resuspended pellet (PRP) are kept at −20. For the serotonin assay, the samples are resuspended in saline. The 'hormonal' element of serotonin that is of most interest is the circulating level in PPP but the PRP fraction will also be measured. The method is an ELISA obtained from Fitzgerald Industries International (Concord, Mass.). It measures the derivatized serotonin from serum or plasma samples or urine samples. Derivatization is part of the sample preparation. Serotonin present in the biological fluids (e.g., serum) is first quantitatively acylated using the acylation reagent into N-acylserotonin. The assay is based on the competitive ELISA principle wherein serotonin that is bound to the solid phase of the plate and the N-acylserotonin competes for the fixed number of antiserum binding sites. When the reaction is in equilibrium, free antigen and free antigen-antiserum complexes are removed by washing. The antibody bound to the solid phase serotonin is then detected by the anti-rabbit/peroxidase. The substrate TMB/Peroxidase reaction is read at 450 nm. The amount of antibody bound to the solid phase serotonin is inversely proportional to the concentration of serotonin in the sample. Although the ELISA assay is useful, we will have the opportunity to apply an even more precise assay namely HPLC coupled with electrochemical detection.

(2) Another method relies on HPLC coupled with electrochemical detection. Samples obtained in the manner described above are precipitated with 1N $HClO_4$ (1:1), diluted and aliquoted into HPLC vials containing 32.5 μl of 0.02 M acetic acid. The fractions are injected via a Gilson 223 XL autoinjector onto the column. 20 μl of the microdialysis sample are injected onto a 100×2 mm C18 Hypersil 3 μm column and separated with a mobile phase consisting of 4.1 g/l sodium acetate, 500 mg/l Na2-EDTA, 50 mg/l heptane sulfonic acid, 4.5% methanol v/v, and 30 μl/l of triethylamine, pH 4.75 at a flow rate of 0.4 ml/min using a Shimadzu LC-10 AD pump. Serotonin is detected amperometrically at a glassy carbon electrode at 500 mV vs Ag/AgCl. The detection limit, 0.5 fmol serotonin per 20 μl sample or 10 pM, is well within the circulating concentrations of serotonin. Since serotonin measured in PPP is not bound to any appreciable degree by plasma proteins, these measurements can be regarded as equivalent to free serotonin levels.

Example 4

Synthesis Schemes for Additional TPH1 Inhibitors

TPH1 inhibitors having the following structures:

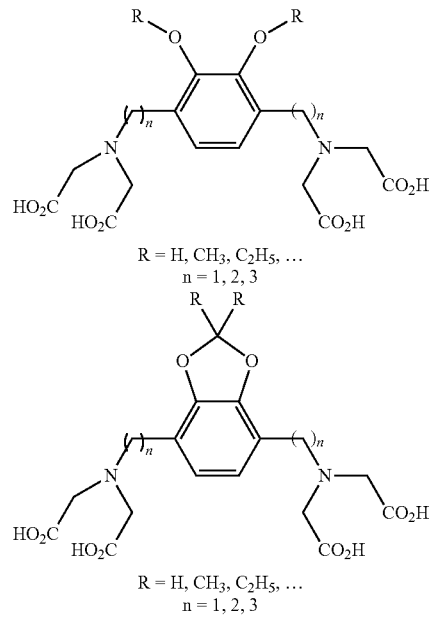

$R = H, CH_3, C_2H_5, \ldots$
$n = 1, 2, 3$ $R = H, CH_3, C_2H_5, \ldots$
$n = 1, 2, 3$ can be synthesized by the following methods:
for n = 1,
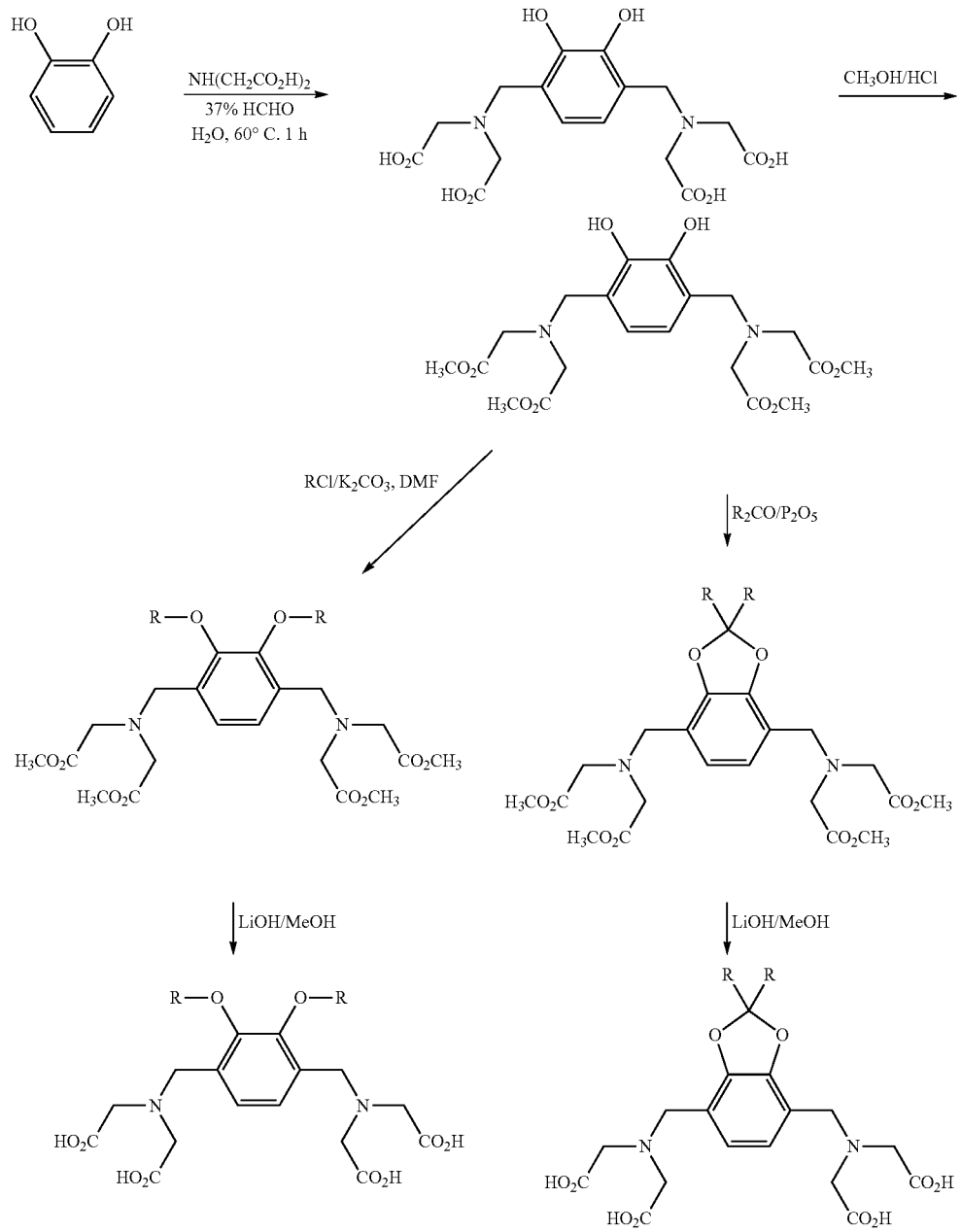
for n = 2,
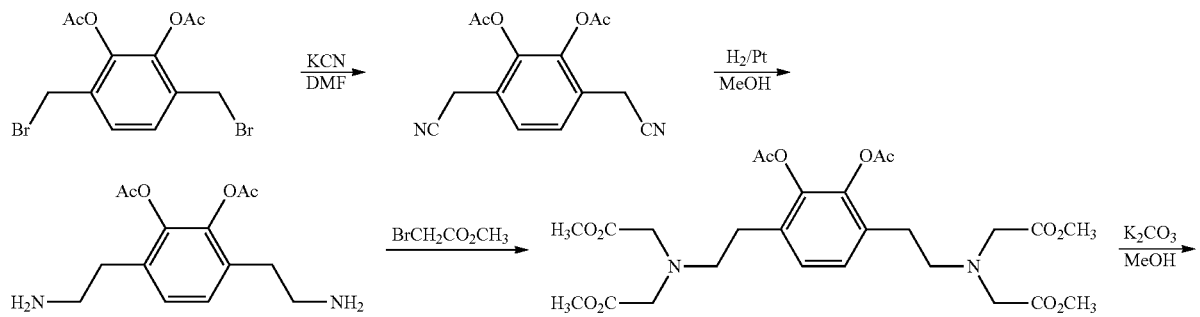

-continued
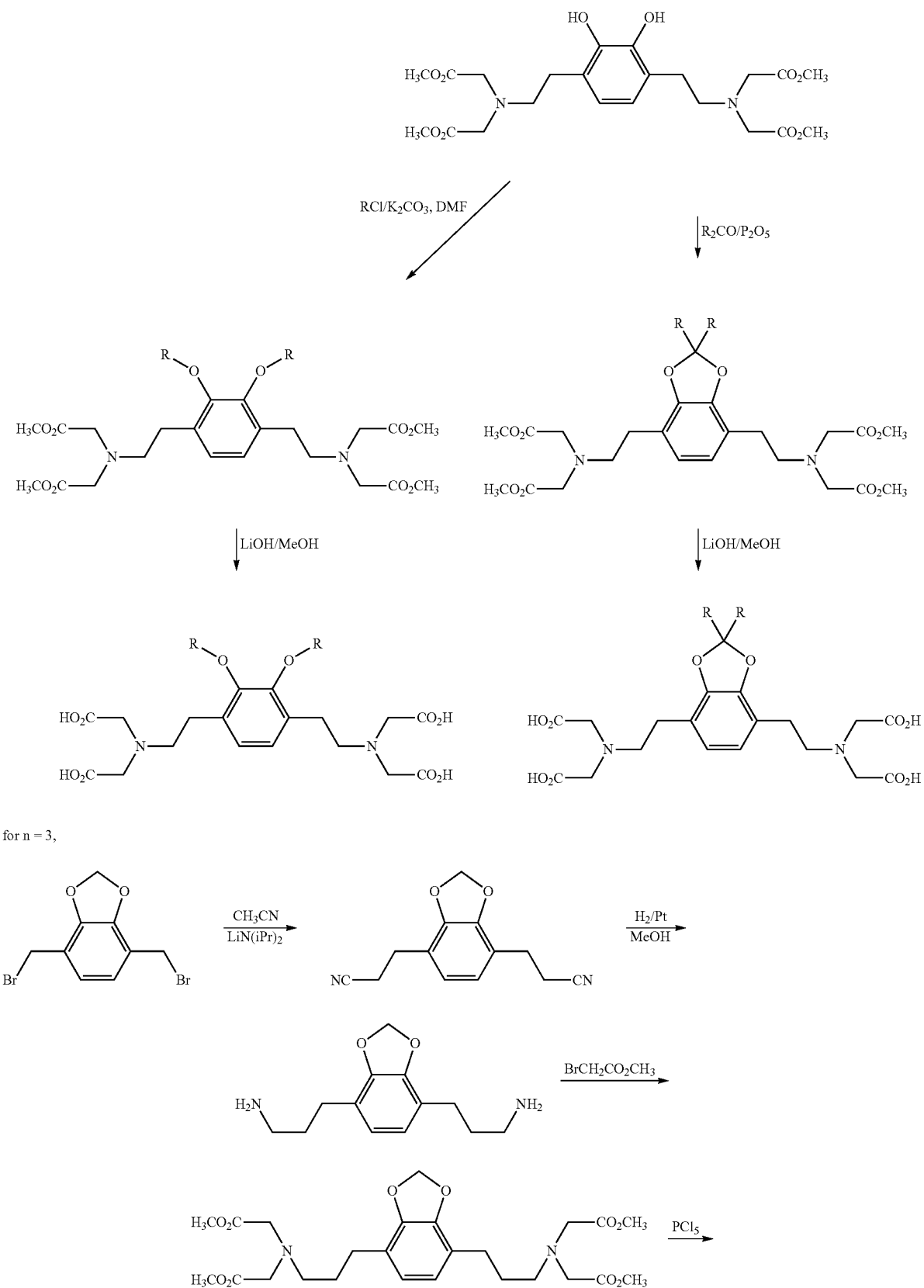

-continued
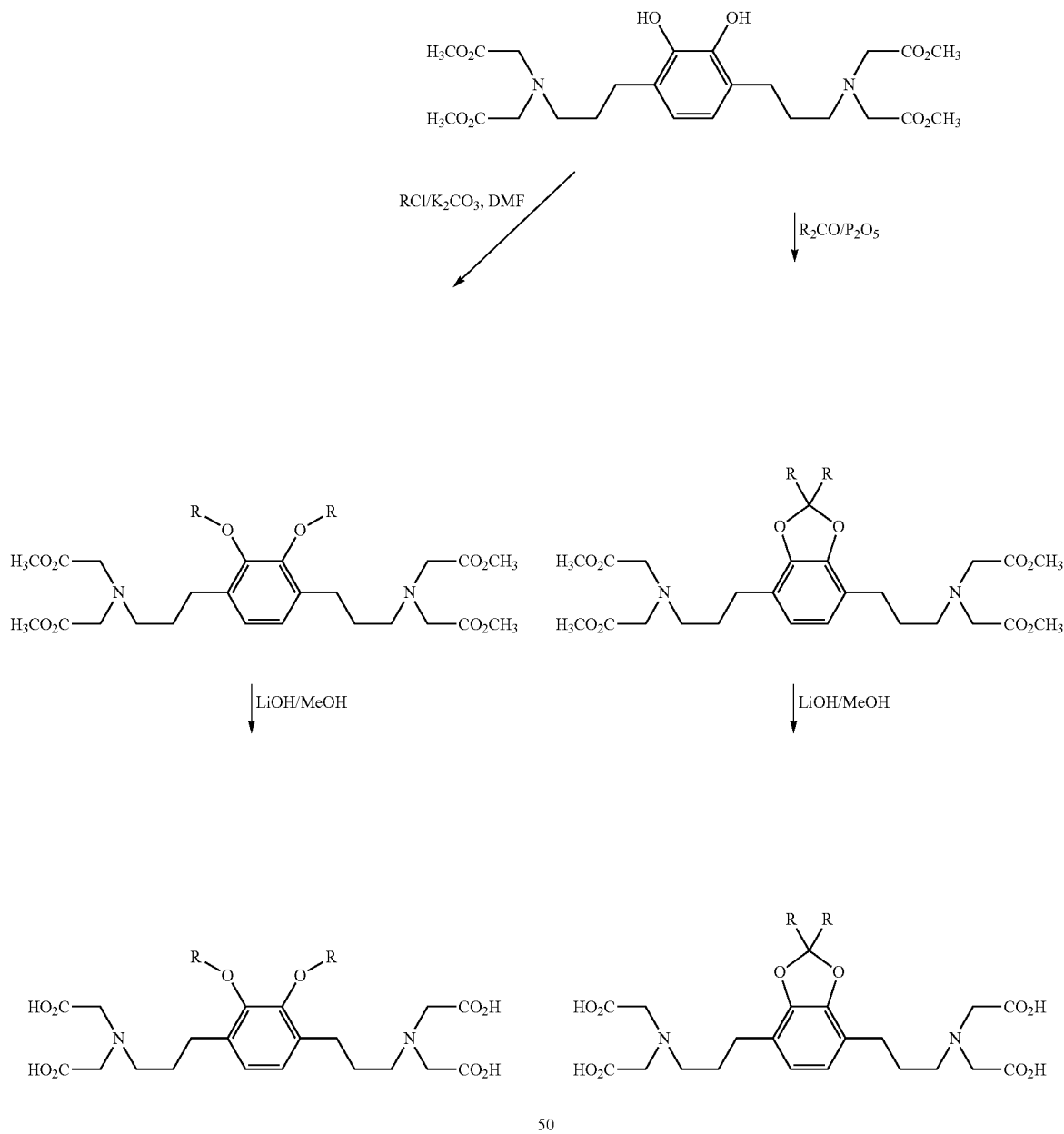
TPH1 inhibitors having the following structures:
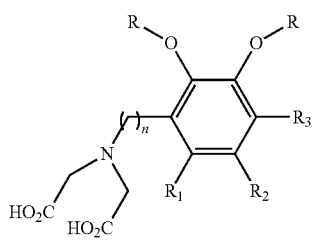
R = H, CH₃, C₂H₅, ...
n = 1, 2, 3
R₁, R₂, R₃ = H, F, Cl, CH₃, C₂H₅, CH₃O, NH₂, ...
-continued
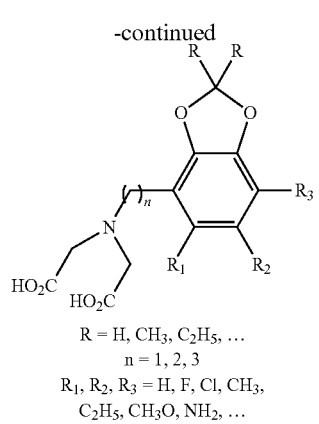
R = H, CH₃, C₂H₅, ...
n = 1, 2, 3
R₁, R₂, R₃ = H, F, Cl, CH₃, C₂H₅, CH₃O, NH₂, ...

can be synthesized by the following methods:
for n = 1,
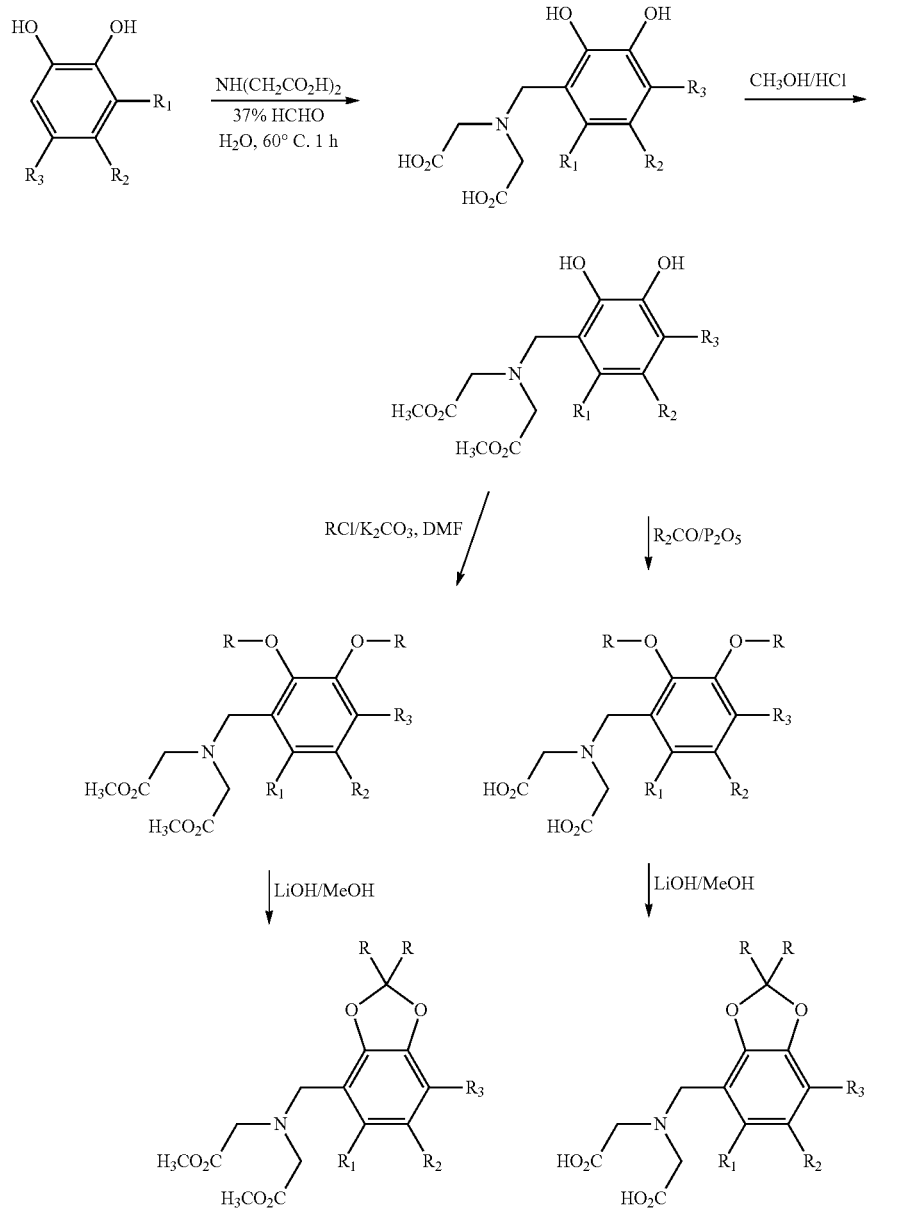
for n = 2,
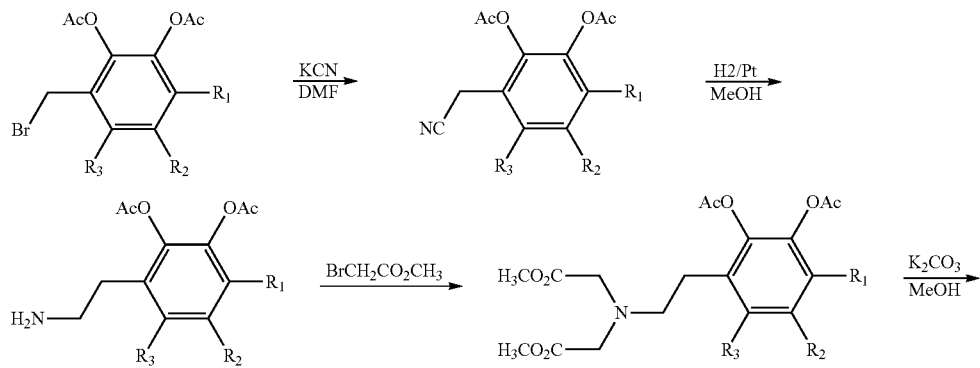

-continued
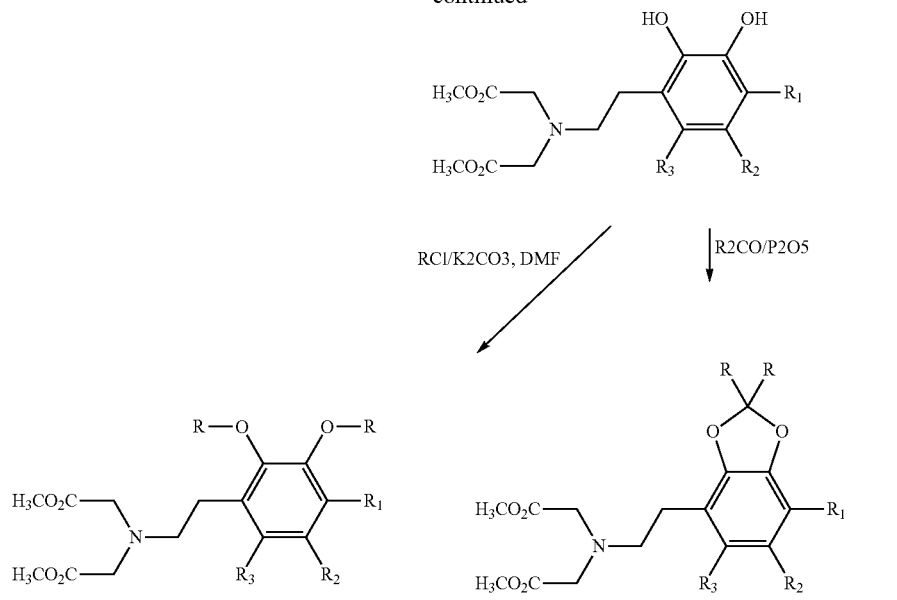
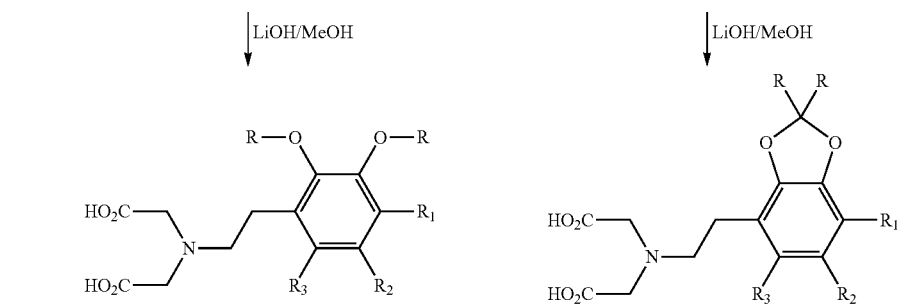
for n = 3,
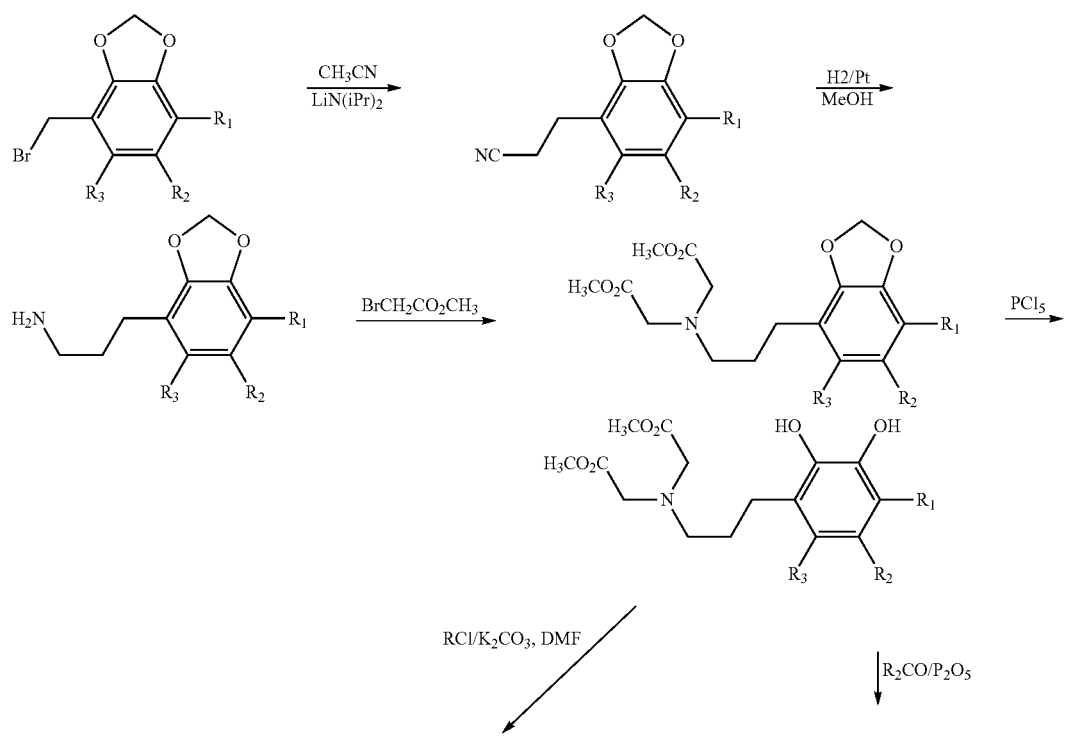

-continued

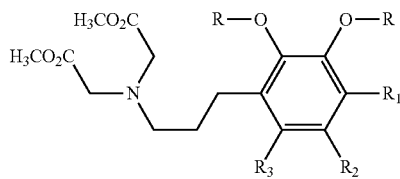

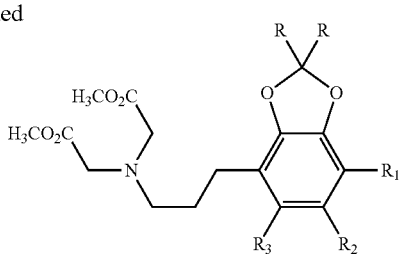

↓ LiOH/MeOH

↓ LiOH/MeOH

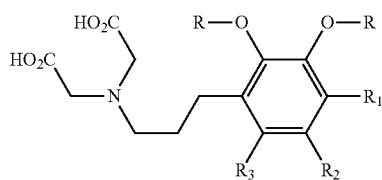

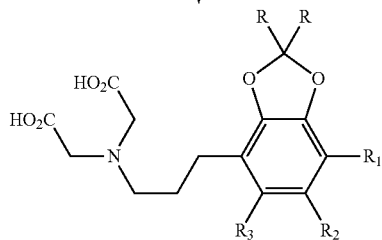

Example 5

Generation of Mutant Animals and Animal Treatments

Generation of Lrp5−/− (Kato et al., 2002, J. Cell Biol. 157:303-314) β-cateninfloxed/floxed (Glass et al., 2005, Dev. Cell 8:751-764), α1(I)collagen-cre transgenic (Dacquin et al., 2002, Dev. Dyn. 224:245-251) and Htt−/− (Ansorge et al., 2008, J. Neurosci. 28:199-207) mice were as described previously. Lrp5+/−;Htt+/− double heterozygous mice were generated by crossing Lrp5+/− and Htt+/− mice. Three week-old Wt or Lrp5−/− mice were administered pCPA on alternate days for 9 weeks by i.p. All animal protocols were approved by the Animal Care Committees of Columbia University.

Example 6

Morphometric Measurements

Static histomorphometry measurements were performed as previously described in accordance with standard nomenclature, using the Osteomeasure Analysis System (Osteometrics, Inc) (Ducy et al., 2000, Cell 100:197-207). Four to 9 animals were assigned per group.

Example 7

Cell Cultures

Calvaria osteoblasts were extracted by triple collagenase/ trypsine digestion from 4 day-old CD1 pups and differentiated with ascorbic acid as previously described (Ducy et al., 2000, Cell 100:197-207).

Example 8

Gene Expression Studies

Osteoblasts were treated in serum-free medium with vehicle or Serotonin (50 to 100 μM, Sigma) for 24 hr. Total RNA were extracted with Trizol (Invitrogen). cDNA were generated using the ABI Reverse transcriptase system and random hexanucleotide primers. Real-time PCR was performed using superarray primers on a Stratagene real time PCR cycler and Actin expression was used as endogenous control. Chromatin immunoprecipitation assays (ChIP) were performed by standard procedures using primary osteoblasts. Microarray analysis was performed as described previously (Glass et al., 2005, Dev. Cell 8:751-764).

Example 9

Biochemical Studies

Osteoblasts were treated in serum-free medium with vehicle or Serotonin (50 to 100 μM, Sigma) for 24 hr. Lysates from primary osteoblasts or crushed frozen bones were prepared in RIPA buffer in the presence of protease and phosphatase inhibitors. Twenty to 60 μg of proteins were separated by SDS-PAGE in reducing conditions and transferred on nitrocellulose membrane using standard protocols. Membranes were incubated with primary antibodies including total or anti-Phospho CREB (Cell Signaling Technology).

Example 10

Hormone Measurements

Serotonin serum levels were quantified using immunoassay kits from Fitzgerald (Serotonin) and serotonin levels in the different regions of the brain were quantified by HPLC method as described previously (Mann et al., 1992, Arch. Gen. Psychiatry 49:442-446).

Example 11

Changes in Serotonin Levels Upon Oral Deeding of CBMIDA and Other Compounds

Serotonin serum levels relative to vehicle were measured following the oral feeding to 4 week old mice of the following compounds:

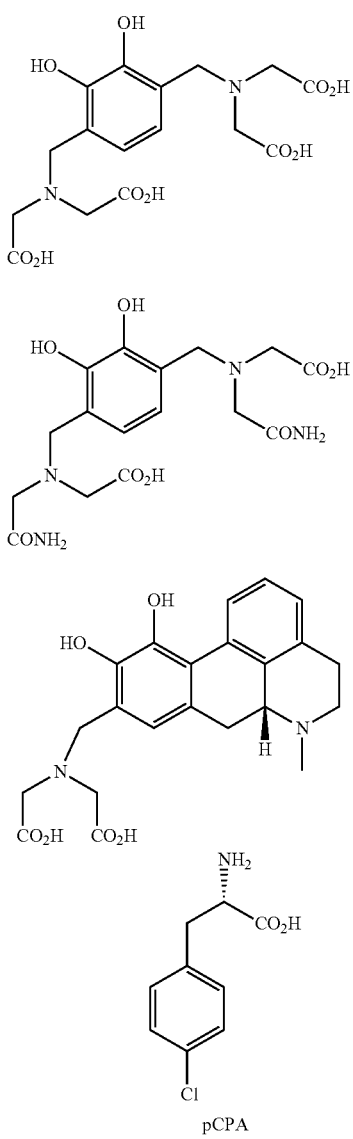

Compound 1

Compound 2

Compound 3 pCPA

Figure 13:
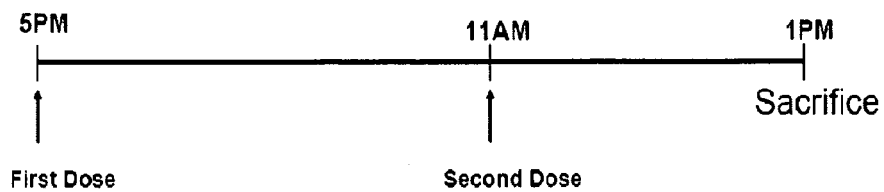
FIG. 13. Regimen for the oral feeding of CBMIDA and other compounds in Example 11.
Figure 14:
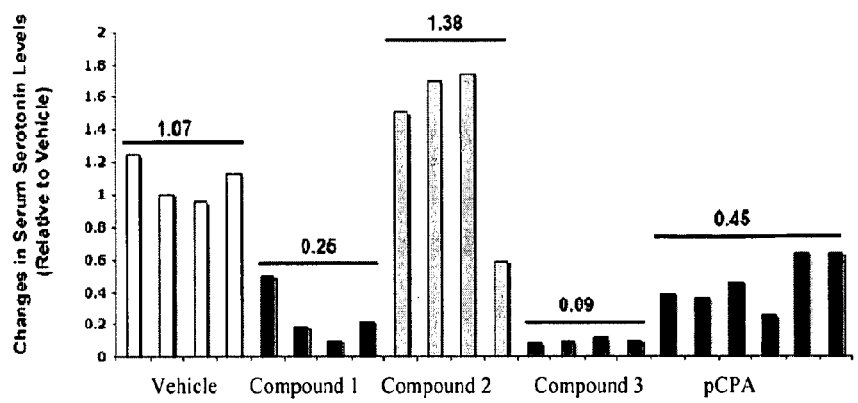
FIG. 14. Changes in serotonin levels upon oral deeding of CBMIDA and other compounds in Example 11.

The feeding protocol is shown in FIG. 13. Results are shown in FIG. 14. Experimental details were similar to those of Example 12, below.

Example 12

Assessment of Effect of Novel Inhibitors of Tryptophan Hydroxylase in Protection from Ovariectomy-Induced Bone Loss Animals 6-week old C57Bl/6 inbred female mice, weighing 12-14 g, were used in the experiments. Animals were housed under 12 h light/12 h dark conditions in a room with controlled temperature (22° C.) and humidity (60%). Mice had ad libitum access to food and water, and were used after a minimum of 4 days of acclimatization to the housing conditions. All experiments were conducted following Columbia University Guidelines for the Animal Use and Care of laboratory mice.

Experimental Protocol

Animals were separated into different groups one day prior to the experiments. Mice were ovariectomized (OVX) under anaesthesia (Avertin). Compounds were fed orally (Gavage) twice a day at 1700 h and at 1100 h for the pilot study while for the long term study compounds were given at 1700 h once a day. Oral feeding was selected over intravenous or intraperitoneal infusion of the compound for better inhibition of Tryptophan hydroxylase-1 (Tph1) present in the gut and to avoid affecting Tph2 function in the brain. This route creates two potential barriers for the compound to reach the brain. First, the intestinal blood barrier that has poor permeability to the EDTA-based compounds (as is the case with Compound 1), hence does not allow all the amount given orally to be absorbed (only 5-10% is transported to blood) in the general circulation; second, the blood-brain barrier itself shows poor permeability to a large number of compounds including EDTA compounds. Control animals received the same volume of vehicle. Blood was collected through heart puncture on isofluorane-anaesthesized animals, allowed to clot for 5 minutes on ice and then serum was separated, snap chilled in liquid nitrogen and frozen at −80° C. till analyzed. Mice were observed daily for any physical or behavioral abnormality during the course of investigation.

Experiment I: Pilot Study to Determine Efficacy of the Compounds to be Tested
Group 1: Vehicle
Group 2: Compound 1
Group 3: Compound 2
Group 4: Compound 3
Group 5: Compound 4 (LP-533401)

Experiment II: Effect of Compounds 1 and 4 on Protection from OVX-Induced Bone Loss
Protocol 1: Gavage Feeding of the Compounds Will be Started 1 Day after OVX for 6 Weeks
Group 1: Sham treatment
Group 2: OVX
Group 3: OVX+Compound 1 (250 mg/kg)
Group 4: OVX+Compound 1 (500 mg/kg)
Group 5: OVX+Compound 4 (250 mg/kg)

Protocol 2: Gavage Feeding of the Compounds Will be Started 2 Weeks after OVX for 6 Weeks
Group 1: Sham treatment
Group 2: OVX
Group 3: OVX+Compound 1 (250 mg/kg)
Group 4: OVX+Compound 1 (500 mg/kg)
Group 5: OVX+Compound 4 (250 mg/kg)

Protocol 3: Gavage Feeding of the Compounds Will be Started 4 Weeks after OVX for 6 Weeks
Group 1: Sham treatment
Group 2: OVX
Group 3: OVX+Compound 1 (250 mg/kg)
Group 4: OVX+Compound 1 (500 mg/kg)
Group 2: OVX+Compound 4 (250 mg/kg)

Serotonin Measurement in Serum

The Serotonin ELISA kit obtained from the Fitzgerald company was used to measure derivatized serotonin from serum. Derivatization is part of the sample preparation. Serotonin present in the serum was first quantitatively acylated using the acylation reagent into N-Acylserotonin. The principle of the assay is based on competitive ELISA, wherein serotonin that is bound to the solid phase of the plate and the N-acylserotonin compete for the fixed number of antiserum binding sites. When the reaction is in equilibrium, free antigen and free antigen-antiserum complexes are removed by washing. The antibody bound to the solid phase serotonin is then detected by anti-rabbit/peroxidase. The substrate TMB/Peroxidase reaction is read at 450 nm. The amount of antibody bound to the solid phase serotonin is inversely proportional to the concentration of serotonin in the sample.

Drugs Used in the Study

We used Catechol-3,6-bis methyleneiminodiacetic acid [(CBMIDA) Compound 1: basic structure is a EDTA-like compound and the catechol ring is at the center)] synthesized at the Columbia University Chemistry division and para-Chlorophenylalanine (pCPA) obtained from Sigma Aldrich Corp. for our experiments. Compounds were dissolved with twice molar solution of $NaHCO_3$ in water and given to mice orally at 250 and 500 mg/kg/dose. Compounds 2 and 3 were dissolved in water.

Results

Figure 15:
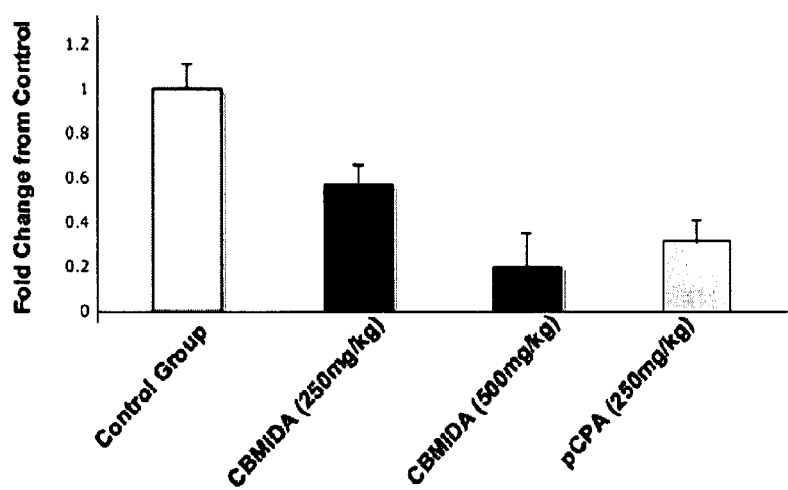
FIG. 15. Effect of CBMIDA and pCPA on peripheral serotonin production in ovariectomized mice.

We tested the effect of the four compounds mentioned above for their effect on peripheral serotonin production in mice. As seen in FIG. 15, oral administration of Compound 1 (CBMIDA) decreased serotonin serum levels to 80% below normal at a dose of 500 mg/kg twice daily. Lowering this dose to 250 mg/kg produced the effect but to a lesser extent while Compound 2 had minimal effect. Although Compound 3 decreased the serotonin levels dramatically, it was toxic to the animals, as they looked very lethargic and sick.

We also tested the effect of different doses of Compound 1 on serotonin levels. As can be seen in FIG. 15, Compound 1 produced a dose response curve when compared to the control animals. While pCPA, a well known inhibitor of Tryptophan hydroxylase used as a control, decreased serotonin levels as expected to 60% below normal range.

LITERATURE CITED

1. Gong, Y., et al. *LDL Receptor-Related Protein 5 (LRP5) Affects Bone Accrual and Eye Development*. Cell, 2001. 107(4): p. 513-23.
2. Kato, M., M. S. Patel, R. Levasseur, I. Lobov, B. H. Chang, D. A. Glass, 2nd, C. Hartmann, L. Li, T. H. Hwang, C. F. Brayton, R. A. Lang, G. Karsenty, and L. Chan, *Cbfa1-independent decrease in osteoblast proliferation, osteopenia, and persistent embryonic eye vascularization in mice deficient in Lrp5, a Wnt coreceptor*. J Cell Biol, 2002. 157(2): p. 303-14.
3. Logan, C. Y. and R. Nusse, *The Wnt signaling pathway in development and disease*. Annu Rev Cell Dev Biol, 2004. 20: p. 781-810.
4. Boyden, L. M., J. Mao, J. Belsky, L. Mitzner, A. Farhi, M. A. Mitnick, D. Wu, K. Insogna, and R. P. Litton, *High bone density due to a mutation in LDL-receptor-related protein 5*. N Engl J Med, 2002. 346(20): p. 1513-21.
5. Glass, D. A., 2nd, et al., *Canonical Wnt signaling in differentiated osteoblasts controls osteoclast differentiation*. Dev Cell, 2005. 8(5): p. 751-764.
6. Holmen, S. L., C. R. Zylstra, A. Mukherjee, R. E. Sigler, M. C. Faugere, M. L. Bouxsein, L. Deng, T. L. Clemens, and B. O. Williams, *Essential role of beta-catenin in postnatal bone acquisition*. J Biol Chem, 2005. 280(22): p. 21162-8.
7. Gershon, M. D. and J. Tack, *The serotonin signaling system: from basic understanding to drug development for functional GI disorders*. Gastroenterology, 2007. 132(1): p. 397-414.
8. Diem, S. J., T. L. Blackwell, K. L. Stone, K. Yaffe, E. M. Haney, M. M. Bliziotes, and K. E. Ensrud, *Use of antidepressants and rates of hip bone loss in older women: the study of osteoporotic fractures*. Arch Intern Med, 2007. 167(12): p. 1240-5.
9. Haney, E. M., B. K. Chan, S. J. Diem, K. E. Ensrud, J. A. Cauley, E. Barrett-Connor, E. Orwoll, and M. M. Bliziotes, *Association of low bone mineral density with selective serotonin reuptake inhibitor use by older men*. Arch Intern Med, 2007. 167(12): p. 1246-51.
10. Schneeweiss, S, and P. S. Wang, *Association between SSRI use and hip fractures and the effect of residual confounding bias in claims database studies*. J Clin Psychopharmacol, 2004. 24(6): p. 632-8.
11. Richards, J. B., A. Papaioannou, J. D. Adachi, L. Joseph, H. E. Whitson, J. C. Prior, and D. Goltzman, *Effect of selective serotonin reuptake inhibitors on the risk of fracture*. Arch Intern Med, 2007. 167(2): p. 188-94.
12. Zhang, Y., R. Proenca, M. Maffei, M. Barone, L. Leopold, and J. M. Friedman, *Positional cloning of the mouse obese gene and its human homologue*. Nature, 1994. 372: p. 425-432.
13. Ducy, P., M. Amling, S. Takeda, M. Priemel, A. F. Schilling, F. T. Beil, J. Shen, C. Vinson, J. M. Rueger, and G. Karsenty, *Leptin inhibits bone formation through a hypothalamic relay: a central control of bone mass*. Cell, 2000. 100(2): p. 197-207.
14. Elefteriou, F., J. D. Ahn, S. Takeda, M. Starbuck, X. Yang, X. Liu, H. Kondo, W. G. Richards, T. W. Bannon, M. Noda, K. Clement, C. Vaisse, and G. Karsenty, *Leptin regulation of bone resorption by the sympathetic nervous system and CART*. Nature, 2005. 434(7032): p. 514-20.
15. Kuro-o, M., Y. Matsumura, H. Aizawa, H. Kawaguchi, T. Suga, T. Utsugi, Y. Ohyama, M. Kurabayashi, T. Kaname, E. Kume, H. Iwasaki, A. Iida, T. Shiraki-Iida, S, Nishikawa, R. Nagai, and Y. I. Nabeshima, *Mutation of the mouse klotho gene leads to a syndrome resembling ageing*. Nature, 1997. 390(6655): p. 45-51.
16. Donehower, L. A., M. Harvey, B. L. Slagle, M. J. McArthur, C. A. Montgomery, Jr., J. S. Butel, and A. Bradley, *Mice deficient for p53 are developmentally normal but susceptible to spontaneous tumours*. Nature, 1992. 356 (6366): p. 215-21.
17. Dutnall, R. N. and L. Pillus, *Deciphering NAD-dependent deacetylases*. Cell, 2001. 105(2): p. 161-4.
18. Yoshizawa, T., Y. Handa, Y. Uematsu, S. Takeda, K. Sekine, Y. Yoshihara, T. Kawakami, K. Arioka, H. Sato, Y. Uchiyama, S. Masushige, A. Fukamizu, T. Matsumoto, and S. Kato, *Mice lacking the vitamin D receptor exhibit impaired bone formation, uterine hypoplasia and growth retardation after weaning*. Nat Genet, 1997. 16(4): p. 391-6.
19. Ohshima, S., Y. Saeki, T. Mima, M. Sasai, K. Nishioka, S. Nomura, M. Kopf, Y. Katada, T. Tanaka, M. Suemura, and T. Kishimoto, *Interleukin 6 plays a key role in the development of antigen-induced arthritis*. Proc Natl Acad Sci U serotonin A, 1998. 95(14): p. 8222-6.
20. Windahl, S. H., G. Andersson, and J. A. Gustafsson, *Elucidation of estrogen receptor function in bone with the use of mouse models*. Trends Endocrinol Metab, 2002. 13(5): p. 195-200.
21. Johnson, M. L., G. Gong, W. Kimberling, S. M. Recker, D. B. Kimmel, and R. R. Recker, *Linkage of a gene causing high bone mass to human chromosome 11(11q12-13)*. Am J Hum Genet, 1997. 60: p. 1326-1332.
22. Wehrli, M., S. T. Dougan, K. Caldwell, L. O'Keefe, S. Schwartz, and D. Vaizel-Ohayon, *Arrow encodes an LDL-receptor-related protein essential for Wingless signalling*. Nature, 2000. 407: p. 527-530.
23. Tamai, K., M. Semenov, Y. Kato, R. Spokony, C. Liu, Y. Katsuyama, F. Hess, J. P. Saint-Jeannet, and X. He, *LDL-receptor-related proteins in Wnt signal transduction*. Nature, 2000. 407: p. 530-535.
24. Mao, J., J. Y. Wang, L. Bo, W. Pan, G. H. Farr, III, C. Flynn, H. Yuan, S. Takada, D. Kimelman, L. Lin, and D. Wu, *Low-density lipoprotein receptor-related protein-5* binds to axin and regulates the canonical Wnt Signaling Pathway. Mol Cell, 2001.7: p. 801-809.
25. Day, T. F., X. Guo, L. Garrett-Beal, and Y. Yang, *Wnt/beta-catenin signaling in mesenchymal progenitors controls osteoblast and chondrocyte differentiation during vertebrate skeletogenesis.* Dev Cell, 2005.8(5): p. 739-50.
26. Hu, H., M. J. Hilton, X. Tu, K. Yu, D. M. Ornitz, and F. Long, *Sequential roles of Hedgehog and Wnt signaling in osteoblast development.* Development, 2005. 132(1): p. 49-60.
27. Kikuchi, A., H. Yamamoto, and S. Kishida, *Multiplicity of the interactions of Wnt proteins and their receptors.* Cell Signal, 2007. 19(4): p. 659-71.
28. Chien, K. R. and G. Karsenty, *Longevity and lineages: toward the integrative biology of degenerative diseases in heart, muscle, and bone.* Cell, 2005. 120(4): p. 533-44.
29. Yoshida, Y., S. Tanaka, H. Umemori, O. Minowa, M. Usui, N. Ikematsu, E. Hosoda, T. Imamura, J. Kuno, T. Yamashita, K. Miyazono, M. Noda, T. Noda, and T. Yamamoto, *Negative regulation of BMP/Smad signaling by Tob in osteoblasts.* Cell, 2000. 103(7): p. 1085-97.
30. Tsuji, K., A. Bandyopadhyay, B. D. Harfe, K. Cox, S. Kakar, L. Gerstenfeld, T. Einhorn, C. J. Tabin, and V. Rosen, *BMP2 activity, although dispensable for bone formation, is required for the initiation of fracture healing.* Nat Genet, 2006. 38(12): p. 1424-9.
31. Zhao, G., M. C. Monier-Faugere, M. C. Langub, Z. Geng, T. Nakayama, J. W. Pike, S. D. Chernausek, C. J. Rosen, L. R. Donahue, H. H. Malluche, J. A. Fagin, and T. L. Clemens, *Targeted overexpression of insulin-like growth factor I to osteoblasts of transgenic mice: increased trabecular bone volume without increased osteoblast proliferation.* Endocrinology, 2000. 141(7): p. 2674-82.
32. Takeda, S., F. Elefteriou, R. Levasseur, X. Liu, L. Zhao, K. L. Parker, D. Armstrong, P. Ducy, and G. Karsenty, *Leptin regulates bone formation via the sympathetic nervous system.* Cell, 2002. 111(3): p. 305-17.
33. Abe, E., R. C. Marians, W. Yu, X. B. Wu, T. Ando, Y. Li, J. Iqbal, L. Eldeiry, G. Rajendren, H. C. Blair, T. F. Davies, and M. Zaidi, *TSH is a negative regulator of skeletal remodeling.* Cell, 2003. 115(2): p. 151-62.
34. Gershon, M. D., P. R. Wade, Al. Kirchgessner, and H. Tamir, *5-HT receptor subtypes outside the central nervous system. Roles in the physiology of the gut.* Neuropsychopharmacology, 1990. 3(5-6): p. 385-95.
35. Walther, D. J., J. U. Peter, S. Bashammakh, H. Hortnagl, M. Voits, H. Fink, and M. Bader, *Synthesis of serotonin by a second tryptophan hydroxylase isoform.* Science, 2003. 299(5603): p. 76.
36. Murakami, H., K. Bessinger, J. Hellmann, and S. Murakami, *Manipulation of serotonin signal suppresses early phase of behavioral aging in Caenorhabditis elegans.* Neurobiol Aging, 2007 Feb. 28 [Epub ahead of print].
37. Sze, J. Y., M. Victor, C. Loer, Y. Shi, and G. Ruvkun, *Food and metabolic signalling defects in a Caenorhabditis elegans serotonin-synthesis mutant.* Nature, 2000. 403(6769): p. 560-4.
38. Lesurtel, M., R. Graf, B. Aleil, D. J. Walther, Y. Tian, W. Jochum, C. Gachet, M. Bader, and P. A. Clavien, *Platelet-derived serotonin mediates liver regeneration.* Science, 2006. 312(5770): p. 104-7.
39. Matsuda, M., T. Imaoka, A. J. Vomachka, G. A. Gudelsky, Z. Hou, M. Mistry, J. P. Bailey, K. M. Nieport, D. J Walther, M. Bader, and N. D. Horseman, *Serotonin regulates mammary gland development via an autocrine-paracrine loop.* Dev Cell, 2004. 6(2): p. 193-203.
40. Nebigil, C. G., D. S. Choi, A. Dierich, P. Hickel, M. Le Meur, N. Messaddeq, J. M. Launay, and L. Maroteaux, *Serotonin 2B receptor is required for heart development.* Proc Natl Acad Sci U serotonin A, 2000. 97(17): p. 9508-13.
41. Westbroek, I., A. van der Plas, K. E. de Rooij, J. Klein-Nulend, and P. J. Nijweide, *Expression of serotonin receptors in bone.* J Biol Chem, 2001. 276(31): p. 28961-8.
42. Hanley, H. G., S. M. Stahl, and D. X. Freedman, *Hyperserotonemia and amine metabolites in autistic and retarded children.* Arch Gen Psychiatry, 1977. 34(5): p. 521-31.
43. Hediger, M. L., L. J. England, C. A. Molloy, K. F. Yu, P. Manning-Courtney, and J. L. Mills, *Reduced Bone Cortical Thickness in Boys with Autism or Autism Spectrum Disorder.* J Autism Dev Disord, 2007.
44. Warden, S. J., A. G. Robling, M. S. Sanders, M. M. Bliziotes, and C. H. Turner, *Inhibition of the serotonin (5-hydroxytryptamine) transporter reduces bone accrual during growth.* Endocrinology, 2005. 146(2): p. 685-93.
45. Mann, J. J., P. A. McBride, R. P. Brown, M. Linnoila, A. C. Leon, M. DeMeo, T. Mieczkowski, J. E. Myers, and M. Stanley, *Relationship between central and peripheral serotonin indexes in depressed and suicidal psychiatric inpatients.* Arch Gen Psychiatry, 1992. 49(6): p. 442-6.
46. Blakely, R. D., L. J. Defelice, and A. Galli, *Biogenic amine neurotransmitter transporters: just when you thought you knew them.* Physiology (Bethesda), 2005. 20: p. 225-31.
47. Eldridge, F. L. and D. E. Millhorn, *Central regulation of respiration by endogenous neurotransmitters and neuromodulators.* Annu Rev Physiol, 1981. 43: p. 121-35.
48. Noda, M., H. Higashida, S. Aoki, and K. Wada, *Multiple signal transduction pathways mediated by 5-HT receptors.* Mol Neurobiol, 2004. 29(1): p. 31-9.
49. Fu, L., M. S. Patel, A. Bradley, E. F. Wagner, and G. Karsenty, *The molecular clock mediates leptin regulated bone formation.* Cell, 2005. 122(5): p. 803-15.
50. Saudou, F., D. A. Amara, A. Dierich, M. LeMeur, S. Ramboz, L. Segu, M. C. Buhot, and R. Hen, *Enhanced aggressive behavior in mice lacking 5-HT1B receptor.* Science, 1994. 265(5180): p. 1875-8.
51. Weisstaub, N. V., M. Zhou, A. Lira, E. Lambe, J. Gonzalez-Maeso, J. P. Hornung, E. Sibille, M. Underwood, S. Itohara, W. T. Dauer, M. S. Ansorge, E. Morelli, J. J. Mann, M. Toth, G. Aghajanian, S. C. Sealfon, R. Hen, and J. A. Gingrich, *Cortical 5-HT2A receptor signaling modulates anxiety-like behaviors in mice.* Science, 2006. 313(5786): p. 536-40.
52. Yang, X., K. Matsuda, P. Bialek, S. Jacquot, H. C. Masuoka, T. Schinke, L. Li, S. Brancorsini, P. Sassone-Corsi, T. M. Townes, A. Hanauer, and G. Karsenty, *ATF4 is a substrate of RSK2 and an essential regulator of osteoblast biology; implication for Coffin-Lowry Syndrome.* Cell, 2004. 117(3): p. 387-98.

What is claimed is:

1. A method of treating osteoporosis in a patient in need thereof comprising administering to the patient a therapeutically effective amount of a TPH1 inhibitor that lowers the level of peripheral serotonin in the patient;

where the TPH1 inhibitor is selected from the group consisting of:

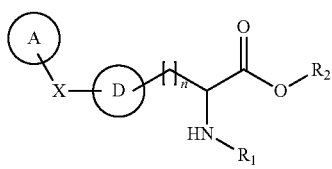

(a)

and pharmaceutically acceptable salts thereof, wherein: A is optionally substituted cycloalkyl, aryl, or heterocycle; X is a bond (i.e., A is directly bound to D), —O—, —S—, —C(O)—, —C(R4)=, =C($R_4$)—, —C($R_3R_4$)—, —C($R_4$)=C($R_4$)—, —C≡C—, —N($R_5$)—, —N($R_5$)C(O)N($R_5$)—, —C($R_3R_4$)N($R_5$)—, —N($R_5$)C($R_3R_4$)—, —ONC($R_3$)—, —C($R_3$)NO—, —C($R_3R_4$)O—, —OC($R_3R_4$)—, —S($O_2$)—, —S($O_2$)N($R_5$)—, —N($R_5$)S($O_2$)—, —C($R_3R_4$)S($O_2$)—, or —S($O_2$)C($R_3R_4$)—; D is optionally substituted aryl or heterocycle; $R_1$ is hydrogen or optionally substituted alkyl, alkyl-aryl, alkyl-heterocycle, aryl, or heterocycle; $R_2$ is hydrogen or optionally substituted alkyl, alkyl-aryl, alkyl-heterocycle, aryl, or heterocycle; $R_3$ is hydrogen, alkoxy, amino, cyano, halogen, hydroxyl, or optionally substituted alkyl; $R_4$ is hydrogen, alkoxy, amino, cyano, halogen, hydroxyl, or optionally substituted alkyl or aryl; each $R_5$ is independently hydrogen or optionally substituted alkyl or aryl; and n is 0-3; and

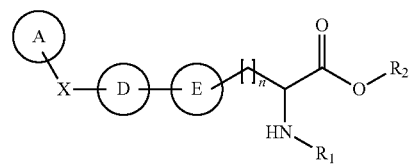

(b)

and pharmaceutically acceptable salts thereof, wherein: A is optionally substituted cycloalkyl, aryl, or heterocycle; X is a bond (i.e., A is directly bound to D), —O—, —S—, —C(O)—, —C(R4)=, =C($R_4$)—, —C($R_3R_4$)—, —C($R_4$)=C($R_4$)—, —C≡C—, —N($R_5$)—, —N($R_5$)C(O)N($R_5$)—, —C($R_3R_4$)N($R_5$)—, —N($R_5$)C($R_3R_4$)—, —ONC($R_3$)—, —C($R_3$)NO—, —C($R_3R_4$)O—, —OC($R_3R_4$)—, —S($O_2$)—, —S($O_2$)N($R_5$)—, —N($R_5$)S($O_2$)—, —C($R_3R_4$)S($O_2$)—, or —S($O_2$)C($R_3R_4$)—; D is optionally substituted aryl or heterocycle; E is optionally substituted aryl or heterocycle; $R_1$ is hydrogen or optionally substituted alkyl, alkyl-aryl, alkyl-heterocycle, aryl, or heterocycle; $R_2$ is hydrogen or optionally substituted alkyl, alkyl-aryl, alkyl-heterocycle, aryl, or heterocycle; $R_3$ is hydrogen, alkoxy, amino, cyano, halogen, hydroxyl, or optionally substituted alkyl; $R_4$ is hydrogen, alkoxy, amino, cyano, halogen, hydroxyl, or optionally substituted alkyl or aryl; each $R_5$ is independently hydrogen or optionally substituted alkyl or aryl; and n is 0-3.

2. The method of claim 1 where the agent is selected from the group consisting of:

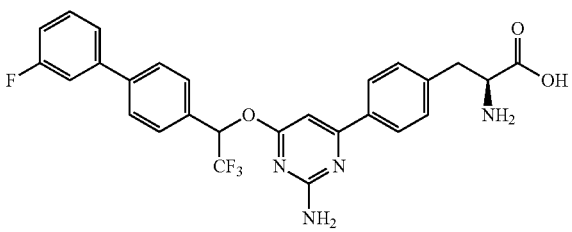

(a)

and pharmaceutically acceptable salts thereof; and

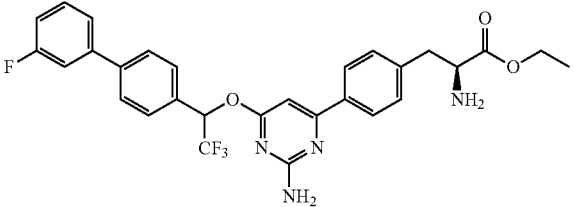

(b)

and pharmaceutically acceptable salts thereof.

* * * * *